US007074611B2

(12) United States Patent
Chambon et al.

(10) Patent No.: US 7,074,611 B2
(45) Date of Patent: Jul. 11, 2006

(54) METHOD FOR THE STABLE INVERSION OF DNA SEQUENCE BY SITE-SPECIFIC RECOMBINATION AND DNA VECTORS AND TRANSGENIC CELLS THEREOF

(75) Inventors: Pierre Chambon, Blaesheim (FR); Norbert B. Ghyselinck, Strasbourg (FR); Frank Schnutgen, Alzenau (DE)

(73) Assignee: GIE-Cerbn, Centre Europeen de Recherche en Biologie et en Medecine (GIE), Illkirch (FR)

( * ) Notice: Subject to any disclaimer, the term of this patent is extended or adjusted under 35 U.S.C. 154(b) by 0 days.

(21) Appl. No.: 09/843,150

(22) Filed: Apr. 27, 2001

(65) Prior Publication Data

US 2003/0159160 A1 Aug. 21, 2003

(51) Int. Cl.
*C12N 15/63* (2006.01)
*C12N 15/11* (2006.01)

(52) U.S. Cl. .................................. 435/320.1; 536/23.1

(58) Field of Classification Search ............... 536/23.1, 536/24.1, 23.4; 455/320.1, 255.1, 91.4

See application file for complete search history.

(56) References Cited

FOREIGN PATENT DOCUMENTS

| | | | |
|---|---|---|---|
| WO | WO 00/63410 | A1 | 10/2000 |
| WO | WO 01/05987 | A1 | 1/2001 |
| WO | WO 02/40685 | A2 | 5/2002 |

OTHER PUBLICATIONS

Berendsen, Hermann, Science. Oct. 1998, vol. 282, pp. 642-643.*

Feng et al., "Site-specific Chromosomal Integration in Mammalian Cells: Highly Efficient CRE Recombinase-mediated Cassette Exchange," *J. Mol. Biol.*, 1999, pp. 779-785, vol. 292, No. 4, ©Academic Press, London, Great Britain.

Snaith et al., "Multiple cloning sites carrying *loxP* and *FRT* recognition sites for the Cre and Flp site-specific recombinases," *Gene*, 1995, pp. 173-174, vol. 166, No. 1, © Elsevier Science B.V., Amsterdam, Netherlands.

Wild et al., "Targeting and retrofitting pre-existing libraries of transposon insertions with *FRT* and *oriV* elements for in-vivo generation of large quantities of any genomic fragment," *Gene*, 1998, pp. 55-66, vol. 223, No. 1-2, © Elsevier Science B.V., Amsterdamn, Netherlands.

* cited by examiner

*Primary Examiner*—Ram R. Shukla
*Assistant Examiner*—Patrick S. Riggins
(74) *Attorney, Agent, or Firm*—Foley & Lardner LLP

(57) ABSTRACT

The invention relates to a method for the stable inversion of a DNA fragment upon recombinase-mediated rearrangements using two sets of two incompatible site-specific recombinase targeting sites (SSRTS) in the same order but in reverse orientation flanking the DNA fragment to be inverted. The invention also relates to a method for the stable inversion of the DNA fragment upon rearrangement mediated by a recombinase such as Cre recombinase. The invention also relates to a method for obtaining a transgenic cell of which at least one allele of a DNA sequence of interest is invalidated by a process of conditional deletion and the genome of which has a reporter gene inserted at the place of the DNA fragment deleted by the process of conditional deletion. A method to generate targeting sites to perform site-specific recombination mediated cassette exchange is also provided.

15 Claims, 12 Drawing Sheets

METHOD FOR THE STABLE INVERSION OF DNA SEQUENCE BY SITE-SPECIFIC RECOMBINATION AND DNA VECTORS AND TRANSGENIC CELLS THEREOF

The present invention relates to biology and the technical field of genetic manipulation in a cell-free system, in isolated cells or in living organisms. More precisely, the invention relates to an isolated DNA molecule comprising at least a sequence A flanked by at least site specific recombinase targeting sequences (SSRTS) L1, and at least a sequence B flanked by at least site specific recombinase targeting sequences (SSRTS) L2, said SSRTS L1 and SSRTS L2 being unable to recombine with one another, and wherein sequences L1 are in an opposite orientation, sequences L2 are in an opposite orientation, and the order of SSRTS sequences in said DNA molecule is 5'-L1-L2-L1-L2-3'. The invention also relates to a method for the stable inversion of said DNA fragment A and/or B upon rearrangement mediated by recombinase such as Cre recombinase. The invention also relates to a method for obtaining a transgenic cell of which at least one allele of a DNA sequence of interest is invalidated by a process of conditional deletion and the genome of which comprises a reporter gene inserted at the place of the DNA fragment deleted by said process of conditional deletion. The invention also concerns a method to generate targeting sites allowing site-specific recombination mediated cassette exchange. The corresponding vector, host cells, and transgenic animals are claimed.

The advent of homologous recombination in mouse embryonic stem (ES) cells has provided a powerful system to analyze mammalian gene functions (Capecchi, 1989). In most studies, the primary goal has been to generate germ line null mutations (knockouts) of given genes, i.e. inactivation in all stages of life throughout the body. Such mutations have shown the extreme complexity of genetic determination in mammals. We are now facing several complicating phenomena, such as functional redundancy between genes belonging to large families, and developmental lethal phenotypes that prevent the study of either the complete spectrum of actions, or later functions of a given gene, respectively (Thomas, 1993; Copp, 1995).

The use of site-specific recombinases, mainly the Cre recombinase of the bacteriophage P1 and the yeast FLP recombinase, that catalyze the recombination of DNA between two specific targeting-sites [loxP and FRT sites, respectively (Sauer, 1988; O'Gorman, 1991)], now permits to study mice harboring somatic gene alterations which are either temporally- or spatially-restricted (Sauer et Henderson, 1989; Orban et al., 1992; Gu et al., 1993; Tsien et al., 1996; Nagy et al., 2000). The recent development of inducible forms of recombinases further gives the opportunity to induce gene alterations both at precise time points, and in specific cell types (Logie et Stewart, 1995; Metzger et al., 1995; Kellendonk et al., 1996; Brocard et al., 1997; Danielan et al., 1998; Schwenk et al., 1998; Li et al., 2000). These recombination-based strategies are likely to have a profound impact on developmental biology and the elucidation of gene physiological functions, and will also allow the generation of models for human diseases particularly when the underlying genetic changes, such as initiation of cancer, are somatic in nature. However, these strategies all require the availability of recombinase-expressing transgenic mouse lines, whose recombinase activity must be carefully characterized at the cellular level. This is usually performed using additional transgenic lines, whose capacity to express a reporter gene in given cells is dependent on a recombinase-mediated event (Akagi et al., 1997; Lobe et al., 1999; Mao et al., 1999; Soriano et al., 1999; Kawamoto et al., 2000; Novak et al., 2000). However, a frequently encountered problem in transgenic animal studies is position effect variegation, that frequently leads to mosaicism of transgene expression (Koestier et al., 1996). Concomitant mosaic expression of both the recombinase and reporter transgenes in 60% of the target cell population would dramatically limit the final reporter expression to only 36% (reviewed in Sauer, 1998). Moreover, even when both the recombinase and reporter transgene are expressed in the same cell, the latter may lie in a chromatin configuration inaccessible to recombination, further confounding analyses (Kellendonk et al., 1999). Altogether, these observations lead to the conclusion that one cannot easily extrapolate from the expression pattern of a reporter transgene to an identical targeting pattern for a conditional allele of a given gene.

The problem to be solved is to develop a system that would permit a clear identification of each individual cell in which recombination has taken place, at a given gene locus.

The inventors have solved the problem underlying the invention by developing a novel strategy that allows to readily detect individual cells in which Cre-mediated rearrangements have occurred. It relies upon (i) the property of Cre recombinase to both invert and excise any intervening DNA flanked by two loxP sites placed in opposite and identical orientations, respectively (Abremski et al., 1983), and (ii) the use of lox511 mutant sites, that can recombine with themselves, but not with wild type loxP sites (Hoess et al., 1986). Making use of this strategy for gene targeting in ES cells not only facilitates the identification of individual cells that undergo conditional gene inactivation in the mouse, but also allows spatio-temporally controlled sophisticated site-specific DNA modifications.

The present invention provides an isolated DNA molecule comprising at least a sequence A flanked by at least site specific recombinase targeting sequences (SSRTS) L1, and at least a sequence B flanked by at least site specific recombinase targeting sequences (SSRTS) L2, said SSRTS L1 and SSRTS L2 being unable to recombine with one another, and wherein the sequences L1 are in an opposite direction, the sequences L2 are in an opposite direction, and wherein the order of SSRTS sequences in said DNA molecule is 5'-L1-L2-L1-L2-3'. In one embodiment the order of sequences in said DNA molecule is: 5'-L1-sequence A-L2-sequence B-L1-L2-3'. In another embodiment, the order of sequences in said DNA molecule is: 5'-L1-L2-sequence A-sequence B-L1-L2-3'. In another embodiment, the order of sequences in said DNA molecule is 5'-L1-L2-sequence A-L1-sequence B-L2-3'.

As used herein, the term "DNA molecule" refers to a polynucleotide sequence such as a single or double stranded DNA sequence; such a polynucleotide sequence has been isolated or synthesized and may be constituted with natural or non natural nucleotides. In a preferred embodiment the DNA molecule of the invention is a double stranded DNA molecule.

Site specific recombinases are enzymes that are present in some viruses and bacteria and have been characterized to have both endonuclease and ligase properties. These recombinases (along with associated proteins in some cases) recognize specific sequences of bases in DNA and exchange the DNA segments flanking those segments (Landy et al., 1993). Site specific recombinases catalyze at least the following four events (1) deletion of a DNA fragment flanked by compatible site-specific recombinase targeting sites (SSRTS) in the same orientation (e.g. head-to-tail or tail-to-head); (b) inversion of a DNA fragment flanked by compatible SSRTS in opposite orientation (e.g. head-to-head or tail-to-tail); (c) integration of a cyclic DNA fragment containing an SSRTS into a compatible SSRTS; and (d) chromosomal translocation between compatible SSRTS located on different chromosomes. To perform those reactions, the site-specific recombinase has typically at least the following four activities: (1) recognition of one or two specific DNA sequences; (2) cleavage of said DNA sequence or sequences; (3) DNA topoisomerase activity involved in strand exchange; and (4) DNA ligase activity to reseal the cleaved strands of DNA (Sauer, 1994). Numerous recombination systems from various organisms have been described (Hœss, 1986; Abremski et al., 1986, Campbell, 1992; Qian et al., 1992; Araki et al., 1992; Maeser et al., 1991; Argos et al., 1986). Perhaps the best studied of these are the Integrase/att system from bacteriophage λ (Landy, 1993), the Cre/loxP system from bacteriophage P1 (Hœss and Abremski (1990), and the FLP/FRT system from the *Saccharomyces cerevisiae* 2 mu circle plasmid (Broach et al., 1982). Bebee et al. (U.S. Pat. No. 5,434,066) discloses the use of site-specific recombinases such as Cre for DNA containing two loxP sites is used for in vivo recombination between the sites. Hasan and Szybalski (1987) discloses the use of λInt recombinase in vivo for intramolecular recombination between wild type attP and attB sites which flank a promoter. Because the orientations of these sites are inverted relative to each other, this causes an irreversible flipping of the promoter region relative to the gene of interest. Posfai et al. (1994) discloses a method for inserting into genomic DNA partial expression vectors having a selectable marker, flanked by two wild-type FRT recognition sequences. FLP site-specific recombinase as present in the cells is used to integrate the vectors into the genome at predetermined sites. Schlake & Bode (1994) discloses an in vivo method to exchange expression cassettes at defined chromosomal locations, each flanked by a wild type and a spacer-mutated FRT recombination site. A double-reciprocal crossover was mediated in cultured mammalian cells by using this FLP/FRT system for site-specific recombination.

The recombinase specific of said SSRTS is selected from the group of site-specific recombinases composed of the Cre recombinase of bacteriophage P1, the FLP recombinase of *Saccharomyces cerevisiae*, the R recombinase of *Zygosaccharomyces rouxii* pSR1, the A recombinase of *Kluyveromyces drosophilarium* pKD1, the A recombinase of *Kluyveromyces waltii* pKW1, the integrase λInt, the recombinase of the GIN recombination system of the Mu phage, of the bacterial β recombinase or a variant thereof. In a preferred embodiment, the recombinase is the Cre recombinase of bacteriophage P1 (Abremski et al., 1984), or its natural or synthetic variants. Cre is available commercially (Novagen, Catalog No. 69247-1). Recombination mediated by Cre is freely reversible. Cre works in simple buffers with either magnesium or spermidine as a cofactor, as is well known in the art. The DNA substrates can be either linear or supercoiled. A number of mutant loxP sites have been described (Hoess et al., 1986; Lee et al., 1998), indeed, the corresponding SSRTS L1 and/or L2 specific for said Cre recombinase are chosen from the group composed of the sequences Lox P1 (ATCC 53 254 et 20 773), Lox 66, Lox 71, Lox 511, Lox 512, Lox 514, Lox B, Lox L, Lox R and mutated sequences of Lox P1 site harboring at least one point mutation in the 8 nucleotide spacer sequence. In one embodiment, the point mutation is substitution of A for G at position 7 of the eight base spacer sequence of the wild type Lox P1 sequence, referred to herein as the Lox511 sequence. Preferred SSRTS are Lox P1 (SEQ ID N° 52) and Lox 511 (SEQ ID N° 53).

Such Lox 511 recombines with another Lox 511 site, but cannot recombine with another Lox P site such as a Lox P1 site. Accordingly, in a preferred embodiment, the SSRTS L1 comprises the Lox P1 nucleotide sequence and SSRTS L2 comprises the Lox 511 nucleotide sequence or SSRTS L1 comprises the Lox 511 sequence and SSRTS L2 comprises Lox P1 sequence. In another embodiment, the recombinase is the FLP recombinase of *Saccharomyces cerevisiae*, or its natural or synthetic variants and the SSRTS L1 and/or L2 specific for said FLP recombinase are chosen from the group composed of the sequences FRT-S and FRT-F3$^{0.88}$.

Site-specific recombinase variants means the wild type recombinases, or fragments thereof, that correspond to truncations, substitutions, deletions and/or additions of amino acid moieties. In a preferred embodiment, these recombinases and the fragments thereof correspond to variations due to genetic polymorphism. Recombinase fragment means any part of the recombinase with at least a recombinase activity. Site-specific recombinase variants also means synthetic variants in which the preceding modifications are not naturally present but have been artificially introduced, by genetic engineering for example. Indeed recombinases obtained by chimeric fusions represent synthetic variants of the invention. Such recombinases have been described in Shaikh and Sadowski (2000). In one embodiment, the site-specific recombinases of the invention can be genetically engineered to be expressed as a fusion protein with a nuclear receptor for a steroid hormone such as the estrogen nuclear receptor or the glucocorticoid nuclear receptor for example. Such chimeric recombinases can be temporarily activated by the natural or a synthetic ligand of such a nuclear receptor (For review, see Feil et al., 1996; Brocard et al., 1997; Indra et al., 1999; Schwenk et al., 1998).

In one embodiment, the recombinase specific to said SSRTS L1 and the recombinase specific to said SSRTS L2 are the same. By "same recombinase" it is meant that the recombinase specific to SSRTS L1 catalyzes recombination at SSRTS L1 and L2 and the recombinase specific to SSRTS L2 catalyzes recombination at SSRTS L2 and L1. For example, site-specific recombination is catalyzed by the "same" Cre recombinase at LoxP1 and Lox511 sequences. In another embodiment, the recombinase specific to said SSRTS L1 and the recombinase specific to said SSRTS L2 are different. By "different recombinase" it is meant that the recombinase specific to SSRTS L1 cannot catalyze recombination at a SSRTS L2 sequence and the recombinase specific to SSRTS L2 cannot catalyze recombination at a SSRTS L1. An example of site-specific recombinations catalyzed by "different" recombinases is the recombination by the Cre recombinase at the SSRTS L1 sequence corresponding to a LoxP1 site and the recombination by the FLP recombinase at the SSRTS L2 sequence corresponding to a FRT site. In another embodiment, different recombinases can respectively catalyze recombination at both SSRTS L1 and SSRTS L2 sequences; for example, a wild type and a mutated Cre recombinases can both catalyze recombination at the SSRTS L1 sequence corresponding to a LoxP1 and at the SSRTS L2 sequence corresponding to a Lox511, but these two recombinases will have a better specificity for one or the other recombination sequence.

The site-specific recombinase targeting sequences (SSRTS) are particular DNA sequences which a protein, DNA, or RNA molecule (e.g. restriction endonuclease, a modification methylase, or a recombinase) recognizes and binds. For example, the recognition sequence for Cre recombinase is loxP (locus of Cross over) which is a 34 base pair sequence comprised of two 13 base pair inverted repeats (serving as the recombinase binding sites) flanking an 8 base pair core sequence (See FIG. 1 of Sauer, 1994). As used herein, the term "direction of SSRTS" refers to the orientation of its spacer region, which determines the orientation of the complete SSRTS.

Other examples of recognition sequences are the attB, attP, attL, and attR sequences which are recognized by the recombinase enzyme λ integrase (Landy, 1993) or FRT sequences which are recognized by the FLP recombinase.

The term "SSRTS sequences unable to recombine with one another" or incompatible SSRTS sequences refers to two or more SSRTS sequences (referred to herein as L1, L2, but also L3, L4, L5, L6, . . . L10 etc . . . ) which differ from one another and, therefore, can not undergo recombination with one another. For example, lox sequences can be rendered incompatible if their nucleotide sequences differ by only one nucleotide, particularly in their spacer regions. In contrast, the term "compatible lox sequences" refers to two or more lox sequences, which can recombine when, catalyzed to do so by a recombinase.

The above recombinases and corresponding recombinase-targeting sites are suitable for use in recombination cloning according to the present invention. However, wild-type recombination targeting sites can contain sequences that reduce the efficiency or specificity of recombination reactions as applied in methods of the present invention. For example, multiple stop codons in attB, attR, attP, attL and loxP recombination sites occur in multiple reading frames on both strands, so recombination efficiencies are reduced, e.g., where the coding sequence must cross the recombination sites, (only one reading frame is available on each strand of loxP and attB sites), or impossible (in attP, attR or attL). Accordingly, the present invention also uses engineered recombination sites. For example, Lox sites can be engineered to have one or multiple mutations to enhance specificity or efficiency of the recombination reaction and the properties of the DNA of the invention, or to decrease the reverse reaction. The testing of these mutants determines which mutants yield sufficient recombinational activity to be suitable for recombination reaction according to the present invention. Mutations can therefore be introduced into recombination sites or into recombinases for enhancing site specific recombination. Such mutations introduced into recombination sites include, but are not limited to, recombination sites without translation stop codons that allow fusion proteins to be encoded, recombination sites recognized by the same proteins but differing in base sequence such that they react largely or exclusively with their homologous partners to allow multiple reactions to be contemplated. Which particular reactions take place can be specified by which particular partners are present in the reaction mixture. There are well known procedures for introducing specific mutations into nucleic acid sequences. A number of these are described in Ausubel et al. (1989). Mutations can be designed into oligonucleotides, which can be used to modify existing cloned sequences, or in amplification reactions. Random mutagenesis can also be employed if appropriate selection methods are available to isolate the desired mutant DNA or RNA. The presence of the desired mutations can be confirmed by sequencing the nucleic acid by well-known methods.

In another embodiment, said DNA molecule of the invention is further flanked by at least site specific recombinase targeting sequences (SSRTS). Such SSRTS sequences are the same or are different from the preceding ones. In a preferred embodiment such SSRTS sequences are different and are placed in the same orientation to further allow the excision of said DNA molecule, or are placed in the opposite orientation to further allow the inversion of said DNA molecule or are incompatible sequences to allow site-specific recombination mediated cassette exchange (RMCE). It is also in the scope of the present invention to create DNA molecules of the invention or to use the method of the invention with additional sets of SSRTS sequences (L3, L4, L5, L6, . . . , L10 etc . . . ) in order to multiply the possibilities of such a system.

In a preferred embodiment, the sequences A and B are in the opposite orientation. By sequences A and B in the opposite orientation, it means that the coding sequences of sequences A and B are not present on the same DNA strand. Thus, on the same strand, sequence A is orientated 5' to 3' and sequence B is orientated 3' to 5'. In another embodiment, the sequences A and B are in the same orientation; this means that the coding sequences of sequences A and B are present on the same DNA strand. Sequences A and B comprise at least non transcribed sequences, transcribed but not translated sequences, transcribed and translated sequences (i.e. gene). In a preferred embodiment, sequences A and/or B can encode for at least one gene. The term "gene" refers to a nucleic acid sequence that encodes a protein or a peptide. This gene can derive from genomic DNA or recombinant DNA such as cDNA. Said gene encodes a protein, a polypeptide, a peptide, protein fragments, for example an exon; more precisely said protein is selected in the group consisting of reporter proteins, selectable markers and proteins of interest.

The reporter protein of the invention is selected in the group consisting of autofluorescent proteins and enzymes detectable by a histochemical process. The autofluorescent protein is selected in the group consisting of the green fluorescence protein (GFP), the enhanced green fluorescence protein (EGFP), the red fluorescence protein (RFP), the blue fluorescence protein (BFP), the yellow fluorescence protein (YFP) and the fluorescent variant of these proteins. The enzyme detectable by a histochemical process is selected in the group consisting of β-galactosidase, β-glucoronidase, alcaline phosphatase, luciferase, alcohol deshydrogenase, chloramphenicol-acetyl transferase, peroxydase. In a preferred embodiment, the β-galactosidase gene is used. The substrate to be used with these specific enzymes are generally chosen for the production, upon hydrolysis by the corresponding enzyme, of a detectable colour change. Substrate can be soluble or insoluble, added into the culture medium or in the organism, or present in the host cell, depending upon the chosen method. For example, 5-bromo-4-chloro-3-indoyl phosphate/nitroblue tetrazolium is suitable for use with alkaline phosphatase conjugates; for peroxidase conjugates, 1,2-phenylenediamine-5-aminosalicylic acid, 3,3,5,5,-tetramethylbenzidine, tolidine or dianisidine are commonly used.

In a second preferred embodiment, the reporter gene is the luciferase gene.

Selectable marker means a DNA segment that allows one to select for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions and the like. Examples of selectable markers include but are not limited to DNA segments that encode products which provide resistance against otherwise toxic compounds (e.g., antibiotics). For example, the ampicillin or the neomycin resistance genes constitute selectable marker of the invention. These selectable markers can be either positive or negative (see Capecchi et al., U.S. Pat. No. 5,631,153). For example, the pair (positive selectable marker gene/selective agent) is selected among: (Neomycine resistance gene/G418), (Hygromycine resistance gene/Hygromycine), (His D gene/Histidinol), (Gpt gene/Xanthine), (HGPRT gene/Hypoxanthine).

For example, the pair (negative selectable marker/selective agent) is selected among: (HSV-TK gene/Acyclovir-Gancyclovir), (HPRT/6-Thioguanine), (GPT/6-Thioguanine), (Cytosine deaminase/5 fluoro-cytosine). The selectable marker can also be the diphteric toxin A (DTA).

Selectable markers also include DNA segments that encode products which are otherwise lacking into the recipient cell (e.g., tRNA genes, auxotrophic markers), or DNA segments that encode products which suppress the activity of a gene product.

The protein of interest of the present invention can be any protein. For example, the protein of interest can be a therapeutic protein, such as α-, β-, δ-globin, blood coagulation factors (e.g., Factors VIII and IX), cell surface receptors, enzymes and other desirable proteins, for example, to correct inherited or acquired deficiencies of these proteins in an individual.

In one embodiment, the sequences A and/or B are coding for at least one exon, or a fragment thereof. In a preferred embodiment, said exon differs from the wild type exon of a protein of interest by one or more point mutations. Those point mutations can be deletions, insertions or substitutions. In the case that a fusion translation product is synthetized, one can introduce an IRES (Internal ribosome entry site) in the gene sequence. For example, said protein can be encoded by a cDNA sequence, and an IRES sequence can be inserted in a position 5', or 3', or 5' and 3' to said cDNA sequence.

Sequences A and/or B can contain all the genetic information needed for gene(s) expression such as promoter sequences, regulatory upstream elements, transcriptional and/or translational initiation, termination and/or regulation elements.

The present invention also provides a vector comprising the isolated DNA molecule of the invention. A "vector" is a replicon in which another polynucleotide segment is attached, so as to allow the replication and/or expression of the attached segment. Examples of vectors include plasmids, phages, cosmids, phagemids, yeast artificial chromosomes (YAC), bacterial artificial chromosomes (BAC), human artificial chromosomes (HAC), viral vectors, such as adenoviral vectors, retroviral vectors, and other DNA sequences which are able to replicate or to be replicated in vitro or in a host cell, or to convey a desired DNA segment to a desired location within a host cell. A vector can have one or more restriction endonuclease recognition sites at which the DNA sequences can be cut in a determinable fashion without loss of an essential biological function of the vector, and into which a DNA fragment can be spliced in order to bring about its replication and cloning. Vectors can further provide primer sites (e.g. for PCR), transcriptional and/or translational initiation and/or regulation sites, recombinational signals, replicons, selectable markers, etc. Beside the use of homologous recombination or restriction enzymes to insert a desired DNA fragment into the vector, UDG cloning of PCR fragments (U.S. Pat. No. 5,334,575), T:A cloning, and the like can also be applied. The cloning vector can further contain a selectable marker suitable for use in the identification of cells transformed with the cloning vector.

The present invention also relates to the use of the isolated DNA molecule or the vector of the invention as a transgene. Such transgene can be introduced into a host cell either in vivo or in vitro using known techniques, such as $CaPO_4$ precipitation, electroporation, cationic lipofection, use of artificial viral envelopes, direct injection (e.g., intravenous, intraperitoneal or intramuscular micro-injection into a zygote or a pronucleus of a zygote) Thus, the invention relates to an isolated transgenic host cell transformed by an isolated DNA molecule or a vector according to the invention. A "host", as the term is used herein, includes prokaryotic or eukaryotic organisms that can be genetically engineered. For examples of such hosts, see Sambrook et al., (1989).

In a preferred embodiment, the isolated DNA molecule or vector of the invention is integrated by homologous recombination in at least one targeted locus of the genome of the isolated transgenic host cell of the invention. To perform such homologous recombination, it is preferable that sequences of homology are present at both extremities of said DNA molecule.

In another embodiment, said isolated DNA molecule or said vector is integrated in sites of the genome of said isolated transgenic host cell chosen among polyA sites and gene promoters. The specific embodiment allows one to perform gene trapping which is a general method for mutagenesis based on random integration of a DNA fragment encoding for a reporter gene or a selectable marker gene (Hill and Wurst, 1993). Two gene trap methods are commonly used, the polyA trap based method and the promoter based method.

In another embodiment said isolated DNA molecule or said vector is randomly integrated in at least one locus of the genome of said isolated transgenic host cell.

In another embodiment said isolated DNA molecule or said vector is maintained in an episomal form in said isolated transgenic host cell.

The present invention also relates to the transgenic organism, comprising at least one cell according to the invention. An "organism" as the term is used herein, includes but is not limited to, bacteria, yeast, animal, plants. Among the animals, one can designate mammals, such as rodents, primates, including humans, farm animals. In a preferred embodiment, the animal is a mouse, a rat, a Guinea pig, a hamster, a rabbit, a pig, a cow, a horse, a goat, a sheep.

In another embodiment, the invention relates to a method for the stable inversion of a DNA sequence comprising the steps of (i) contacting a DNA molecule according to the invention, or a DNA vector according to the invention with at least one recombinase specific of said SSRTS L1 and one recombinase specific specific to said SSRTS L2; and (ii) inversion of said sequences A and B or sequence A or sequence B by recombination catalyzed by said recombinase at either SSRTS L1 or L2 sequences; and (iii) excision by recombination catalyzed by said recombinase of a DNA fragment comprised between the SSRTS L1 or L2 sequences that are now present in the same orientation following the inversion of step (ii), and that are able to recombine with one another. In a preferred embodiment, said DNA fragment excised in step (iii) comprises the sequence A.

In another embodiment, the invention relates to a method for obtaining a transgenic cell of which at least one allele of a DNA sequence of interest is invalidated by a process of conditional deletion and the genome of which comprises a reporter gene and/or a marker gene and/or a gene encoding a protein of interest inserted at the place of the DNA fragment deleted by said process of conditional deletion, said method comprises the steps of (i) preparation of a DNA molecule according to the invention wherein sequence A or sequence B is coding at least for part of the DNA fragment of interest to be invalidated and sequence B or sequence A is coding at least for a reporter gene and/or a marker gene and/or a gene encoding a protein of interest; (ii) obtention of a transgenic cell genetically modified by the targeted insertion by homologous recombination at the place of said DNA sequence of interest, of a DNA molecule prepared at step (i); (iii) contacting said DNA molecule with at least one recombinase specific to SSRTS L1 and one recombinase specific to SSRTS L2; (iv) inversion of sequences A and B or sequence A or sequence B by recombination catalyzed by said recombinase at either SSRTS L1 or SSRTS L2 sequences; and (v) excision of a DNA sequence by recombination catalyzed by said recombinase at SSRTS L2 or SSRTS L1 respectively, these SSRTS L2 or SSRTS L1 sequences being now present in the same orientation following the inversion of step (iii), and being able to recombine with one another. In a preferred embodiment, the order of sequences in said DNA molecule is 5'-L1-sequence A-L2-sequence B-L1-L2-3' and a sequence of homology with the DNA sequence of interest are present at both extremities of said DNA molecule in order to perform homologous recombination and the DNA fragment excised in step (v) comprises sequence A. In another embodiment, the order of sequences in said DNA molecule is 5'-L1-L2-sequence A-sequence B-L1-L2-3' and a sequence of homology with the DNA sequence of interest is present at both extremities of said DNA molecule. In another embodiment, the order of sequences in said DNA molecule is 5'-L1-L2-sequence A-L1-sequence B-L2-3' and a sequence of homologis with the DNA sequence of interest are present at both extremities of said DNA molecule. In a preferred embodiment, said reporter gene, marker gene, and gene encoding the protein of interest of the invention encoded by the DNA sequence is only expressed following the inversion step (iv). The reporter gene, the marker gene, the gene encoding the protein of interest of the invention can be promotorless so that it will only be expressed when integrated into the targeted DNA molecule (i.e. the acceptor molecule) containing a promoter to drive its expression.

In another embodiment, the invention relates to a method to generate targeting sites allowing site-specific recombination mediated cassette exchange (RMCE), said method comprising the steps of (i) preparation of a first DNA molecule comprising a first DNA sequence of interest flanked by incompatible SSRTS L1 and L2 in an opposite orientation, obtainable by the method of the invention; (ii) preparation of a second DNA molecule comprising a second DNA sequence of interest flanked by the same incompatible SSRTS L1 and L2 as in step (i) in an opposite orientation, by an in vitro DNA cloning method; (iii) contacting said first and said second DNA molecule with at least one recombinase specific to said SSRTS L1 and one recombinase specific to said SSRTS L2; and (iv) exchange by recombination catalyzed by said recombinase of said first and said second DNA sequence of interest comprised between the SSRTS L1 and L2. Said in vitro DNA cloning method of step (ii) is any method known by the man skilled in the art that can be used to clone said second molecule. Such methods use basic tools that are described in Sambrook et al. (1989) for example. In another embodiment, said second DNA molecule of step (ii) is obtainable by the method of the invention. The method of the present invention, to perform site-specific RMCE, utilizes a recombinase mediated exchange reaction which takes place between identical or compatible (i.e., able to recombine with one another) SSRTS sequences. The efficient exchange of DNA between identical or compatible SSRTS sequences enables transfer of DNA from an acceptor (said first DNA molecule) to a donor (the second DNA molecule), each of which contains identical or compatible SSRTS sites.

However, once transferred from donor to acceptor vector (i.e., intermolecular transfer), the transferred DNA is "locked" into place due to the incompatibility of the two SSRTS L1 and L2 sequences within the acceptor vector which prevent intramolecular exchange and excision of the transferred DNA. Therefore, the transferred DNA is integrated in a highly stable manner. The DNA which is transferred from the donor to the acceptor vector by way of the site-specific recombination method of the invention can be any DNA desired for stable integration into a host cell genome.

In a first embodiment, the steps of the methods of the invention are performed in a cell free system.

In a second embodiment, the steps of the methods of the invention are performed in the isolated host cell or in the cell of the organism of the invention. In these latter cases, these methods can further comprise a step of introducing into the cell a gene encoding the corresponding site-specific recombinase. The introduction of the site-specific recombinase can be made via the introduction of an expression vector comprising a gene coding for said recombinase. In a preferred embodiment, such gene encoding said site-specific recombinase is stably inserted into the genome of said cell. In another embodiment said vector is maintained in said cell in an episomal form. The Recombinase expression can be driven by a promoter or a tissue-specific promoter: the expression can be either constitutive or inducible. In another embodiment, the recombinase gene or the recombinase gene product is injected into the cell by micro-injection, or by liposome fusion for example.

In a preferred embodiment, of the methods of the invention, the SSRTS L1 sequence comprises the Lox P1 sequence and SSRTS L2 sequence comprises the Lox 511 sequence, or SSRTS L1 sequence comprises the Lox 511 sequence and SSRTS L2 sequence comprises Lox P1 sequence, and the corresponding site-specific recombinase is Cre or its natural or synthetic variants.

More generally, the invention relates to the use of a DNA molecule, and/or a vector, and/or a cell of the invention to perform site-specific stable inversion of a DNA sequence. In a preferred embodiment, the invention relates to the use of a DNA molecule, and/or a vector, and/or a cell of the invention to perform site-specific recombination mediated cassette exchange (RCME).

It is also a goal of the invention to furnish kits for performing stable inversion of DNA sequence and/or site-specific recombination cassette exchange (RCME), said kit comprising at least a DNA molecule, and/or a vector, and/or a cell of the invention.

It is also a goal of the invention to furnish a living organism, except human, that comprises at least one transgenic cell obtainable by the method of the invention. Said organism is selected in the group consisting of bacteria, yeast, *Caenorhabditis elegans, Drosophila melanogaster*, zebrafish, mice, rat, rabbit, hamster, Guinea pig, cow, pig, goat, sheep, horse, primate. In a preferred embodiment, the living organism of the invention is a mouse. In another preferred embodiment, the living organism of the invention is a yeast.

Accordingly, the methods, DNA molecules and vectors of the invention can be used for a variety of therapeutic and diagnostic applications which require stable and efficient integration of transgene sequences into genomic DNA of cells (gene therapy). The methods, DNA molecules and vectors can be used to transform a wide variety of eukaryotic cells (e.g., mammalian) cells and provide the advantage of high efficiency DNA transfer.

The figures and examples presented below are provided as further guide to the practitioner of ordinary skill in the art and are not to be construed as limiting the invention in anyway.

EXAMPLES

1. Materials and Methods

Figure 1:
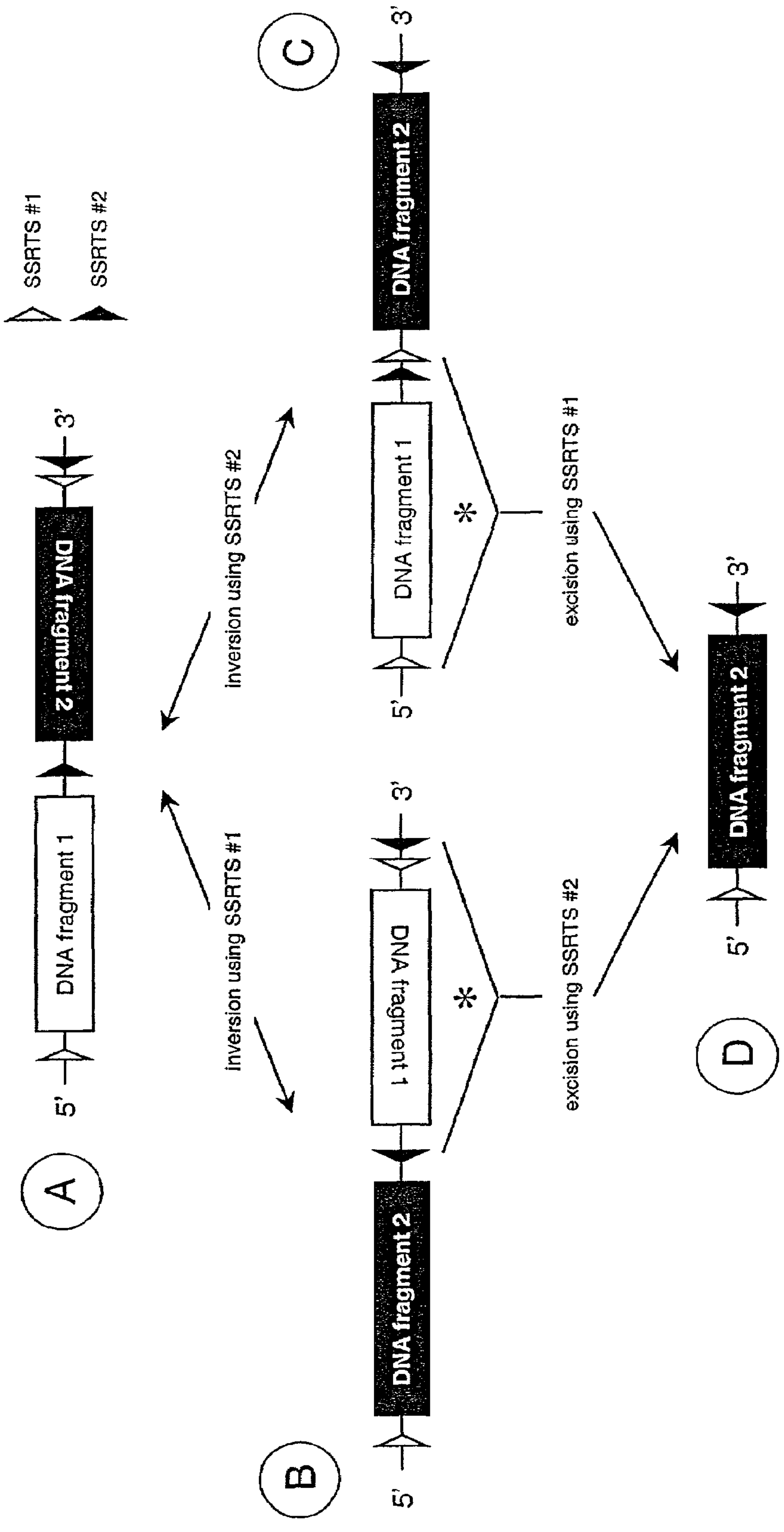
FIGS. 1A–1D. General scheme of the proposed methods. (A) Schematic drawing of a DNA, allowing conditional exchange of fragment 1 (or fragment A) by fragment 2 (or fragment B), consisting of SSRTS L1, DNA fragment 1, SSRTS L2 in sense orientation, DNA fragment 2, in antisense orientation, SSRTS L1 and SSRTS L2 reversely orientated to the first SSRTS L1 and to the first SSRTS L2, respectively. (B) Intermediate step after recombinase-mediated inversion at SSRTS L1, leading to directly repeated SSRTS L2 (asterisk) flanking DNA fragment 1. This reaction represents an equilibrium with the substrate (A). (C) Intermediate step after recombinase-mediated inversion at SSRTS L2, leading to directly repeated SSRTS L1 (asterisk) flanking DNA fragment 1. This reaction represents an equilibrium with the substrate (A). (D) Final DNA after recombinase-mediated excision of DNA fragment 1 between the directly repeated SSRTS (asterisks). This reaction is not reversible and will shift the equilibrium from the first reaction towards the product (D).

1.1. DNA Constructs.

To construct plasmid pFlExP (SEQ ID NO. 54) (FIG. 1A), a loxP site, in the sense orientation, followed by a 21-bp spacer (oligos R1/R2; Table 1) was introduced into the EcoRI site of pSG5 (Green et al., 1988). A lox511 site (Hoess et al., 1986), also in the sense orientation, followed by a 21-bp spacer (oligos R3/R4) was introduced 3' to the loxP site. A second loxP site, in the antisense orientation, followed by a 21-bp spacer (oligos R5/R6) was introduced 3' to the first loxP and lox511 sites. A second lox511 site, also in the antisense orientation, followed by a 21-bp spacer (oligos R7/R8), was introduced 3' to the latter loxP site. The coding sequence of the enhanced green fluorescent protein (Zhang et al., 1996) (EGFP; PCR-amplified using oligos R9/R10) and an NLS-β-galactosidase pA cassette (LacZ) (Bonnerot et al., 1987) were introduced between the two sets of loxP sites, in the sense and the antisense orientation, respectively. Finally, the remaining LacZ sequences of pSG5 were removed by digestion with BsaAI and SfiI, and repair by homologous recombination in *E. coli* using a SV40 promoter fragment (PCR amplified using oligos R11/R12). All cloning steps were checked by sequencing. The final constructs were again sequenced in all modified parts before starting in vitro Cre-mediated recombination or cell culture experiments. Modifications were all carried out following standard protocols (Ausubel et al., 1989). To obtain plasmid pFlExRrec, pFlExR was incubated with the Cre preparation (see below), and the recombined DNA was cloned in *E. coli*. pFlExRrec structure was checked by restriction mapping and sequencing of the regions containing loxP and lox511 sites. Plasmids ploxlacZlox and pSG5-Cre have been described elsewhere (Feil et al., 1997).

TABLE 1

Sequences of primers used for construction of the pFlExR plasmid (SEQ ID N° 54).

| Name | Sequence | |
|---|---|---|
| R1 | 5'-ATTG**ATAACTTCGTATAGCATACATTATACGAAGTTAT**CCAAGCTTCACCATCGACCCG-3' | (SEQ ID N° 1) |
| R2 | 5'-AATTCGGGTCGATGGTGAAGCTTGG**ATAACTTCGTATAATGTATGCTATACGAAGTTAT**C-3' | (SEQ ID N° 2) |
| R3 | 5'-AATTGCCAAGCATCACCATCGACCC**ATAACTTCGTATAGTATACATTATACGAAGTTAT**CG-3' | (SEQ ID N° 3) |
| R4 | 5'-AATTCG**ATAACTTCGTATAATGTATACTATACGAAGTTAT**GGGTCGATGGTGATGCTTGGC-3' | (SEQ ID N° 4) |
| R5 | 5'-CTAGTGGATCCG**ATAACTTCGTATAATGTATGCTATACGAAGTTAT**CCAAGCATCACCATCGACCCT-3' | (SEQ ID N° 5) |
| R6 | 5'-CTAGAGGGTCGATGGTGATGCTTGG**ATAACTTCGTATAGCATACATTATACGAAGTTAT**CGGATCCA-3' | (SEQ ID N° 6) |
| R7 | 5'-CTAGTCCAGATCTCACCATCGACC**CATAACTTCGTATAATGTATACTATACGAAGTTATT**-3' | (SEQ ID N° 7) |
| R8 | 5'-CTAGA**ATAACTTCGTATAGTATACATTATACGAAGTTAT**GGGTCGATGGTGAGATCTGGA-3' | (SEQ ID N° 8) |
| R9 | 5'-GGGGAATTCTTCTTGTACAGCTCGTCCA-3' | (SEQ ID N° 9) |
| R10 | 5'-GGGGAATTCCCATGGTGAGCAAGGGCGAGGAG-3' | (SEQ ID N° 10) |
| R11 | 5'-CTATCAGGGCGATGGCCCACTACGTGTTCTGAGGCGGAAAGAACCA-3' | (SEQ ID N° 11) |
| R12 | 5'-GGAATAGCTCAGAGGCCGAGGCGGCCTCGGCCTCTGCATAAATAAAA-3' | (SEQ ID N° 12) |

LoxP and lox511 sites are bold, point mutations in lox511 (oligos R3, R4, R7 and R8) are upper case, and restriction sites are underlined.

1.2. In Vitro Cre Reactions.

To perform Cre-mediated rearrangements in vitro, bacterial extracts containing an active Cre were prepared from *E. coli* 294-Cre strain 43. Cells were grown overnight at 37° C. in 500 ml LB medium, harvested by centrifugation, resuspended in 10 ml Cre Buffer (50 mM Tris/HCl pH 7.5, 33 mM NaCl, 10 mM $MgCl_2$, 5% glycerol, 0.02% $NaN_3$), and lysed by sonification. The soluble supernatant containing the Cre recombinase (Cre preparation) was recovered by centrifugation (14000×g, 15 min, 4° C.). The relevant plasmids (3 μg) were incubated with 100 μl of the Cre preparation for 1 hour at 37° C. For the control reactions, Cre was heat-inactivated by incubating the Cre preparation for 10 mm at 70° C. Plasmids were then isolated using the standard alkaline lysis method for DNA preparation (Ausubel et al., 1989). The recovered DNA was then used to transform competent XL1-Blue cells, which were grown overnight in 2 ml of LB at 37° C. Plasmids were isolated, digested by EcoRV and XbaI, separated on agarose gels and analyzed by Southern blotting using the radio-labelled oligos 5'-GTG-CATCTGCCAGTTTGAGG-3' (SEQ ID NO. 13) or 5'-AATACGACTCACTATAG-3' (SEQ ID NO. 14) recognizing lacZ sequence or T7 promoter, respectively.

1.3. Cell Culture, EGFP Detection and LacZ Staining.

COS-1 cells were cultured and transfected according to Bocquel et al. (1989). For each plasmid, five independent transfection experiments were done. After transfection, the cells were incubated at 37° C. for 72 h, and then fixed for 5 min with 2% formaldehyde in phosphate-buffered saline (PBS). For EGFP detection, cells were examined with a Leica MS FL-III stereo dissecting microscope equipped with epifluorescence optics, and digital images were generated using a Photometrics Coolsnap CCD camera. For β-galactosidase activity detection, cells were incubated overnight at 37° C. in staining solution (5 mM potassium ferricyanide, 5 mM potassium ferrocyanide, 2 mM $MgCl_2$, 1 mg/ml X-Gal) After washing with PBS, cells were post-fixed in 4% paraformaldehyde in PBS and digital images were generated using the Leica MS FL-III microscope.

1.4. Construction of Plasmid pγ6.0FlExβ-Gal (SEQ ID NO. 55).

To construct plasmid pγ6.0FlExβ-Gal, the RARγ exon 8 splice acceptor (oligos G3/G4; Table 2) was inserted by homologous recombination in *E. coil* into an XbaI digested pBluescript SK+ (Pharmacia) containing a loxP site (oligos G1/G2) in the sense orientation at its NotI site and from which the LacZ sequences were removed. After insertion of a 62 bp fragment (oligos G5/G6) into the XbaI site, the (NLS) β-gal pA cassette (Bonnerot et al., 1987) was introduced by homologous recombination in *E. coli*. A SnaBI and a lox511 site (oligos G7/G8) in the sense orientation was then introduced 5' of the loxP site into the SacII site. A second SnaBI site (oligo G9) was inserted into the BamHI site. An FRT site (oligos G10/G11) was inserted into the NotI site. The FRT/PGK/Neo/pA/FRT cassette was inserted into the XbaI site oligos G10/G11 giving rise to plasmid ploxP/lox511/lacZ/Neo. A loxP site was inserted in the sense orientation into the HpaI site of pSKγ6.0 (Lohnes et al., 1993) (oligos G12/G13). A lox511 site was introduced in the sense orientation into the 3' reconstructed HpaI site (oligos G14/G15). The EcoRI insert of this plasmid was ligated into a pGEX4T3 to obtain a LacZ sequence-deficient vector (pGEXγ6.0-loxP-lox511). The SnaBI fragment from plasmid plox P-lox511-lac2-Neo was isolated and inserted into the SfiI site of pGEXγ6.0/loxP/lox511 to obtain pγ6.0Flexβ-Gal (SEQ ID NO. 55).

TABLE 2

Sequences of primers used for construction of the pγ6.0FlExβ-Gal plasmid (SEQ ID N° 55).

| Name | Sequences | |
|---|---|---|
| G1 | 5'-GGCCGC**ATAACTTCGTATAATGTATGCTATACGAAGTTAT**-3' | (SEQ ID N° 15) |
| G2 | 5'-GGCC**ATAACTTCGTATGCATACATTATACGAAGTTAT**GC-3' | (SEQ ID N° 16) |
| G3 | 5'-**TATAATGTATGCTATACGAAGTTATT**CCTTGGCCTGGAATTTGCAGAATT-3' | (SEQ ID N° 17) |
| G4 | 5'-GCCCGGGGGATCCACTAGTTCTAGA**TGTCTCCACCGCTGAATGAAAAGCA**-3' | (SEQ ID N° 18) |
| G5 | 5'-CTAGTATGGATAAAGTTTTCCGGAATTCCGCTCTAGACTCATCAATGTTATCTTATCATGTCTA-3' | (SEQ ID N° 19) |
| G6 | 5'-CTAGTAGACATGATAAGATAACATTGATGAGTCTAGAGCGGAATTCCGGAAAACTTTATCCATA-3' | (SEQ ID N° 20) |
| G7 | 5'-GCTACGTA**ATAACTTCGTATAATGTATACTATACGAAGTTAT**GGGTCGATGGTGAGATCTCCGC-3' | (SEQ ID N° 21) |
| G8 | 5'-GGAGATCTCACCATCGACCC**ATAACTTCGTATAGTATACATTATACGAAGTTAT**TACGTAGCGC-3' | (SEQ ID N° 22) |
| G9 | 5'-GATCTTACGTAA-3' | (SEQ ID N° 23) |
| G10 | 3'-GGCCGG**GAAGTTCCTATTCTCTAGAAAGTATAGGAACTTC**CC-3' | (SEQ ID N° 24) |
| G11 | 5'-GGCCGG**GAAGTTCCTATACTTTCTAGAGAATAGGAACTTC**CC-3' | (SEQ ID N° 25) |
| G12 | 5'-AAG**ATAACTTCGTATAATGTATGCTATACGAAGTTAT**CCAAGCATCACCATCGACCCGTT-3' | (SEQ ID N° 26) |
| G13 | 5'-AACGGGTCGATGGTGATGCTTGG**ATAACTTCGTATAGCATACATTATACGAAGTTAT**CTT-3' | (SEQ ID N° 27) |
| G14 | 5'-AAGCCAAGCATCACCATCGAC**CCATAACTTCGTATAATGTATACTATACGAAGTTAT**GTT-3' | (SEQ ID N° 28) |
| G15 | 5'-AAC**ATAACTTCGTATAGTATACATTATACGAAGTTAT**GGGTCGATGGTGATGCTTGGCTT-3' | (SEQ ID N° 29) |

LoxP or lox511 sites are shown in bold. The point mutations are lower case. Restriction sites are underlined.

1.5. Generation of the Gene Trap Construct

To construct the plasmid pJMG (SEQ ID NO. 56), a PCR amplified PGK Neo cassette containing the OBS sequence and the synthetic splice donor site (SD; oligos J1/J2; Table 3) was introduced into the EcoRI site of pBluescript SK+ resulting in pJMG1. A cassette containing the FRT, loxP and lox511 sites was prepared by subsequent insertion of oligos J3 to J8 into a shuttle vector. This cassette was recovered by NruI and HindIII digest, repaired and introduced in front of the PGK-Neo gene of pJMG1. The lacZ sequence of the pBluescript SK+ was removed from pJMG1. A lox511 site (oligos J9/J10) and a FRTm site (oligos J11/J12) were subsequently introduced 3' to the synthetic splice donor site. The β-globin splice acceptor site (SA) followed by the IRES sequence were amplified by overlap extension PCR using oligos J13–J16. This fragment was introduced between the loxP site and the nls-LacZ polyA minigene of plasmid ploxP-nls-LacZ-pA. The obtained loxP-SD-IRES-nls-LacZ-pA DNA fragment was recovered and introduced, in anti-sense orientation at the BamHI site located in between the lox511 site and the PGK promoter to give to pJMG. The gene trap construct was excised from pJMG by NotI digestion and purification on a sucrose gradient.

TABLE 3

Sequences of primers used for construction of the plasmid pJMG.

| Name | Sequences | |
|---|---|---|
| J1 | 5'-ACTAGTGGATCCCCCGGGCTGCAGGAATTCTACCGGGTAGGGGAGGCGCTT-3' | (SEQ ID N° 30) |
| J2 | 5'-GTATCGATAAGCTTGATATCGCCGCTCGAGACTTACCTGACTGGCCGTCGTTTTACAGTCAGAAGAACTCGTCAAGAAG-3' | (SEQ ID N° 31) |
| J3 | 5'-CTCGCGAGGAATTCAACCAGAAGTTCCTATTCTCTAGAAAGTATAGGAACTTCCAGCT-3' | (SEQ ID N° 32) |
| J4 | 5'-GGAAGTTCCTATACTTTCTAGAGAATAGGAACTTCTGGTTGAATTCCTCGCGAGAGCT-3' | (SEQ ID N° 33) |
| J5 | 5'-AATGCCTACCGGACCATCATAACTTCGTATAATGTATACTATACGAAGTTATAAGCTTGCA-3' | (SEQ ID N° 34) |
| J6 | 5'-AGCTTATAACTTCGTATAGTATACATTATACGAAGTTATGATGGTCCGGTAGGCATTTGCA-3' | (SEQ ID N° 35) |
| J7 | 5'-GAGCTCATAACTTCGTATAATGTATGCTATACGAAGTTATCCAAGCATCACCATATGCA-3' | (SEQ ID N° 36) |

TABLE 3-continued

Sequences of primers used for construction of the plasmid pJMG.

| Name | Sequences | |
|---|---|---|
| J8 | 5'-TATGGTGATGCTTGGATAACTTCGTATAGCATACATTATACGAAGTTATGAGCTCTGCA-3' | (SEQ ID N° 37) |
| J9 | 5'-TCGACATAACTTCGTATAATGTATACTATACGAAGTTATAC-3' | (SEQ ID N° 38) |
| J10 | 5'-TCGAGTATAACTTCGTATAGTATACATTATACGAAGTTATG-3' | (SEQ ID N° 39) |
| J11 | 5'-TCGAAGAAGTTCCTAATCTATTTGAAGTATAGGAACTTCGCGGCCGCA-3' | (SEQ ID N° 40) |
| J12 | 5'-TCGATGCGGCCGCGAAGTTCCTATACTTCAAATAGATTAGGAACTTCT-3' | (SEQ ID N° 41) |
| J13 | 5'-CCGGTCCTTGGCCTGGAATTTGCACTCTGTTGACAACCATTGTCTCCT-3' | (SEQ ID N° 42) |
| J14 | 5'-GTAATACGACTCACTATAGGGAATTCCGCCCCTCTCCCTC-3' | (SEQ ID N° 43) |
| J15 | 5'-GAGGGAGAGGGGCGGAATTCCCTATAGTGAGTCGTATTAC-3' | (SEQ ID N° 44) |
| J16 | 5'-CTCCACCGCTGAATGAAAAGCAGCATGGTTGTGGCAAGCTTATCAT-3' | (SEQ ID N° 45) |

1.6. In Vitro Cre Reaction for Poly A Trap Experiments

To test for functionality of loxP and lox511 sites of pJMG, an in vitro Cre reaction was carried out (Schnütgen et al., 2001). Briefly, a crude extract of *E. coli* 294-Cre cells (Cre preparation; Buchholz et al., 1996) was incubated with 3 μg of the plasmids and the resulting DNA was transformed into *E. coli* DH5α and directly amplified in liquid medium. Amplified plasmid DNA was recovered and analysed by Southern blotting using the probe 5'-TAACAATTTCACA-CAGGA-3' (SEQ ID NO. 46), recognising the rabbit β-globin intron splice acceptor sequence (Green et al., 1988), to reveal the Cre-mediated rearranged constructs. To obtain the pJMG-f plasmid (FIG. 8B) pJMG was incubated for 5 min with the Cre preparation and transformed into *E. coli* DH5α. Individual clones were picked and analysed by restriction mapping and sequencing.

1.7. F9 Cell Culture

F9 cells were stably transfected with the NotI-excised fragment of pJMG-f, according to Taneja et al., (1995). 5–10×$10^6$ cells were trypsinised, washed, resuspended in 0.8 ml PBS and transferred into an electroporation cuvette. 10 μg of the purified DNA was added and cells were electroporated at 250 volts and 950° F. and seeded into 5 gelatinised 10 cm petri dishes. On the next day, 0.5 mg/ml G418 was added to the medium which was changed every 2 days for 14 days. 24 colonies were randomly chosen and amplified for further RNA isolation. The petri dishes from which the clones were chosen were subjected to X-Gal staining (Schnütgen et al., 2001).

1.8 RACE PCR

3' RACE was carried out as described by Frobman (1994). Briefly, a first RT-PCR was carried out using the oligonucleotides Qt (5'-CCAGTGAGCAGAGTGACGAGGACTC-GAGCTCAAGCT17-3') (SEQ ID N° 47) as anchor primer, as well as Q0 (5'-CCAGTGAGCAGAGTGACG-3') (SEQ ID N° 48) and Neo1 (3'-ACCGCTTCCTCGTGCTTTAC-3') (SEQ ID N° 49) for amplification. An aliquot of 1 μl of this reaction was used for a nested amplification using Q1 (5'-GAGGACTCGAGCTCAAGC-3') (SEQ ID N° 50) and Neo2 (5'-GCCTTCTTGACGAGTTCTTC-3') (SEQ ID N° 51) primers. The resulting PCR fragments were purified using the NucleoSpin kit (Macherey-Nagel) and sequenced using the Neo2 or OBS (5'-CTGTAAAACGACGGC-CAGTC-3') (SEQ ID N° 57) primers.

Example 1

In Vitro Site-specific Recombination

Figure 2:
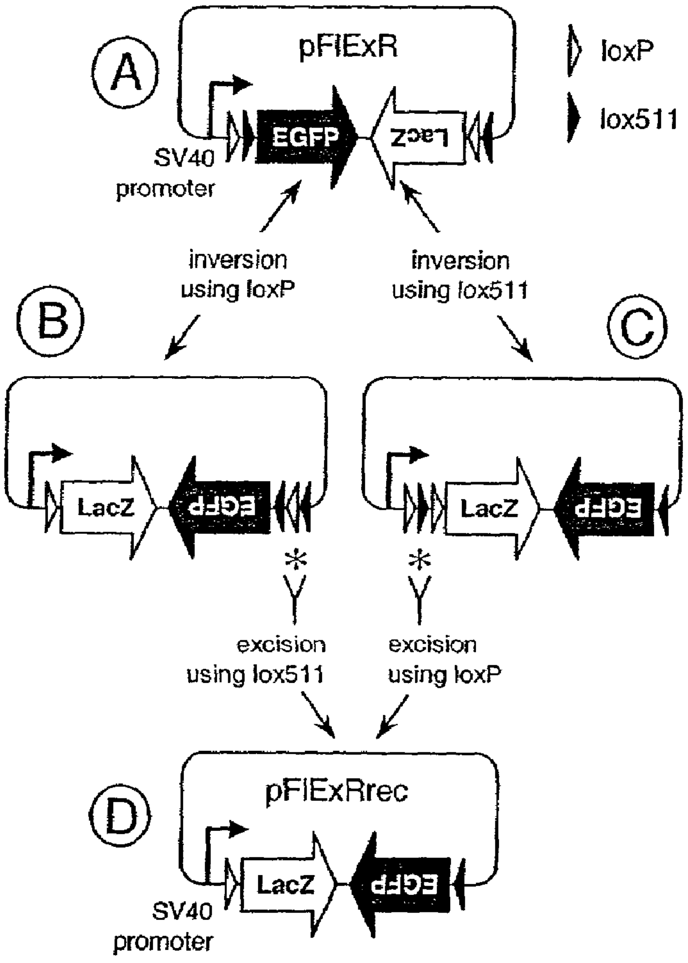
FIGS. 2A–D. Schematic representation of the construct pFlExR and of the expected plasmids after Cre-mediated rearrangement. (A) pFlExR (SEQ ID N.degree. 54) contains, in the following order, the SV40 promoter (broken arrow), a loxP site (open arrowhead), a lox511 site (closed arrowhead), the coding sequence for the enhanced-green fluorescent protein (EGFP) linked to a poly-adenylation signal, the .beta.-galactosidase promoter-less minigene (LacZ) in the antisense orientation, a loxP and a lox511 sites in inverted orientations. The SV40 promoter first drives the expression of EGFP. (B) Intermediate step after Cre-mediated inversion at the loxP sites. (C) Intermediate step after Cre-mediated inversion at the lox511 sites. (D) Final product after Cre-mediated excision between the two lox511 or the two loxP sites (asterisks). In this plasmid, SV40 promoter now drives beta-galactosidase expression. This reaction is not reversible, as the final plasmid contains single loxP and lox511 sites, which cannot recombine together.

The principle of the inventors' novel recombination strategy is illustrated in FIG. 1. pFlExR (SEQ ID NO. 54), a pSG5-based reporter plasmid was designed (FIG. 2) to test its feasability. It contains one pair of wild type loxP sites (open arrowheads), and one pair of lox511 sites (closed arrowheads), the loxP sites within each pair being oriented head to head. This organization (i.e. alternate loxP, lox511 and again loxP, lox511) is important. Both loxP and lox511 sites are recognized by Cre recombinase; however, they are "incompatible", as lox511 sites can efficiently recombine with themselves, but not with loxP sites (Hoess et al., 1986). Between the two sets of loxP-lox511 sites, the plasmid contains the coding region for the enhanced green-fluorescent protein (EGFP) in the sense orientation, and a promoter-less LacZ reporter gene in the antisense orientation. In this reporter plasmid, the SV40 promoter first directs expression of EGFP (FIG. 2A). Cre-mediated recombination may initially induce inversion of the intervening DNA at either the loxP sites (FIG. 23, open arrowheads), or the lox511 sites (FIG. 2B, closed arrowheads). Due to the reversibility of these reactions, an equilibrium between the states (A) and (B or C) is formed. However, inversion induces a direct repeat of either two lox511 sites (FIG. 2B; closed arrowheads) or two loxP sites (FIG. 2C; open arrowheads). A further Cre-mediated excision will then remove the DNA located (between the two loxP or between the two lox511 sites (FIG. 2B and C; asterisks). In the resulting plasmid (pFlExRrec), single loxP and lox511 sites are left, making further inversion of the intervening DNA impossible (FIG. 2D). The SV40 promoter now drives expression of LacZ, instead of EGFP.

Figure 3:
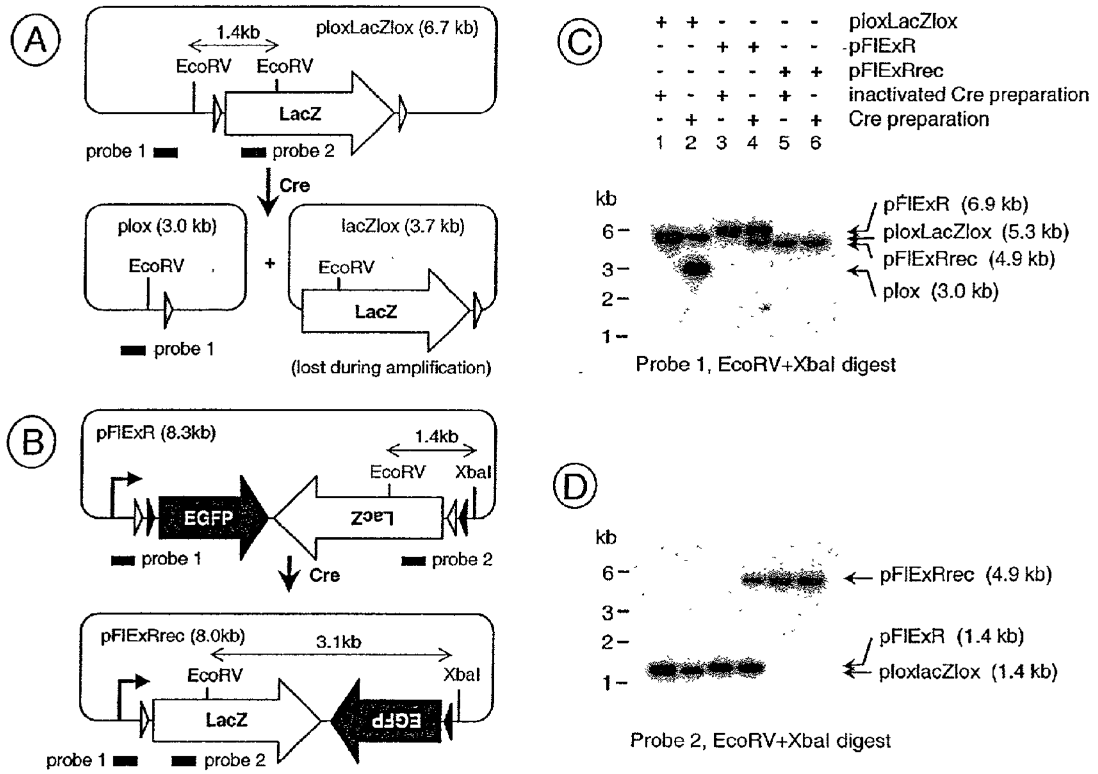
FIGS. 3A–D. In vitro Cre recombinase-mediated inversion/excision assay. (A) Schematic drawing of the ploxLacZlox construct used to check for Cre preparation efficiency before (upper panel) and after (lower panel) Cre-mediated recombination. EcoRV restriction sites and location of probes 1 and 2 are indicated. (B) Schematic drawing of pFlExR (SEQ ID N.degree. 54) before (upper panel) and after (lower panel, pFlExRrec) Cre-mediated recombination. EcoRV and XbaI restriction sites, together with location of probes 1 and 2 are indicated. (C) Evidence for Cre-mediated recombination by Southern blot analysis of plasmids digested with EcoRV and XbaI using probe 1. Lane 1 and 2, loxP-flanked LacZ plasmid (ploxLacZlox); lane 3 and 4, pFlExR; lane 5 and 6, pFlExRrec (inverted/excised pFlExR, see Materials and Methods). A crude Cre preparation was added in reactions illustrated in lanes 2, 4 and 6, whereas a heat-inactivated Cre preparation was added in reactions shown in lanes 1, 3 and 5. (D) Evidence for Cre-mediated recombination probing the same Southern blot as in (C) using probe 2 (for details see Materials and Methods). Note that the excised lacZlox fragment (3.7 kb), which does not contain plasmid sequences, was lost during amplification in bacteria. Open arrowhead, loxP site; closed arrowhead, lox511 site.

To test the feasibility of these Cre-mediated events, the inventors produced an *E. coli* extract containing a functional Cre recombinase (Cre preparation), and performed in vitro Cre-mediated rearrangements. The plasmids (FIGS. 3A and B) were incubated either with the Cre preparation (FIGS. 3C and D, lanes 2, 4 and 6), or with a heat-inactivated Cre preparation (FIGS. 3C and D, lanes 1, 3 and 5). They were digested with EcoRV and XbaI and analyzed by Southern blotting using probes 1 and 2 (see FIGS. 3A and B). To check the activity of the Cre preparation, a loxP-flanked LacZ sequence was used (plasmid ploxLacZlox, FIG. 3A). Cre recombinase mediated excision of the LacZ sequence, as assessed by the presence of the additional 3.0 kb EcoRV DNA fragment recognized by probe 1 (FIG. 3C, lane 2). Some unexcised plasmid was left (FIG. 3C, lane 2), most probably because of limiting-Cre activity, as increasing amounts of Cre preparation improved the yield of excision (data not shown). As expected, Cre recombinase mediated rearrangement in pFlExR (FIG. 3B), as assessed by the presence of the additional 4.9 kb EcoRV/XbaI DNA fragment recognized by probes 1 and 2 (FIGS. 3C and D, lane 4). The structure of the recombined plasmids was assessed by cloning in *E. coli*, followed by restriction mapping and sequencing of 20 individual colonies. All the recovered plasmids that were recombined underwent both inversion and excision (data not shown). The inverted/excised plasmid pFlExRrec (FIG. 3B; see also materials and methods) remained unchanged, when incubated in the presence of the Cre preparation (FIGS. 3C and D, compare lanes 5 and 6). As expected, this experiment indicates that Cre always mediated inversion and excision of the pFlExR construct in vitro, and that once rearrangement has taken place, it is irreversible.

Figure 4:
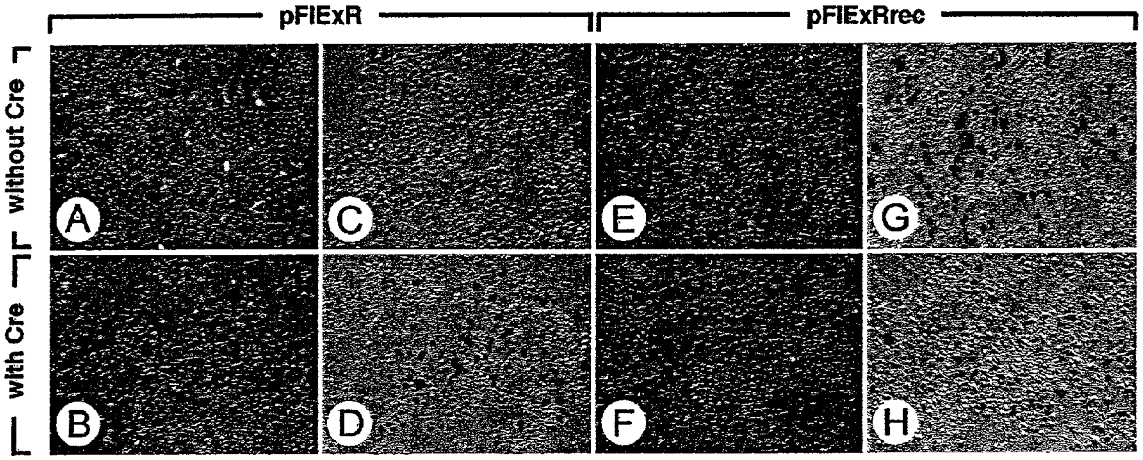
FIGS. 4A–H. In vivo Cre recombinase-mediated inversion/excision assay. COS-1 cells were transiently transfected with either pFlExR in absence (A and C) or in presence (B and D) of five fold excess pSG5-Cre, and transfected with pFlExRrec in absence (E and G) or in presence (F and H) of excess pSG5-Cre. Detection of EGFP was examined by fluorescence microscopy (A, B, E and F) and LacZ expression was assessed by light microscopy after X-Gal staining (C, D, G and H). Note that the background blue staining in FIG. 3C most probably reflects a low level of transcription of the beta-galactosidase minigene initiated from the non-coding strand of the pFlExR.

To demonstrate the feasibility of this new recombination system in eukaryotic cells, the inventors transiently transfected into COS-1 cells pFlExR or pFlExRrec either alone, or together with excess of pSG5-Cre (a Cre recombinase-expressing vector), and analysed these cells for either EGFP fluorescence or β-galactosidase activity. Those cells transfected with the pFlExR reporter plasmid alone showed clearly green fluorescence (FIG. 4A), but only faint β-galactosidase activity (FIG. 4C). In contrast, the cells transfected with the pFlExR reporter plasmid together with pSG5-Cre reproducibly showed no green fluorescence (FIG. 4B), but prominent beta-galactosidase activity (FIG. 4D), indicating that Cre always mediates consecutively inversion and excision in vivo. Cells transfected with pFlExRrec alone or together with pSG5-Cre showed no green fluorescence at all, but prominent β-galactosidase activity (FIGS. 4E and F), indicating that once inversion/excision has occurred, the DNA molecule remains stable in vivo. Altogether, these experiments clearly demonstrate that the Cre-mediated recombination strategy of the invention operates in vivo, at least in transiently transfected mammalian cells.

Example 2

In Vivo Site-specific Recombination in the Context of Normal Chromatin

Figure 5:
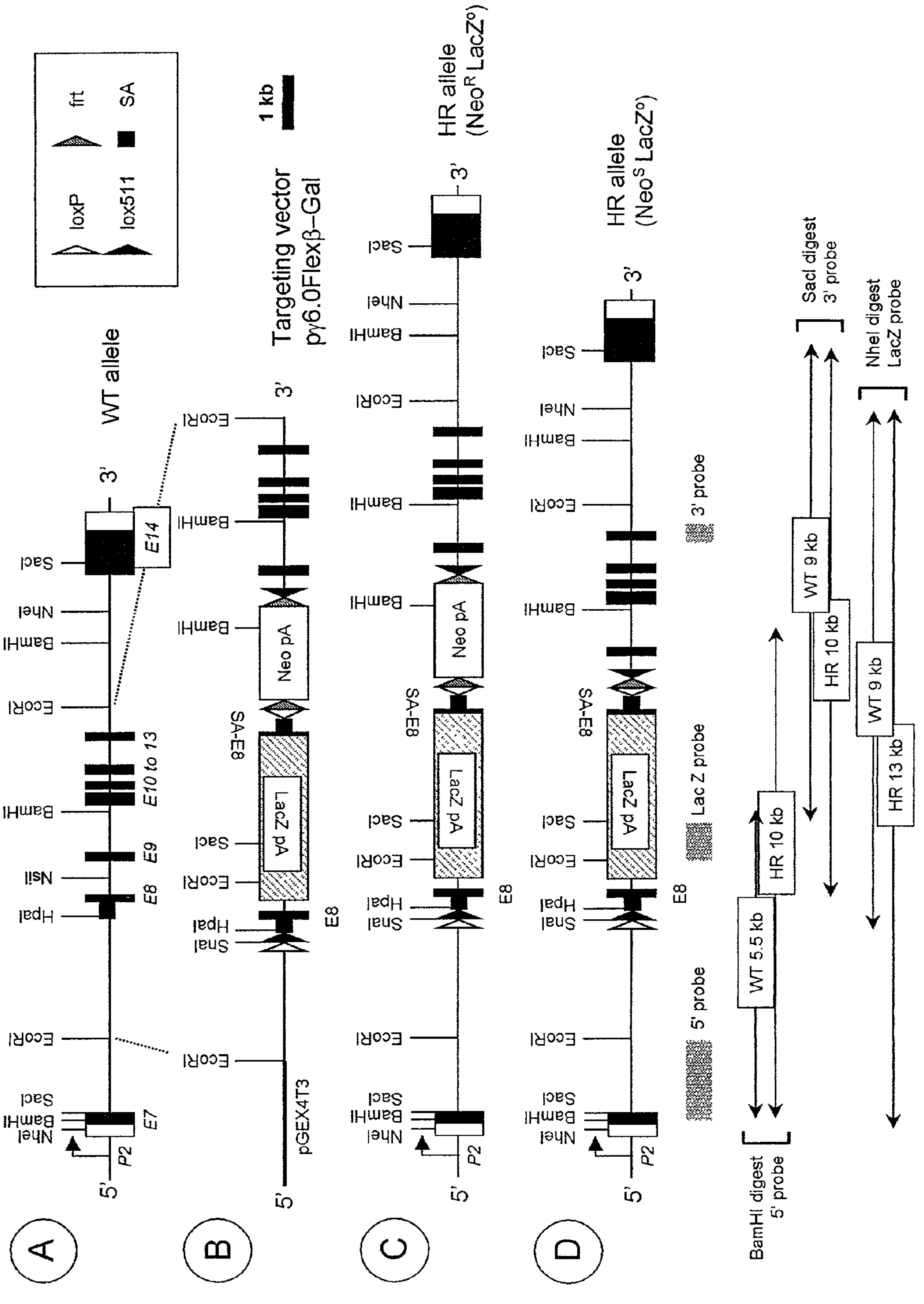
FIGS. 5A–D. Generation of a conditonal RAR.gamma. allele by homologous recombination. (A) Schematic drawing of the RAR.gamma. locus. Exons 7 to 14 are shown as solid boxes. As indicated, E7 is specific for RAR.gamma.-..sup.2, while E8 to E14 are common to all isoforms. The promoter (P2) is indicated by a broken arrow. 5' and 3' untranslated regions are shown as white boxes. Exon 8, whose splice acceptor is shown as waved lines, was chosen for the conditional disruption of RAR.gamma. (B) Structure of the targeting vector (p.gamma.6.0Flex.beta.-Gal) (SEQ ID N.degree. 55). (C) Structure of the recombinant allele following homologous recombination. (D) Structure of the recombinant allele after FLP-mediated removal of the selection cassette.
Figure 6:
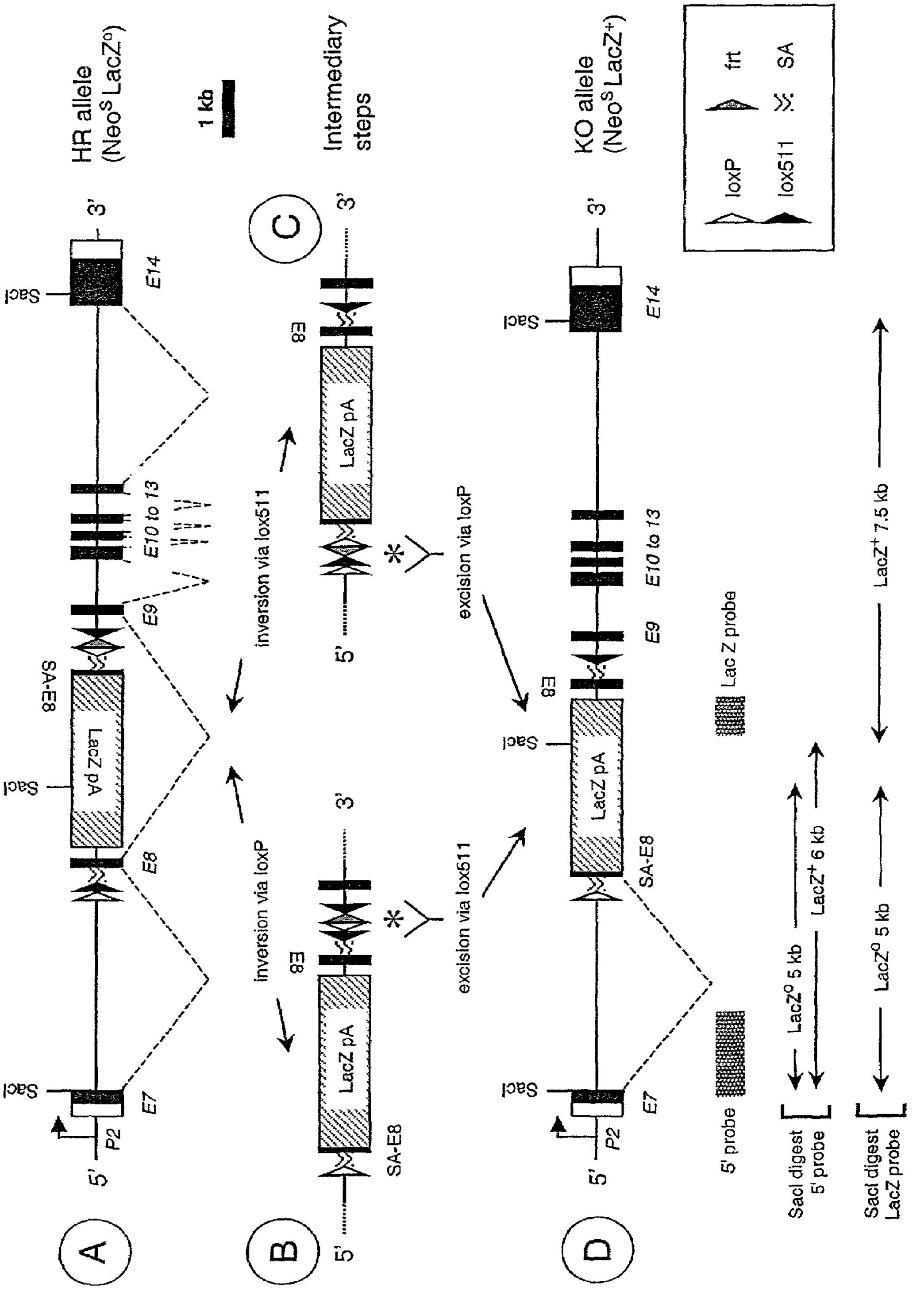
FIGS. 6A–D. Expected structures of the RAR.gamma. locus after Cre mediated recombination. (A) Structure of the modified RAR.gamma. locus, after FLP-mediated removal of the selection cassette. Dotted lines represent the expected splicing of the primary transcript. (B) Transient structure of RAR.gamma. locus of A after Cre-mediated inversion of the DNA fragment flanked by loxP sites. The asterisk points to the direct repeat of lox511 sites. (C) Transient structure of RAR.gamma. locus after Cre-mediated inversion of the DNA fragment flanked by lox511 sites. The asterisk points to the direct repeat of loxP sites. (D) Structure of RAR-.gamma. locus after Cre-mediated excision at the repeated lox sites (asterisks in B and C). Dotted lines represent the expected splicing of the primary transcript.

To develop the use of this system in living organisms, the inventors have demonstrated its functionality in the context of normal chromatin. To do this, the inventors carried out homologous recombination in ES cells, generating thereby a conditional knock-out linked to the expression of a β-galactosidase reporter gene in cells undergoing Cre-mediated recombination. The RARγ locus was chosen because: (i) its expression pattern is known (Ruberte et al., 1990); (ii) the phenotype of the knock-out is well characterised; and (iii) it is easy to target in ES cells, thus facilitating insertion of a heterologous fragment of more than 3 kb, as is required in the present method. The targeting vector used for homologous recombination (FIG. 5B) contained a 6 kb genomic fragment encompassing exons E8 to E13, in which were inserted: (i) a loxP and a lox511 in front of exon E8; (ii) a DNA module made of the natural splice acceptor of E8, the first 4 codons of E8 in frame with the NLS-LacZ-pA coding region, altogether in the antisense orientation; (iii) a loxP site in the reverse orientation, when compared to the first loxP site; (iv) a neomycin resistance (Neo) cassette; and (v) a lox511 site in the opposite orientation, when compared to the first lox511 site. The Neo cassette was flanked by FRT sites, thus allowing its excision using the FLP recombinase. The structures of the wild-type locus (A) and the recombined locus before (C; HR allele NeoR, LacZ−), and after removal of the selection cassette (D; HR allele NeoS, LacZ) are schematised in FIG. 5. Out of 234 surviving ES cell clones, 2 exhibited the expected restriction patterns for homologous recombination, as analysed by Southern blot (data not shown). Clone FK177 was injected into blastocysts, giving rise to 11 chimeras, out of which 2 transmitted the modified allele to their germline. FIG. 6 depicts the conditional RARγ allele (A), the intermediate steps (B) and (C) and the final structure of this locus after Cre treatment (D). Clone FK177 was transiently transfected with a Cre recombinase-expressing plasmid and analyzed by Southern blotting (data not shown). 2 clones were identified to be recombined (FK177.4 and FK177.18) Injection of these clones gave rise to 8 chimeric males and 1 chimeric female. Whereas the chimeric males were tested for germline transmission, the chimeric female was sampled and different organs were subjected to β-galactosidase stain. Organs that were known to express RARγ showed distinct blue staining (i.e. skin, bronchi, Harderian gland, tracheal rings; data not shown).

To further demonstrate that inversion and excision also occur in vivo, the mouse line FK177 has been crossed with a mouse strain expressing Cre recombinase very early during development (CMV-Cre). All the tissues known to express RARγ show blue straining (data not shown). Additionally, crosses with a mouse strain expressing Cre recombinase selectively in skin (K14-Cre) showed that inactivation of the RARγ gene and activation of the reporter Lac Z occurred in a conditional manner in epidermis only.

Cre recombinase can mediate inversion of any DNA fragment flanked by two loxP sites, which are in the opposite orientation. However, each DNA molecule continually undergoes rounds of recombination. In a living cell, this finally results in an equilibrium, with half of the loxP-flanked DNA being in the sense orientation, and the other half in the antisense orientation (Abremski et al., 1983). This technique was used by several groups to study particular genetic alterations in vivo, but its applications are limited (Lam et Rajewsky, 1998; Kano et al., 1998). One attempt to stabilize the intervening DNA in the inverted orientation has been made using modified loxP sites, which can efficiently undergo one round of recombination, but are impaired for the subsequent rounds. Nevertheless, this system cannot provide a tight control of recombination, due to the residual activity of these loxP sequences (Araki et al., 1997). Here the inventors have devised a novel approach to invert, upon Cre-mediated rearrangements, any DNA fragment in a stable, irreversible way. They have demonstrated the feasibility of this method by switching over irreversibly the transcription of the EGFP gene to the transcription of the lacZ gene, in transiently transfected COS cells.

Figure 7:
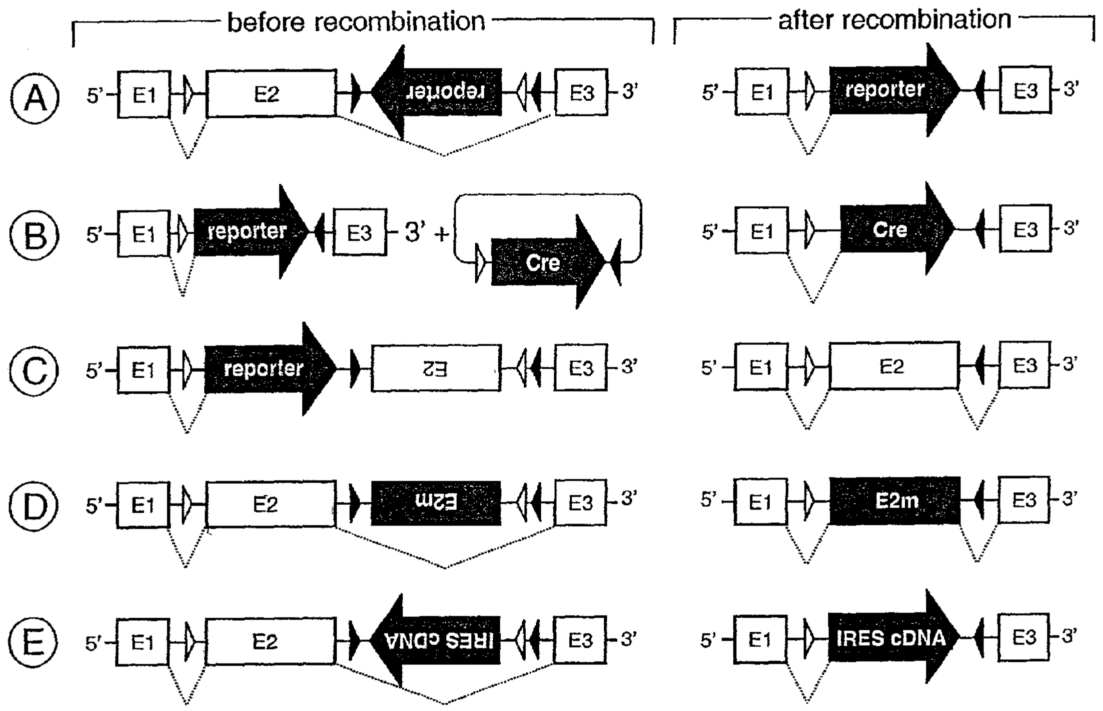
FIGS. 7A–E. Possible applications of the present invention. (A) Conditional knockout linked to simultaneous activation of a reporter. The scheme represents a conditional allele expressing the wild type protein (left side); upon Cre-mediated rearrangement (right side), exon 2 is removed and replaced by the reporter gene and its polyadenylation signal. Thus, replacement of the normal gene product by the reporter protein renders possible the direct identification of individual cells that underwent recombination (i.e. gene knockout). (B) Cassette exchange. The scheme represents a locus after Cre-mediated inversion/excision (left side). A further Cre-mediated rearrangement in the presence of a circular DNA containing a loxP-Cre-lox511 cassette (right side) leads to the exchange between the reporter and Cre genes. (C) Conditional rescue. The scheme represents a knock-in reporter allele (left side). After Cre-mediated rearrangement (right side), the reporter cassette is removed together with its polyadenylation signal, while the wild type exon is restored in the sense orientation. (D) Conditional point mutation. The scheme represents a conditional allele expressing the wild type protein (left side). Upon Cre-mediated rearrangement (right side), exon 2 is removed and replaced by mutated exon 2 (E2m), giving rise to the synthesis of a mutated protein. (E) Conditional gene replacement. The scheme represents a conditional allele expressing the wild type protein (left side). After Cre-mediated rearrangement (right side), exon 2 is removed and replaced by a cassette containing an internal ribosomal entry site (IRES) followed by a chosen cDNA and a polyadenylation signal. Synthesis of the wild type protein is abrogated, whereas the introduced cDNA is now expressed. Dotted lines represent the expected splicing of the primary transcript, and E1 to E3 stands for exons. Open and closed arrowheads represent loxP and lox511, respectively.

The power of recombinase-based strategies to achieve conditional genomic alterations relies upon a collection of particular transgenic mice, in which specific Cre expression patterns must be carefully evaluated. The existence of anti-Cre antibodies permits the detection of Cre protein by immunohistochemistry (Schwenk et al., 1997). However, functional characterization of Cre activity is the ultimate test for the suitability of a given transgenic line for its use in conditional knockout experiments. This is usually performed by using additional transgenic lines, in which Cre-mediated recombination is used to control the activity of a reporter gene in individual cells. Several such loxP-flanked lacZ or EGFP reporter lines have been generated (Akagi et al., 1997; Mao et al., 1999; Soriano et al., 1999; Kawamoto et al., 2000). However, the reporter genes may either be silent in a Cre-target tissue (Brocard et al., 1997), or occasionally lie in a chromatin configuration inaccessible to recombination by Cre, even if it is expressed (Kellendonk et al., 1999). To distinguish between the two possibilities accounting for the failure of a reporter gene to produce a functional protein (no transcription versus no recombination), dual reporter systems have been constructed (Lobe et al., 1999; Novak et al., 2000) (Z/AP or Z/EG mice). Such cassettes express the first reporter (lacZ), or the second one (alkaline phosphatase or EGFP), or none of them, depending on whether the cassette is transcribed but not recombined, transcribed and recombined, or untranscribed, respectively. Although attractive, these strategies require multiple time-consuming animal breedings to obtain, within a single mouse, the desired constellation of transgenes (e.g. the Cre, the reporter, the loxP-flanked alleles . . . ). Furthermore, the Cre-mediated recombination frequency may vary between genomic target locations. Thus, the excision pattern for a conditional allele cannot be accurately inferred from that of a reporter gene. There is an obvious need for a direct approach that allows one to identify individual cells recombined at a given gene locus. Applied to gene targeting in ES cells, the present method should result in conditional knockout mice, in which Cre-mediated recombination at a given locus will be necessarily associated with expression of a reporter gene (FIG. 7A). This will allow easy detection of individual cells that have undergone Cre-mediated recombination (i.e. replacement of the normal gene product by the reporter protein gene, in other words a gene knockout/knock-in of the reporter gene).

The inventors' approach has also been tested in the context of normal chromatin environment. However, to generate conditional genetic alterations, care has to be taken during vector design that the distance between the compatible loxP sites, once inversion has taken place (asterisks, FIGS. 2B and C), allows excision, i.e. at least 82-bp using Cre/loxP (Hœss et al., 1985). Additionally, one should keep in mind that modifying the genome of eukaryotic cells in such a way may have some drawbacks. The presence of prokaryotic sequences in the antisense orientation (e.g. lacZ reporter gene) carries the risk of gene silencing (Cohen-Tannoudji et al., 2000). The repeat of an endogenous splicing site, and possibly of a poly-adenylation signal in the antisense orientation, may induce the occurrence of aberrantly spliced or poly-adenylated mRNA. In fact, this may not be a problem as antiparallel coupling of two genes (i.e. overlap of two genes transcribed in opposite orientations) has been shown to occur in mammalian cells; in the case of the overlapping thyroid hormone receptor alpha and Rev-erbA alpha genes, aberrant splicing or polyadenylation of mRNA have not been reported (Chawla et Lazar, 1993). In any case, DNA repeats, which are unavoidable, should be reduced as much as possible. The occurrence and frequency of such drawbacks will have to be directly estimated by further studies.

It is known that Cre recombinase can mediate exchange of a loxP-flanked genomic fragment by any other loxP-flanked DNA present in a circular vector, promoting consistent insertion of different exogenous sequences into the same locus of the genome (cassette exchange) (Araki et al., 1999; Feng et al., 1999). If one applies the present method to gene targeting in ES cells, firstly single loxP and lox511 sites would be left in the gene upon Cre-mediated inversion/excision, but the most attractive feature is that this loxP/lox511-flanked fragment would stay in position, even when an active Cre recombinase remains in the cells. Therefore, it becomes possible to integrate, by cassette exchange, the gene for Cre recombinase itself into the targeted locus of the genome ("easier knock-in", because exchange occurs in 50% of the cells expressing Cre) (Feng et al., 1999), expanding the collection of lineage/cell-type specific Cre-expressing mouse lines and circumventing time-consuming experiments such as transgenesis (FIG. 7B). Using the present strategy to target a given gene in ES cells would then provide, at once, a conditional knockout, a reporter for monitoring excision at the locus, and a target for multiple knock-in using Cre-directed cassette exchange. Finally, the invention should also allow more sophisticated genetic rearrangements to be done, namely those genetic alterations that are considered "impossible" to achieve (Nagy et al., 2000): (i) accurate conditional rescue of a gene knockout (FIG. 7C), (ii) conditional point-mutations (FIG. 7D), and (iii) conditional replacement of a given gene product by another one (FIG. 7E).

Example 3

Generation of Conditional Reporter Alleles by Trapping Genes in ES Cells Using a poly-A Trap Approach To date, only a few reporter lines have been described (Akagi et al., 1997; Lobe et al., 1999; Mao et al., 1999; Soriano, 1999; Kawamoto et al., 2000; Novak et al., 2000), which are not always functional in all tissues. The method of the invention proposed in Example 2 provides a reporter allele directly at the Cre-inactivated locus. However, it needs to be done for each individual locus, a procedure which requires time-consuming homologous recombination experiments. Gene traps provide a general strategy to target any gene locus in a given cell type, among which one can choose genes exhibiting discrete patterns of expression during either development or differentiation (Hill et al., 1993; Friedrich et al., 1993). The vectors used to date can be divided into two main classes: (i) Vectors that trap genes active in the chosen cell line, using a promoterless Neo as a selectable marker. Thus, they require an integration into a transcriptionally active gene to provide resistance to the selective drug G418. (ii) Vectors in which the selectable Neo is under the control of its own promoter (Skarnes et al., 1992; Salminen et al., 1998) lacking its poly A signal but instead containing a splice donor site. They require an integration in front of a poly A signal from the mouse genome to produce a stable mRNA (Niwa et al., 1993). These latter vectors permit the trapping of all genes, whether they are active or inactive in the given cell line.

The inventors disclose a new system to generate cells harbouring a conditional reporter allele knocked-into endogeneous genes by combining a poly A trap-based method with the Cre/loxP-lox511 method (Schnütgen et al., 2001). The rapid amplification of cDNA ends (RACE) allows one to search databanks and, thereby to identify the trapped gene. When applied to embryonic stem cells, injection of the gene-trapped clones into blastocysts may provide a library of conditional reporter mouse lines for analysis of Cre-mediated recombination patterns. Furthermore, recombinase-mediated cassette exchange (RCME) will make it possible to generate a library of mouse strains harbouring any other conditional construct at the trapped loci, including the Cre gene itself. This approach will allow a large-scale screen of gene-trapped containing clones, which may be used for the generation of a zoo of mouse lines expressing Cre (or FLP recombinase) in any given tissue or cell type.

Figure 8:
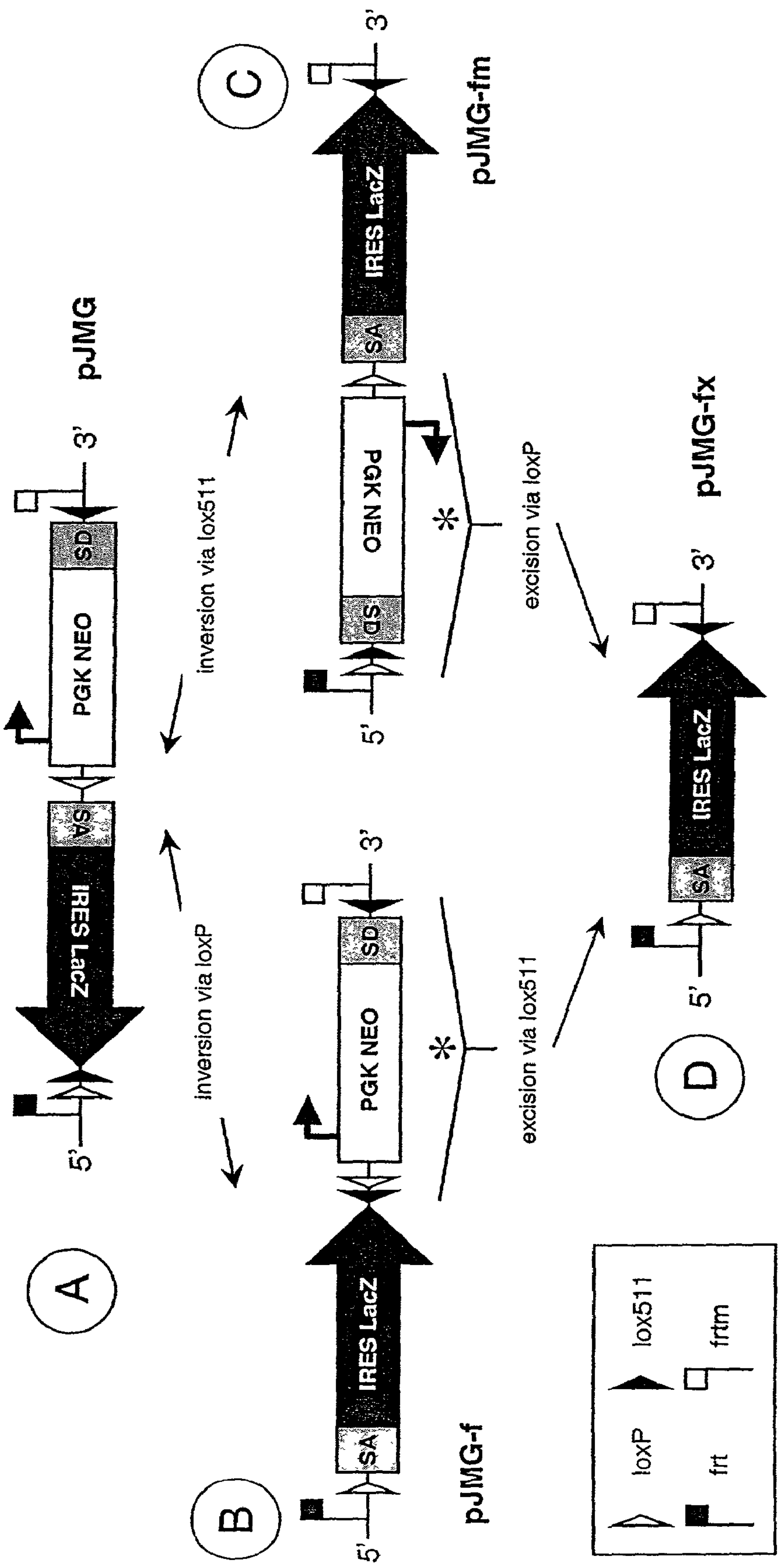
FIGS. 8A–D. Description of the construct pJMG and the expected variants after Cre-mediated rearrangement. (A) Schematic drawing of pJMG which contains, in the following order, an FRT site (closed flag), a loxP site (open arrowhead), a lox511 site (closed arrowhead), a DNA cassette consisting of the rabbit .beta.-globin intron splice acceptor site (SA), an IRES sequence linked to the promoter-less nls-.beta.-galactosidase mini gene (LacZ) and a loxP site in antisense orientation, a PGK promoter (broken arrow) driving expression of the neomycin phosphotransferase coding sequence (Neo) linked to the OBS sequence and a synthetic splice donor (SD), a lox511 site and a mutated FRT site (FRTm; open flag) in antisense orientation. (B) Intermediate step after Cre-mediated inversion at the loxP sites. (C) Intermediate step after Cre-mediated inversion at the lox511 sites. (D) Final product after Cre-mediated excision between the two lox511 or the two loxP sites (asterisks), removing the PGK Neo Cassette. This reaction is not reversible, as the final plasmid contains single loxP and lox511 sites, which cannot recombine together.

The gene trap construct is schematised in FIG. 8. It is made of two DNA fragments of which the first one contains the conditional reporter cassette (LacZ), whereas the second one contains the poly-A based gene trap elements (FIG. 8A). In detail, the reporter cassette is in the antisense orientation and contains the splice acceptor site from the rabbit β-globin intron (SA) linked to an internal ribosomal entry site (IRES) and the nls-LacZ cDNA followed by a polyadenylation signal (Bonnerot et al., 1987). This fragment is flanked on the 5' side with a loxP and a lox511 sequence in the sense orientation, and on the 3' side with a loxP sequence in the antisense orientation. The gene trap cassette contains a phosphoglycerate kinase (PGK) promoter driving expression of a neomycin phosphotransferase (Neo) cDNA linked to a synthetic splice donor site (SD; Zambrowicz et al., 1998). This fragment is followed by a lox511 site in the antisense orientation. Cre-mediated recombination may initially induce the inversion of the intervening DNA at either the loxP sites (FIG. 8B) or the lox511 sites (FIG. 8C). Both reactions lead to constructs in which either the lox511 sites (FIG. 8B, asterisks) or the loxP sites (FIG. 8C, asterisks) form a direct repeat, allowing Cre recombinase to mediate excision (FIG. 8D). To further allow recombinase-mediated cassette exchange (RCME) according to Schlake et al. (1994) at the trapped loci, the whole construct is flanked by a wild type FRT sequence on its 5' side and a mutated FRT (FRTm) sequence on its 3' side.

Figure 9:
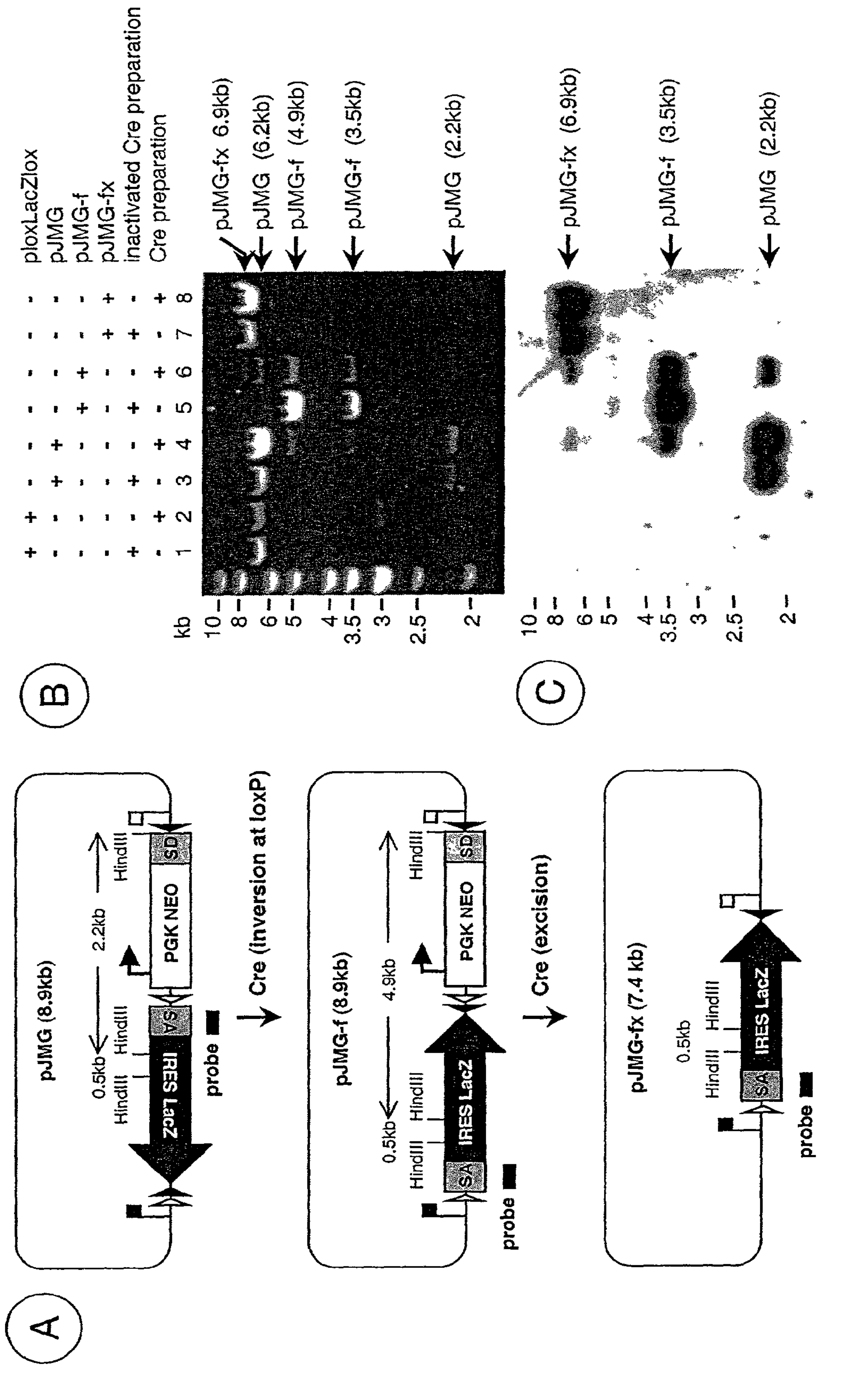
FIGS. 9A–C. In vitro Cre recombinase-mediated inversion/excision assay on plasmid pJMG (SEQ ID N.degree. 56). (A) Schematic drawing of pJMG (upper panel), the intermediate construct pJMG-f (middle panel) and the final construct pJMG-fx (lower panel). HindIII restriction sites, together with the location of the probe are indicated. (B) Evidence for Cre-mediated recombination assessed by ethidium bromide stained agarose gel analysis of HindIII digested plasmids. Lane 1 and 2, loxP-flanked LacZ plasmid (ploxLacZlox); lane 3 and 4, pJMG; lane 5 and 6, pJMF-f (inverted pJMG, see Materials and Methods); lane 7 and 8, pJMG-fx (inverted and excised pJMG, see Materials and Methods). A Cre preparation was added in the reactions illustrated in lanes 2, 4, 6 and 8, whereas a heat-inactivated Cre preparation was added in the reactions shown in lanes 1, 3, 5 and 7. The sizes of the expected HindIII fragments are indicated on the right. (C) Evidence for Cre-mediated recombination assessed by Southern blot using a probe recognizing the rabbit beta-globin splice acceptor site (for details see Materials and Methods) Note that this probe does not hybridise to the ploxLacZlox. Open arrowhead, loxP site; closed arrowhead, lox511 site; closed flag, FRT site; open flag, FRTm site, SD, synthetic splice donor.

To test the construct for feasability of Cre-mediated rearrangements, an in vitro Cre reaction was carried out following Schnütgen et al. (2001). The plasmids (FIG. 9A) were incubated either with the Cre preparation (FIG. 9B; lanes 2, 4, 6 and 8) or with a heat-inactivated Cre preparation (FIG. 9B; lanes 1, 3, 5 and 7; see Materials and Methods). They were digested with HindIII and analysed by Southern blotting using a probe located in the rabbit β-globin splice acceptor site (FIG. 9A). To check the activity of the Cre preparation, a loxP-flanked LacZ containing plasmid (FIG. 9B; ploxlacZlox) was used (see also Schnütgen et al., 2001). As expected, Cre recombinase mediated rearrangement in pJMG (FIG. 9A) to produce the intermediate (pJMG-f), as assessed by the presence of the additional 4.9 kb and 3.5 kb HindIII fragments (FIGS. 9B and C, lane 4). The other intermediate (pJMG-fm) cannot be distinguished from pJMG using this digest. However, it was also evidenced using another restriction mapping (data not shown). Cre recombinase also mediated excision of the inverted plasmids to produce pJMG-fx, as assessed by the presence of the 6.9 kb HindIII fragment (FIGS. 9B and C; lanes 4). The structure of the recombined plasmids was assessed by cloning in *E. coli*, followed by restriction mapping and sequencing. Additionally, upon Cre-mediated recombination, intermediate plasmid pJMG-f (and pJMG-fm; data not shown) was not only reverted to pJMG, as assessed by the presence of the 2.2 kb HindIII fragment, but also excised to produce pJMG-fx (FIGS. 9B and C, lane 6). Some unexcised plasmids were left in lanes 2, 4 and 6, most probably because of limiting Cre activity, as increasing amounts of Cre preparation improved the yield of excision (data not shown). The plasmid pJMG-fx cannot undergo any recombination event (FIGS. 9B and C, lane 8), as was demonstrated (Schnütgen et al., 2001).

Figure 10:
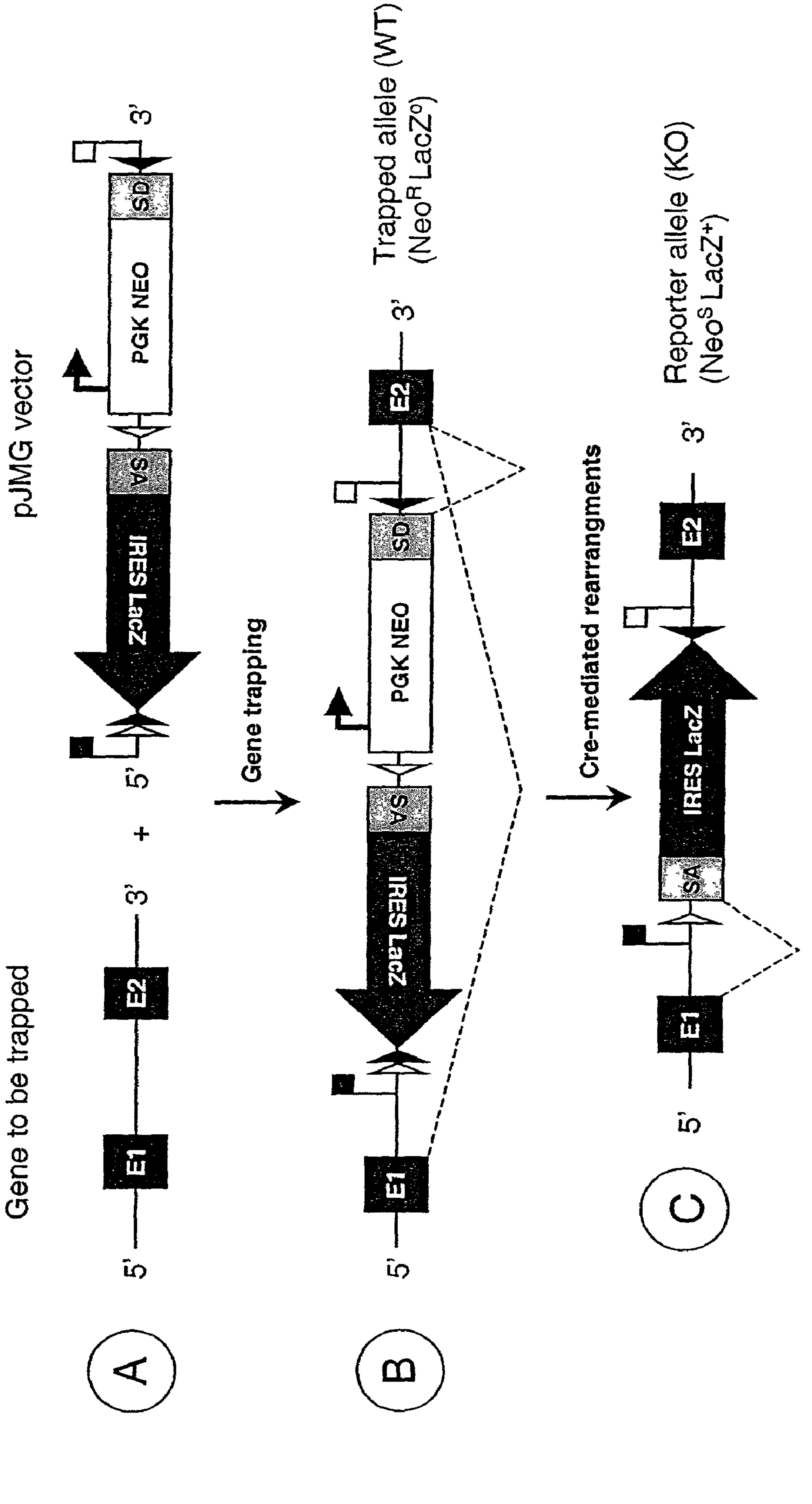
FIGS. 10A–D. Scheme of the gene trap strategy. Upon insertion of the pJMG vector into an intron of a transcribed locus, transcription of the trapped gene should not be affected (Trapped allele, WT). The PGK promoter drives the expression of the NEO cassette linked to the 3' part of the trapped gene that provides the poly-A signal necessary to produce a stable mRNA. The cell is thus resistant to G418 selection (NeoR), whereas the LacZ gene is silent (LacZ0). Upon Cre-mediated recombination, the Neo gene is removed and LacZ is inverted. The cell becomes sensitive to G418 selection (NeoS), whereas the LacZ gene is expressed under the control of the trapped promoter (LacZ+). Dotted lines represent the expected splicing of the primary transcript; E1 and E2 stands for exons 1 and 2; SA indicates rabbit .beta.-globin splice acceptor site; IRES stands for internal ribosomal entry site. Open and closed arrowheads represent loxP and lox511 sites, respectively. Closed and open flags represent FRT and mutated FRT sites, respectively, SD, synthetic splice donor.

The inventors anticipated that random integration of the NotI-excised fragment of pJMG into the genome would lead to expression of a stable mRNA encoding for Neo phosphotransferase only upon trapping of a gene that provide a polyadenylation sequence. Using this strategy, a gene does not need to be transcribed to be trapped. Furthermore, the sequence of the trapped gene can be easily identified by rapid amplification of cDNA ends (3'-RACE; Frohman, 1988). The sequence of the fusion transcript is likely to contain coding regions, allowing identification of the trapped gene in database searches. At the trapped locus, the wildtype mRNA should still be expressed, as the splice acceptor site which is in the antisense orientation, should not interfere with normal transcription of the gene (FIG. 10B). After Cre-mediated recombination the endogeneous promoter of the trapped gene will drive the expression of the LacZ reporter (FIG. 10C). Additionally, due to the presence of the LacZ cassette in the sense orientation, the 3' end of the endogenous trapped message will be replaced by the IRES-LacZ sequence. Thus, expression of the trapped gene is likely to be abrogated, or at least its gene product will be truncated.

Figure 11:
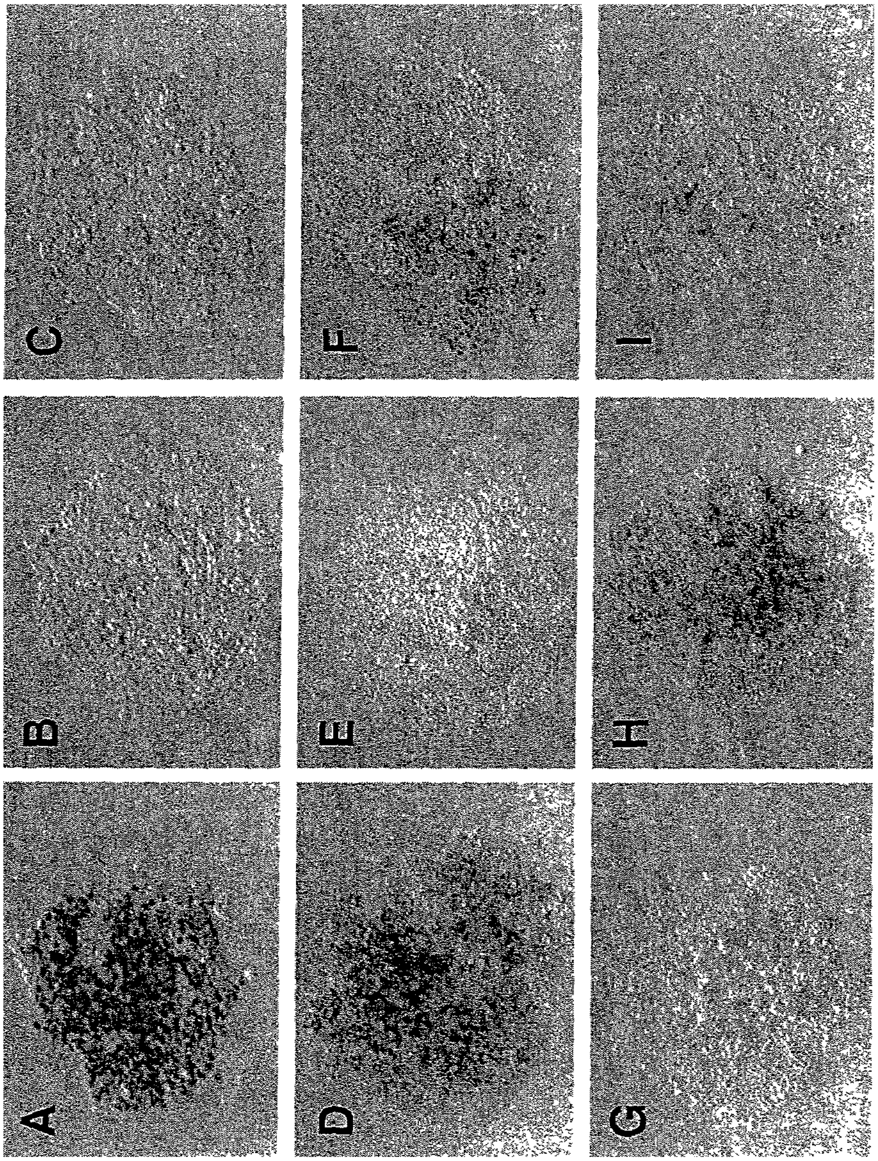
FIGS. 11A–I. In vivo assay to test for functionality of the splice acceptor-IRES LacZ cassette and/or the polyA trap based method in F9 cells. F9 cells were stably transfected with the NotI fragment of pJMG-f, selected against G418 for 12 days and subjected to X-gal staining. As expected, neomycin resistant clones were obtained, out of which some of them expressed lacZ. Panels A-1 depict individual clones showing varying degrees of activity.

To test for functionality of the splice acceptor site as well as of the IRES and LacZ sequences, the NotI fragment from the intermediate plasmid pJMG-f, which contains the LacZ cassette in the sense orientation (FIG. 8B; see also Materials and Methods) was used for electroporation of F9 cells. After selection with G418, F9 clones were selected and tested for LacZ expression (FIGS. 11A to I). As expected, each clone exhibited a different lacZ expression pattern reflecting the activity of the trapped gene in F9 cells, ranging from no expression at all (FIGS. 11 C,E,G) to strong expression (FIG. 11A). Twenty-four clones were randomly picked and amplified for RNA isolation. Two of them were subsequently used for 3' RACE-PCR analysis. In clone 21 the early transposon Etn (accession number AB033515) was trapped, whereas in clone 24 the locus RPCI-23-70D11 (accession number AZ235091) was trapped. This experiment demonstrated (i) the functionality of the synthetic splice donor site downstream of Neo, that can splice into an endogeneous poly-A signal, as Neo resistant clones were obtained; (ii) the functionality of the rabbit β-globin splice acceptor site and of the IRES-LacZ fusion, as blue clones were obtained, independently of G418 resistance. This clearly indicates that unexpressed genes were efficiently trapped; (iii) identification of the trapped loci can be easily performed by 3' RACE PCR.

Gene trapping was then performed in mouse embryonic stem cells which were electroporated with the NotI fragment of pJMG and selected against G418 for 2 weeks. One hundred resistant clones were amplified and frozen. DNA was isolated for analysis of multi-sites targeting. RNA isolation and RACE-PCR analysis was done, and three clones have been chosen to be injected into mouse blastocysts.

Figure 12:
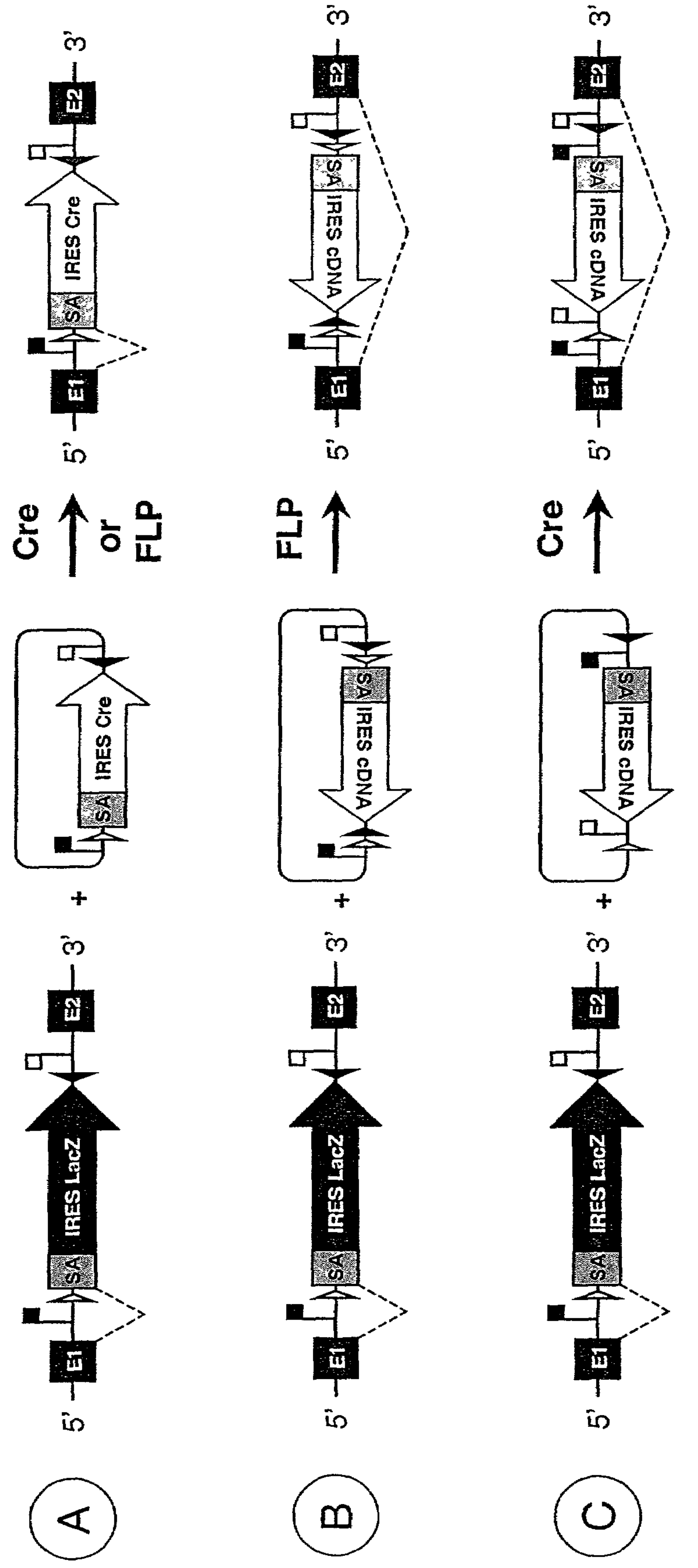
FIGS. 12A–I. Possible applications using recombinase mediated cassette exchange. (A) The scheme represents a trapped genetic locus after Cre-mediated inversion/excision (left side). The LacZ reporter is expressed under the control of the trapped gene promoter. A further Cre- or FLP-mediated rearrangement, in the presence of a circular DNA containing a Cre cassette flanked with appropriate recombinases specific target sites, leads to the exchange between the reporter and Cre (right side). Then Cre is expressed under the control of the trapped gene promoter. (B) The scheme represents a trapped genetic locus after Cre-mediated inversion/excision (left side). A further FLP-mediated recombination in the presence of a circular DNA containing a cDNA cassette flanked with a FRT sequence on its 5' side and of a FRTm sequence on its 3' side leads to the exchange between the reporter and cDNA (right side). As the cDNA is itself flanked by two pairs of loxP and lox511 sites, expression of the cDNA depends on the presence of Cre (conditional allele upon Cre-mediated recombination). (C) The scheme represents a trapped genetic locus after Cre-mediated inversion/excision (left side). A further Cre-mediated recombination in the presence of a circular DNA containing a cDNA cassette flanked with a loxP sequence on its 5' side and of a lox511 sequence on its 3' side leads to the exchange between the reporter and cDNA (right side). As the cDNA is itself flanked by a FRT sequence on its 5' side and of a FRTm sequence on its 3' side, expression of the cDNA depends on the presence of FLP (conditional allele upon FLP-mediated recombination). Dotted lines represent the expected splicing of the primary transcript; E1 and E2 stand for exons 1 and 2; SA indicates rabbit .beta.-globin splice acceptor site; IRES stands for internal ribosomal entry site. Open and closed arrowheads represent loxP and lox511 sites, respectively. Closed and open flags represent FRT and FRTm sites, respectively.

The inventors devised a novel approach to generate conditional reporters by trapping genes in cells. they make use of the poly-A trap based method rather than the use of promoter-based trap methods as, in the latter case, only expressed genes are trapped. Indeed, using the poly-A based trap method the inventors may target genes which are not expressed in ES cells, but which are expressed later in a tissue- or cell-specific manner, not only during early development but also in the adult mouse. The loxP and lox511 sites may allow Cre-mediated RCME, to replace the reporter cassette by another one. In this approach, the addition of two incompatible FLP recombinase recognition sites (FRT and FRTm) may allow a subsequent FLP-mediated RCME (FIG. 12A). The inventors may use this system to generate a number of mouse lines, expressing for example the inducible recombinase $CreER^T$ under the control of the trapped promoters. Furthermore, RCME using FLP may allow the inventors to insert at the trapped locus a conditional allele for Cre (FIG. 12B); whereas RCME using Cre may allow the inventors to reintroduce at the trapped locus a conditional allele for FLP (FIG. 12C).

The present application of the invention in gene trapping furnishes a highly powerful system that allows (i) generation of conditional reporter alleles at any gene locus; (ii) possibly generation of conditional knock-out alleles and (iii) generation of targets for RCME via Cre or FLP recombinases to produce a library of Cre- or FLP-expressing lines (a Cre- or a FLP-Zoo) or to insert conditional alleles for Cre or FLP.

REFERENCES

Abremski et al. (1983) Cell 32:1301–1311.
Abremski et al. (1984) J. Biol. Chem. 259:1509–1514.
Abremski et al. (1986) J. Biol. Chem. 261:391–396.
Akagi et al. (1997) Nucl. Acids Res. 25:1766–1773.
Araki et al. (1992) J. Mol. Biol. 225:25–37.
Araki et al. (1999) Cell Mol. Biol. 45:737–750.
Argos et al. (1986) EMBO J. 5:433–440.
Ausubel et al. (1989) Current Protocols in Molecular Biology, Wiley Interscience, New York.
Bocquel et al. (1989) Nucl. Acids Res. 17:2581–2595.
Bonnerot et al. (1987) Proc. Natl. Acad. Sci. USA 84:6795–6799.
Broach et al. (1982) Cell 29:227–234.
Brocard et al. (1997) Proc. Natl. Acad. Sci. USA 94:14559–14563.
Buchholz et al. (1996) Nucl. Acids Res. 24:3118–3119.
Campbell (1992), J. Bacteriol. 174:7495–7499.
Capecchi (1989) Science 244:1288–1292.
Chawla et al. (1993) J. Biol. Chem. 268:16265–16269.
Cohen-Tannoudji et al. (2000) Transgenic Res. 9: 233–235.
Copp et al. (1995) Trends Genet. 11:87–93.
Danielan et al. (1998) Curr. Biol. 8:1323–1326.
Feil et al. (1996) Proc. Natl. Acad. Sci USA 93:10887–10890.
Feil et al. (1997) Biochem. Biophys. Res. Commun. 237: 752–757.
Feng et al. (1999) J. Mol. Biol. 292:779–785.
Friedrich et al. (1993) Meth. Enzymol. 225:681–701.
Frohman (1994) PCR Methods Appl. 4:S40-S58.
Green et al. (1988) Nucl. Acids Res. 16:369.
Gu et al. (1993) Cell 73:1155–1164.
Hasan et al. (1987) Gene 56:145–151.
Hill et al. (1993) Meth. Enzymol. 225:664–681.
Hœss et al. (1985) Gene 40:325–329.
Hœss et al. (1986) Nucl. Acids Res. 14:2287–2300.
Hœss et al. (1990) Eckstein and Lilley, Berlin-Heidelberg, Springer-Verlag 4:90–109.
Indra et al. (1999) Nucl. Acid. Res. 27:4324–4327.
Kano et al. (1998) Biochem. Biophys. Res. Com. 248: 806–811.
Kawamoto et al. (2000) FEBS Lett. 470:263–268 (2000).
Kellendonk et al. (1996) Nucl. Acids Res. 24:1404–1411.
Kellendonk et al. (1999) J. Mol. Biol. 285:175–182.
Kœtsier et al. (1996) Transgenic Res. 5:235–244.
Lam et al. (1998) Proc. Natl. Acad. Sci. USA 95:13171–13175.
Landy (1993) Current Opinions in Genetics and Devel. 3:699–707.
Lee et al. (1998) Gene 216:55–65.
Li et al. (2000) Nature 407:633–636.
Lobe et al. (1999) Dev. Biol. 208:281–292.
Logie et al. (1995) Proc. Natl. Acad. Sci. USA 92: 5940–5944.
Lohnes et al. (1993) Cell 73:643–658.
Maeser et al. (1991) Mol. Gen. Genet. 230:170–176.
Mao et al. (1999) Proc. Natl. Acad. Sci. USA 96:5037–5042.
Metzger et al. (1995) Proc. Natl. Acad. Sci. USA 92:6991–6995.
Nagy (2000) Genesis 26:99–109.
Niwa et al. (1993) J. Biochem (Tokyo) 113:343–349.
Novak et al. (2000) Genesis. 281:147–155.
O'Gorman et al. (1991) Science 251:1351–1355.
Orban et al. (1992) Proc. Natl. Acad. Sci. USA 89:6861–6865.
Posfai et al. (1994) Nucl. Acids Res. 22:2392–2398.

Qian et al. (1992) J. Biol. 267:7794–7805.

Ruberte et al. (1990) Development 108:213–222.

Salminen et al. (1998) Dev. Dyn. 212:326–333.

Sambrook et al. (1989) Molecular cloning: a laboratory manual second edition—Cold Spring Harbor Laboratory Press. Cold Spring Harbor, N.Y. USA.

Sauer et al. (1988) Proc. Natl. Acad. Sci. USA 85:5166–5170.

Sauer et al. (1989) Nucl. Acids Res. 17:147–161.

Sauer (1994) B., Current Opinion in Biotechnology 5:521–527.

Sauer (1998) Methods 14:381–392.

Shaikh et al. (2000) J. Mol. Biol. 302:27–48.

Schlake & Bode (1994) Biochemistry 33:12746–12751.

Schnütgen et al. (2001) A novel strategy for monitoring Cre-mediated recombination at the level of individual cells. submitted.

Schwenk et al. (1998) Nucleic Acids Res. 26:1427–1432.

Skarnes et al. (1992) Genes Dev. 6:903–918.

Soriano (1999) Nat. Genet. 21:70–71.

Taneja et al. (1995) Proc. Natl. Acad. Sci. USA 92:7854–7858.

Thomas et al. (1993) Trends Genet. 9:395–398.

Tsien et al. (1996) Cell 87:1317–1326.

Zambrowicz et al. (1998) Nature 392:608–611.

Zhang et al. (1996) Biochem. Biophys. Res. Com. 227: 707–711.

The invention claimed is:

1. An isolated DNA molecule comprising a sequence A flanked by site specific recombinase targeting sequences (SSRTS) L1 and a sequence B flanked by site specific recombinase targeting sequences (SSRTS) L2, said SSRTS L1 and SSRTS L2 being unable to recombine with one another, wherein:

i) sequences L1 are in an orientation opposite one another, wherein said sequences point towards each other or away from each other, ii) sequences L2 are in an orientation opposite to each other, wherein said sequences point towards each other or away from each other, iii) the order of the sequences in said isolated DNA molecule is 5'-L1-L2-sequence A-sequence B-L1-L2-3', and iv) at least one of sequence A or sequence B encodes a protein.

2. The isolated DNA molecule according of claim 1 wherein the same recombinase recognizes SSRTS L1 and SSRTS L2.

3. The isolated DNA molecule of claim 2 wherein the recombinase specific for the SSRTS is selected from the group consisting of Cre recombinase of bacteriophage P1, the FLP recombinase of *Saccharomyces cerevisiae*, the R recombinase of *Zygosaccharomyces rouxii* pSR1, the A recombinase of *Kluyveromyces drosophilarium* pKD1, the A recombinase of *Kluyveromyces waltii* pKW1, the integrase λ Int, the recombinase of the GIN recombination system of Mu phage, and bacterial β recombinase.

4. The isolated DNA molecule according to claim 3, wherein said recombinase is said Cre recombinase of bacteriophage P1.

5. The isolated DNA molecule according to claim 4, wherein each of said SSRTS L1 and SSRTS L2, specific for Cre recombinase is selected from the group consisting of Lox P1, Lox 66, Lox 71, Lox 511, Lox 512, Lox 514, and a mutated Lox P1 sequence, wherein said mutated Lox P1 sequence comprises at least one point mutation in the spacer sequence.

6. The isolated DNA molecule according to claim 5, wherein either SSRTS L1 comprises the Lox P1 sequence (SEQ ID NO: 52) and SSRTS L2 comprises the Lox 511 sequence (SEQ ID NO: 53) or SSRTS L1 comprises the Lox 511 sequence and SSRTS L2 comprises the Lox P1 sequence.

7. The isolated DNA molecule according to claim 3 wherein the recombinase is the FLP recombinase of *Saccharomyces cerevisiae.*

8. The isolated DNA molecule according to claim 7, wherein said SSRTS L1 and/or SSRTS L2 specific for said FLP recombinase are chosen from the group consisting of FRT-S and FRT-F3$^{0.88}$.

9. The isolated DNA molecule according to claim 1, wherein sequences A and/or B encode at least one exon.

10. The isolated DNA molecule according to claim 1, wherein an IRES sequence is inserted 5', 3', or 5' and 3' to the at least one of sequence A or sequence B that encodes a protein.

11. The isolated DNA molecule according to claim 1, wherein said protein is selected from the group consisting of a reporter protein and a selection marker.

12. The isolated DNA molecule according to claim 11, wherein said reporter protein is selected from the group consisting of an autofluorescence protein and an enzyme detectable histochemically.

13. The isolated DNA molecule of claim 12, wherein said autofluorescence protein is selected from the group consisting of the green fluorescent protein (GFP), the enhanced green fluorescent protein (EGFP), the red fluorescent protein (RFP), the blue fluorescent protein (BFP), and the yellow fluorescent protein (YFP).

14. The isolated DNA molecule according to claim 12 wherein said enzyme detectable histochemically is selected from the group consisting of β-galactosidase, β-glucoronidase, alkaline phosphatase, luciferase, alcohol dehydrogenase, and chloramphenicol-acetyl transferase.

15. A vector comprising the isolated DNA molecule according to claim 1.

* * * * *

UNITED STATES PATENT AND TRADEMARK OFFICE

CERTIFICATE OF CORRECTION

PATENT NO. : 7,074,611 B2 Page 1 of 1
APPLICATION NO. : 09/843150
DATED : July 11, 2006
INVENTOR(S) : Pierre Chambon, Norbert B. Ghyselinck and Frank Schnutgen It is certified that error appears in the above-identified patent and that said Letters Patent is hereby corrected as shown below:

On the cover page, item (73), the Assignee should be:

GIE-CERBM, Centre Europeen de Recherche en Biologie et en Medecine (GIE)

Signed and Sealed this

First Day of May, 2007

JON W. DUDAS

*Director of the United States Patent and Trademark Office*

SEQUENCE LISTING

<160> NUMBER OF SEQ ID NOS: 56

<210> SEQ ID NO 1
<211> LENGTH: 60
<212> TYPE: DNA
<213> ORGANISM: Artificial sequence
<220> FEATURE:
<223> OTHER INFORMATION: Description of Artificial sequence: R1
synthetic oligonucleotide

<400> SEQUENCE: 1
aattgataac ttcgtatagc atacattata cgaagttatc caagcttcac catcgacccg 60

<210> SEQ ID NO 2
<211> LENGTH: 60
<212> TYPE: DNA
<213> ORGANISM: Artificial sequence
<220> FEATURE:
<223> OTHER INFORMATION: Description of Artificial sequence: R2
synthetic oligonucleotide

<400> SEQUENCE: 2
aattcgggtc gatggtgaag cttggataac ttcgtataat gtatgctata cgaagttatc 60

<210> SEQ ID NO 3
<211> LENGTH: 61
<212> TYPE: DNA
<213> ORGANISM: Artificial sequence
<220> FEATURE:
<223> OTHER INFORMATION: Description of Artificial sequence: R3
synthetic oligonucleotide

<400> SEQUENCE: 3
aattgccaag catcaccatc gacccataac ttcgtatagt atacattata cgaagttatc 60
g 61

<210> SEQ ID NO 4
<211> LENGTH: 61
<212> TYPE: DNA
<213> ORGANISM: Artificial sequence
<220> FEATURE:
<223> OTHER INFORMATION: Description of Artificial sequence: R4
synthetic oligonucleotide

<400> SEQUENCE: 4
aattcgataa cttcgtataa tgtatactat acgaagttat gggtcgatgg tgatgcttgg 60
c 61

-continued

<210> SEQ ID NO 5
<211> LENGTH: 67
<212> TYPE: DNA
<213> ORGANISM: Artificial sequence
<220> FEATURE:
<223> OTHER INFORMATION: Description of Artificial sequence: R5
synthetic oligonucleotide

<400> SEQUENCE: 5
ctagtggatc cgataacttc gtataatgta tgctatacga agttatccaa gcatcaccat 60
cgaccct 67

<210> SEQ ID NO 6
<211> LENGTH: 67
<212> TYPE: DNA
<213> ORGANISM: Artificial sequence
<220> FEATURE:
<223> OTHER INFORMATION: Description of Artificial sequence: R6
synthetic oligonucleotide

<400> SEQUENCE: 6
ctagagggtc gatggtgatg cttggataac ttcgtatagc atacattata cgaagttatc 60
ggatcca 67

<210> SEQ ID NO 7
<211> LENGTH: 60
<212> TYPE: DNA
<213> ORGANISM: Artificial sequence
<220> FEATURE:
<223> OTHER INFORMATION: Description of Artificial sequence: R7
synthetic oligonucleotide

<400> SEQUENCE: 7
ctagtccaga tctcaccatc gacccataac ttcgtataat gtatactata cgaagttatt 60

<210> SEQ ID NO 8
<211> LENGTH: 60
<212> TYPE: DNA
<213> ORGANISM: Artificial sequence
<220> FEATURE:
<223> OTHER INFORMATION: Description of Artificial sequence: R8
synthetic oligonucleotide

<400> SEQUENCE: 8
ctagaataac ttcgtatagt atacattata cgaagttatg ggtcgatggt gagatctgga 60

<210> SEQ ID NO 9
<211> LENGTH: 28
<212> TYPE: DNA
<213> ORGANISM: Artificial sequence
<220> FEATURE:
<223> OTHER INFORMATION: Description of Artificial sequence: R9
synthetic oligonucleotide

<400> SEQUENCE: 9
ggggaattct tcttgtacag ctcgtcca 28

<210> SEQ ID NO 10
<211> LENGTH: 32
<212> TYPE: DNA
<213> ORGANISM: Artificial sequence
<220> FEATURE:
<223> OTHER INFORMATION: Description of Artificial sequence: R10
synthetic oligonucleotide

<400> SEQUENCE: 10

-continued

```
ggggaattcc catggtgagc aagggcgagg ag                                 32


<210> SEQ ID NO 11
<211> LENGTH: 46
<212> TYPE: DNA
<213> ORGANISM: Artificial sequence
<220> FEATURE:
<223> OTHER INFORMATION: Description of Artificial sequence:  R11
      synthetic oligonucleotide

<400> SEQUENCE: 11

ctatcagggc gatggcccac tacgtgttct gaggcggaaa gaacca                  46


<210> SEQ ID NO 12
<211> LENGTH: 47
<212> TYPE: DNA
<213> ORGANISM: Artificial sequence
<220> FEATURE:
<223> OTHER INFORMATION: Description of Artificial sequence:  R12
      synthetic oligonucleotide

<400> SEQUENCE: 12

ggaatagctc agaggccgag gcggcctcgg cctctgcata aataaaa                 47


<210> SEQ ID NO 13
<211> LENGTH: 20
<212> TYPE: DNA
<213> ORGANISM: Artificial sequence
<220> FEATURE:
<223> OTHER INFORMATION: Description of Artificial sequence:  Synthetic
      oligonucleotide

<400> SEQUENCE: 13

gtgcatctgc cagtttgagg                                               20


<210> SEQ ID NO 14
<211> LENGTH: 17
<212> TYPE: DNA
<213> ORGANISM: Artificial sequence
<220> FEATURE:
<223> OTHER INFORMATION: Description of Artificial sequence:  Synthetic
      oligonucleotide

<400> SEQUENCE: 14

aatacgactc actatag                                                  17


<210> SEQ ID NO 15
<211> LENGTH: 40
<212> TYPE: DNA
<213> ORGANISM: Artificial sequence
<220> FEATURE:
<223> OTHER INFORMATION: Description of Artificial sequence:  G1
      synthetic oligonucleotide

<400> SEQUENCE: 15

ggccgcataa cttcgtataa tgtatgctat acgaagttat                         40


<210> SEQ ID NO 16
<211> LENGTH: 40
<212> TYPE: DNA
<213> ORGANISM: Artificial sequence
<220> FEATURE:
<223> OTHER INFORMATION: Description of Artificial sequence:  G2
      synthetic oligonucleotide

<400> SEQUENCE: 16
```

-continued ggccataact tcgtatagca tacattatac gaagttatgc 40

<210> SEQ ID NO 17
<211> LENGTH: 50
<212> TYPE: DNA
<213> ORGANISM: Artificial sequence
<220> FEATURE:
<223> OTHER INFORMATION: Description of Artificial sequence: G3
synthetic oligonucleotide

<400> SEQUENCE: 17
tataatgtat gctatacgaa gttattcctt ggcctggaat ttgcagaatt 50

<210> SEQ ID NO 18
<211> LENGTH: 50
<212> TYPE: DNA
<213> ORGANISM: Artificial sequence
<220> FEATURE:
<223> OTHER INFORMATION: Description of Artificial sequence: G4
synthetic oligonucleotide

<400> SEQUENCE: 18
gcccggggga tccactagtt ctagatgtct ccaccgctga atgaaaagca 50

<210> SEQ ID NO 19
<211> LENGTH: 64
<212> TYPE: DNA
<213> ORGANISM: Artificial sequence
<220> FEATURE:
<223> OTHER INFORMATION: Description of Artificial sequence: G5
synthetic oligonucleotide

<400> SEQUENCE: 19
ctagtatgga taaagttttc cggaattccg ctctagactc atcaatgtta tcttatcatg 60
tcta 64

<210> SEQ ID NO 20
<211> LENGTH: 64
<212> TYPE: DNA
<213> ORGANISM: Artificial sequence
<220> FEATURE:
<223> OTHER INFORMATION: Description of Artificial sequence: G6
synthetic oligonucleotide

<400> SEQUENCE: 20
ctagtagaca tgataagata acattgatga gtctagagcg gaattccgga aaactttatc 60
cata 64

<210> SEQ ID NO 21
<211> LENGTH: 64
<212> TYPE: DNA
<213> ORGANISM: Artificial sequence
<220> FEATURE:
<223> OTHER INFORMATION: Description of Artificial sequence: G7
synthetic oligonucleotide

<400> SEQUENCE: 21
gctacgtaat aacttcgtat aatgtatact atacgaagtt atgggtcgat ggtgagatct 60
ccgc 64

<210> SEQ ID NO 22
<211> LENGTH: 64
<212> TYPE: DNA
<213> ORGANISM: Artificial sequence
<220> FEATURE:

-continued

```
<223> OTHER INFORMATION: Description of Artificial sequence:  G8
      synthetic oligonucleotide

<400> SEQUENCE: 22

ggagatctca ccatcgaccc ataacttcgt atagtataca ttatacgaag ttattacgta     60

gcgc                                                                  64


<210> SEQ ID NO 23
<211> LENGTH: 12
<212> TYPE: DNA
<213> ORGANISM: Artificial sequence
<220> FEATURE:
<223> OTHER INFORMATION: Description of Artificial sequence:  G9
      synthetic oligonucleotide

<400> SEQUENCE: 23

gatcttacgt aa                                                         12


<210> SEQ ID NO 24
<211> LENGTH: 42
<212> TYPE: DNA
<213> ORGANISM: Artificial sequence
<220> FEATURE:
<223> OTHER INFORMATION: Description of Artificial sequence:  G10
      synthetic oligonucleotide

<400> SEQUENCE: 24

ggccgggaag ttcctattct ctagaaagta taggaacttc cc                        42


<210> SEQ ID NO 25
<211> LENGTH: 42
<212> TYPE: DNA
<213> ORGANISM: Artificial sequence
<220> FEATURE:
<223> OTHER INFORMATION: Description of Artificial sequence:  G10
      synthetic oligonucleotide

<400> SEQUENCE: 25

ggccgggaag ttcctatact ttctagagaa taggaacttc cc                        42


<210> SEQ ID NO 26
<211> LENGTH: 60
<212> TYPE: DNA
<213> ORGANISM: Artificial sequence
<220> FEATURE:
<223> OTHER INFORMATION: Description of Artificial sequence:  G12
      synthetic oligonucleotide

<400> SEQUENCE: 26

aagataactt cgtataatgt atgctatacg aagttatcca agcatcacca tcgacccgtt     60


<210> SEQ ID NO 27
<211> LENGTH: 60
<212> TYPE: DNA
<213> ORGANISM: Artificial sequence
<220> FEATURE:
<223> OTHER INFORMATION: Description of Artificial sequence:  G13
      synthetic oligonucleotide

<400> SEQUENCE: 27

aacgggtcga tggtgatgct tggataactt cgtatagcat acattatacg aagttatctt     60


<210> SEQ ID NO 28
<211> LENGTH: 60
<212> TYPE: DNA
<213> ORGANISM: Artificial sequence
```

```
<220> FEATURE:
<223> OTHER INFORMATION: Description of Artificial sequence: G14
      synthetic oligonucleotide

<400> SEQUENCE: 28

aagccaagca tcaccatcga cccataactt cgtataatgt atactatacg aagttatgtt    60

<210> SEQ ID NO 29
<211> LENGTH: 60
<212> TYPE: DNA
<213> ORGANISM: Artificial sequence
<220> FEATURE:
<223> OTHER INFORMATION: Description of Artificial sequence: G15
      synthetic oligonucleotide

<400> SEQUENCE: 29

aacataactt cgtatagtat acattatacg aagttatggg tcgatggtga tgcttggctt    60

<210> SEQ ID NO 30
<211> LENGTH: 51
<212> TYPE: DNA
<213> ORGANISM: Artificial sequence
<220> FEATURE:
<223> OTHER INFORMATION: Description of Artificial sequence: J1
      synthetic oligonucleotide

<400> SEQUENCE: 30

actagtggat cccccgggct gcaggaattc taccgggtag gggaggcgct t              51

<210> SEQ ID NO 31
<211> LENGTH: 79
<212> TYPE: DNA
<213> ORGANISM: Artificial sequence
<220> FEATURE:
<223> OTHER INFORMATION: Description of Artificial sequence: J2
      synthetic oligonucleotide

<400> SEQUENCE: 31

gtatcgataa gcttgatatc gccgctcgag acttacctga ctggccgtcg ttttacagtc    60

agaagaactc gtcaagaag                                                 79

<210> SEQ ID NO 32
<211> LENGTH: 58
<212> TYPE: DNA
<213> ORGANISM: Artificial sequence
<220> FEATURE:
<223> OTHER INFORMATION: Description of Artificial sequence: J3
      synthetic oligonucleotide

<400> SEQUENCE: 32

ctcgcgagga attcaaccag aagttcctat tctctagaaa gtataggaac ttccagct       58

<210> SEQ ID NO 33
<211> LENGTH: 58
<212> TYPE: DNA
<213> ORGANISM: Artificial sequence
<220> FEATURE:
<223> OTHER INFORMATION: Description of Artificial sequence: J4
      synthetic oligonucleotide

<400> SEQUENCE: 33

ggaagttcct atactttcta gagaatagga acttctggtt gaattcctcg cgagagct       58

<210> SEQ ID NO 34
<211> LENGTH: 61
<212> TYPE: DNA
```

-continued

```
<213> ORGANISM: Artificial sequence
<220> FEATURE:
<223> OTHER INFORMATION: Description of Artificial sequence:  J5
      synthetic oligonucleotide

<400> SEQUENCE: 34

aatgcctacc ggaccatcat aacttcgtat aatgtatact atacgaagtt ataagcttgc     60

a                                                                     61


<210> SEQ ID NO 35
<211> LENGTH: 61
<212> TYPE: DNA
<213> ORGANISM: Artificial sequence
<220> FEATURE:
<223> OTHER INFORMATION: Description of Artificial sequence:  J6
      synthetic oligonucleotide

<400> SEQUENCE: 35

agcttataac ttcgtatagt atacattata cgaagttatg atggtccggt aggcatttgc     60

a                                                                     61


<210> SEQ ID NO 36
<211> LENGTH: 59
<212> TYPE: DNA
<213> ORGANISM: Artificial sequence
<220> FEATURE:
<223> OTHER INFORMATION: Description of Artificial sequence:  J7
      synthetic oligonucleotide

<400> SEQUENCE: 36

gagctcataa cttcgtataa tgtatgctat acgaagttat ccaagcatca ccatatgca      59


<210> SEQ ID NO 37
<211> LENGTH: 59
<212> TYPE: DNA
<213> ORGANISM: Artificial sequence
<220> FEATURE:
<223> OTHER INFORMATION: Description of Artificial sequence:  J8
      synthetic oligonucleotide

<400> SEQUENCE: 37

tatggtgatg cttggataac ttcgtatagc atacattata cgaagttatg agctctgca      59


<210> SEQ ID NO 38
<211> LENGTH: 41
<212> TYPE: DNA
<213> ORGANISM: Artificial sequence
<220> FEATURE:
<223> OTHER INFORMATION: Description of Artificial sequence:  J9
      synthetic oligonucleotide

<400> SEQUENCE: 38

tcgacataac ttcgtataat gtatactata cgaagttata c                         41


<210> SEQ ID NO 39
<211> LENGTH: 41
<212> TYPE: DNA
<213> ORGANISM: Artificial sequence
<220> FEATURE:
<223> OTHER INFORMATION: Description of Artificial sequence:  J10
      synthetic oligonucleotide

<400> SEQUENCE: 39

tcgagtataa cttcgtatag tatacattat acgaagttat g                         41
```

-continued

<210> SEQ ID NO 40
<211> LENGTH: 48
<212> TYPE: DNA
<213> ORGANISM: Artificial sequence
<220> FEATURE:
<223> OTHER INFORMATION: Description of Artificial sequence: J11
synthetic oligonucleotide

<400> SEQUENCE: 40
tcgaagaagt tcctaatcta tttgaagtat aggaacttcg cggccgca 48

<210> SEQ ID NO 41
<211> LENGTH: 48
<212> TYPE: DNA
<213> ORGANISM: Artificial sequence
<220> FEATURE:
<223> OTHER INFORMATION: Description of Artificial sequence: J12
synthetic oligonucleotide

<400> SEQUENCE: 41
tcgatgcggc cgcgaagttc ctatacttca aatagattag gaacttct 48

<210> SEQ ID NO 42
<211> LENGTH: 48
<212> TYPE: DNA
<213> ORGANISM: Artificial sequence
<220> FEATURE:
<223> OTHER INFORMATION: Description of Artificial sequence: J13
synthetic oligonucleotide

<400> SEQUENCE: 42
ccggtccttg gcctggaatt tgcactctgt tgacaaccat tgtctcct 48

<210> SEQ ID NO 43
<211> LENGTH: 40
<212> TYPE: DNA
<213> ORGANISM: Artificial sequence
<220> FEATURE:
<223> OTHER INFORMATION: Description of Artificial sequence: J14
synthetic oligonucleotide

<400> SEQUENCE: 43
gtaatacgac tcactatagg gaattccgcc cctctccctc 40

<210> SEQ ID NO 44
<211> LENGTH: 40
<212> TYPE: DNA
<213> ORGANISM: Artificial sequence
<220> FEATURE:
<223> OTHER INFORMATION: Description of Artificial sequence: J15
synthetic oligonucleotide

<400> SEQUENCE: 44
gagggagagg ggcggaattc cctatagtga gtcgtattac 40

<210> SEQ ID NO 45
<211> LENGTH: 46
<212> TYPE: DNA
<213> ORGANISM: Artificial sequence
<220> FEATURE:
<223> OTHER INFORMATION: Description of Artificial sequence: J16
synthetic oligonucleotide

<400> SEQUENCE: 45
ctccaccgct gaatgaaaag cagcatggtt gtggcaagct tatcat 46

<210> SEQ ID NO 46

-continued

<211> LENGTH: 18
<212> TYPE: DNA
<213> ORGANISM: Artificial sequence
<220> FEATURE:
<223> OTHER INFORMATION: Description of Artificial sequence: Synthetic oligonucleotide

<400> SEQUENCE: 46
taacaatttc acacagga 18

<210> SEQ ID NO 47
<211> LENGTH: 36
<212> TYPE: DNA
<213> ORGANISM: Artificial sequence
<220> FEATURE:
<223> OTHER INFORMATION: Description of Artificial sequence: QT synthetic oligonucleotide

<400> SEQUENCE: 47
ccagtgagca gagtgacgag gactcgagct caagct 36

<210> SEQ ID NO 48
<211> LENGTH: 18
<212> TYPE: DNA
<213> ORGANISM: Artificial sequence
<220> FEATURE:
<223> OTHER INFORMATION: Description of Artificial sequence: Q0 synthetic oligonucleotide

<400> SEQUENCE: 48
ccagtgagca gagtgacg 18

<210> SEQ ID NO 49
<211> LENGTH: 20
<212> TYPE: DNA
<213> ORGANISM: Artificial sequence
<220> FEATURE:
<223> OTHER INFORMATION: Description of Artificial sequence: Neo1 synthetic oligonucleotide

<400> SEQUENCE: 49
accgcttcct cgtgctttac 20

<210> SEQ ID NO 50
<211> LENGTH: 18
<212> TYPE: DNA
<213> ORGANISM: Artificial sequence
<220> FEATURE:
<223> OTHER INFORMATION: Description of Artificial sequence: Q1 synthetic oligonucleotide

<400> SEQUENCE: 50
gaggactcga gctcaagc 18

<210> SEQ ID NO 51
<211> LENGTH: 20
<212> TYPE: DNA
<213> ORGANISM: Artificial sequence
<220> FEATURE:
<223> OTHER INFORMATION: Description of Artificial sequence: Neo2 synthetic oligonucleotide

<400> SEQUENCE: 51
gccttcttga cgagttcttc 20

<210> SEQ ID NO 52
<211> LENGTH: 34

-continued

<212> TYPE: DNA
<213> ORGANISM: Artificial sequence
<220> FEATURE:
<223> OTHER INFORMATION: Description of Artificial sequence: LoxP1
synthetic oligonucleotide

<400> SEQUENCE: 52
ataacttcgt ataatgtatg ctatacgaag ttat 34

<210> SEQ ID NO 53
<211> LENGTH: 34
<212> TYPE: DNA
<213> ORGANISM: Artificial sequence
<220> FEATURE:
<223> OTHER INFORMATION: Description of Artificial sequence: Lox511
synthetic oligonucleotide

<400> SEQUENCE: 53
ataacttcgt ataatgtatg ctatacgaag ttat 34

<210> SEQ ID NO 54
<211> LENGTH: 8693
<212> TYPE: DNA
<213> ORGANISM: Artificial sequence
<220> FEATURE:
<223> OTHER INFORMATION: Description of Artificial sequence: DNA
sequence of plasmid pFlExR
<220> FEATURE:
<223> OTHER INFORMATION: Position 1 to 360 SV40 promotor, sense
<220> FEATURE:
<223> OTHER INFORMATION: Position 365 to 1015 rabbit beta globin intron,
sense
<220> FEATURE:
<223> OTHER INFORMATION: Position 1050 loxP1 site, sense
<220> FEATURE:
<223> OTHER INFORMATION: Position 1130 lox511 site, sense
<220> FEATURE:
<223> OTHER INFORMATION: Position 1170 to 2050 EGFP polyA gene, sense
<220> FEATURE:
<223> OTHER INFORMATION: Position 2060 to 5700 LacZ polyA gene, antisense
<220> FEATURE:
<223> OTHER INFORMATION: Position 5710 loxP1 site, antisense
<220> FEATURE:
<223> OTHER INFORMATION: Position 5790 lox511 site, antisense
<220> FEATURE:
<223> OTHER INFORMATION: Position 5830 to 8693 vector sequence

<400> SEQUENCE: 54
gtcgacttct gaggcggaaa gaaccagctg tggaatgtgt gtcagttagg gtgtggaaag 60
tccccaggct ccccagcagg cagaagtatg caaagcatgc atctcaatta gtcagcaacc 120
aggtgtggaa agtccccagg ctccccagca ggcagaagta tgcaaagcat gcatctcaat 180
tagtcagcaa ccatagtccc gcccctaact ccgcccatcc cgcccctaac tccgcccagt 240
tccgcccatt ctccgcccca tggctgacta attttttta tttatgcaga ggccgaggcc 300
gcctcggcct ctgagctatt ccagaagtag tgaggaggct tttttggagg cctaggcttt 360
tgcaaaaagc tggatcgatc ctgagaactt cagggtgagt ttggggaccc ttgattgttc 420
tttctttttc gctattgtaa aattcatgtt atatggaggg ggcaaagttt tcagggtgtt 480
gtttagaatg ggaagatgtc ccttgtatca ccatggaccc tcatgataat tttgtttctt 540
tcactttcta ctctgttgac aaccattgtc tcctcttatt ttcttttcat tttctgtaac 600
tttttcgtta aactttagct tgcatttgta acgaattttt aaattcactt ttgtttattt 660
gtcagattgt aagtactttc tctaatcact tttttttcaa ggcaatcagg gtatattata 720
ttgtacttca gcacagtttt agagaacaat tgttataatt aaatgataag gtagaatatt 780

-continued

```
tctgcatata aattctggct ggcgtggaaa tattcttatt ggtagaaaca actacatcct    840
ggtcatcatc ctgcctttct ctttatggtt acaatgatat acactgtttg agatgaggat    900
aaaatactct gagtccaaac cgggcccctc tgctaaccat gttcatgcct tcttcttttt    960
cctacagctc ctgggcaacg tgctggttat tgtgctgtct catcattttg gcaaagaatt   1020
gtaatacgac tcactatagg gcgaattgat aacttcgtat agcatacatt atacgaagtt   1080
atccaagctt caccatcgac ccgaattgcc aagcatcacc atcgacccat aacttcgtat   1140
agtatacatt atacgaagtt atcgaattcc catggtgagc aagggcgagg agctgttcac   1200
cggggtggtg cccatcctgg tcgagctgga cggcgacgta aacggccaca agttcagcgt   1260
gtccggcgag ggcgagggcg atgccaccta cggcaagctg accctgaagt tcatctgcac   1320
caccggcaag ctgcccgtgc cctggcccac cctcgtgacc accctgacct acggcgtgca   1380
gtgcttcagc cgctaccccg accacatgaa gcagcacgac ttcttcaagt ccgccatgcc   1440
cgaaggctac gtccaggagc gcaccatctt cttcaaggac gacggcaact acaagacccg   1500
cgccgaggtg aagttcgagg gcgacaccct ggtgaaccgc atcgagctga agggcatcga   1560
cttcaaggag gacggcaaca tcctggggca caagctggag tacaactaca acagccacaa   1620
cgtctatatc atggccgaca agcagaagaa cggcatcaag gtgaacttca agatccgcca   1680
caacatcgag gacggcagcg tgcagctcgc cgaccactac cagcagaaca cccccatcgg   1740
cgacggcccc gtgctgctgc ccgacaacca ctacctgagc acccagtccg ccctgagcaa   1800
agaccccaac gagaagcgcg atcacatggt cctgctggag ttcgtgaccg ccgccgggat   1860
cactctcggc atggacgagc tgtacaagta agaattcgga tcttattaaa gcagaacttg   1920
tttattgcag cttataatgg ttacaaataa agcaatagca tcacaaattt cacaaataaa   1980
gcattttttt cactgcattc tagttgtggt ttgtccaaac tcatcaatgt atcttatcat   2040
gtctggtcga ctctagtgga tccagacatg ataagataac attgatgagt ttggacaaac   2100
cacaactaga atgcagtgaa aaaaatgctt tatttgtgaa atttgtgatg ctattgcttt   2160
atttgtaacc attataagct gcaataaaca agttccgagt ttgtcagaaa gcagaccaaa   2220
cagcggttgg aataatagcg agaacagaga aatagcggca aaaataatac ccgtatcact   2280
tttgctgata tggttgatgt catgtagcca aatcgggaaa aacgggaagt aggctcccat   2340
gataaaaaag taaaagaaaa agaataaacc gaacatccaa aagtttgtgt tttttaaata   2400
gtacataatg gatttcctta cgcgaaatac gggcagacat ggcctgcccg gttattatta   2460
tttttgacac cagaccaact ggtaatggta gcgaccggcg ctcagctgga attccgccga   2520
tactgacggg ctccaggagt cgtcgccacc aatccccata tggaaaccgt cgatattcag   2580
ccatgtgcct tcttccgcgt gcagcagatg gcgatggctg gtttccatca gttgctgttg   2640
actgtagcgg ctgatgttga actggaagtc gccgcgccac tggtgtgggc cataattcaa   2700
ttcgcgcgtc ccgcagcgca gaccgttttc gctcgggaag acgtacgggg tatacatgtc   2760
tgacaatggc agatcccagc ggtcaaaaca ggcggcagta aggcggtcgg gatagttttc   2820
ttgcggccct aatccgagcc agtttacccg ctctgctacc tgcgccagct ggcagttcag   2880
gccaatccgc gccggatgcg gtgtatcgct cgccacttca acatcaacgg taatcgccat   2940
ttgaccacta ccatcaatcc ggtaggtttt ccggctgata aataaggttt tcccctgatg   3000
ctgccacgcg tgagcggtcg taatcagcac cgcatcagca agtgtatctg ccgtgcactg   3060
caacaacgct gcttcggcct ggtaatggcc cgccgccttc cagcgttcga cccaggcgtt   3120
agggtcaatg cgggtcgctt cacttacgcc aatgtcgtta tccagcggtg cacgggtgaa   3180
```

-continued

```
ctgatcgcgc agcggcgtca gcagttgttt tttatcgcca atccacatct gtgaaagaaa   3240
gcctgactgg cggttaaatt gccaacgctt attacccagc tcgatgcaaa aatccatttc   3300
gctggtggtc agatgcggga tggcgtggga cgcggcgggg agcgtcacac tgaggttttc   3360
cgccagacgc cactgctgcc aggcgctgat gtgcccggct tctgaccatg cggtcgcgtt   3420
cggttgcact acgcgtactg tgagccagag ttgcccggcg ctctccggct gcggtagttc   3480
aggcagttca atcaactgtt taccttgtgg agcgacatcc agaggcactt caccgcttgc   3540
cagcggctta ccatccagcg ccaccatcca gtgcaggagc tcgttatcgc tatgacggaa   3600
caggtattcg ctggtcactt cgatggtttg cccggataaa cggaactgga aaaactgctg   3660
ctggtgtttt gcttccgtca gcgctggatg cggcgtgcgg tcggcaaaga ccagaccgtt   3720
catacagaac tggcgatcgt tcggcgtatc gccaaaatca ccgccgtaag ccgaccacgg   3780
gttgccgttt tcatcatatt taatcagcga ctgatccacc cagtcccaga cgaagccgcc   3840
ctgtaaacgg ggatactgac gaaacgcctg ccagtattta gcgaaaccgc caagactgtt   3900
acccatcgcg tgggcgtatt cgcaaaggat cagcgggcgc gtctctccag gtagcgaaag   3960
ccattttttg atggaccatt tcggcacagc cgggaagggc tggtcttcat ccacgcgcgc   4020
gtacatcggg caaataatat cggtggccgt ggtgtcggct ccgccgcctt catactgcac   4080
cgggcgggaa ggatcgacag atttgatcca gcgatacagc gcgtcgtgat tagcgccgtg   4140
gcctgattca ttccccagcg accagatgat cacactcggg tgattacgat cgcgctgcac   4200
cattcgcgtt acgcgttcgc tcatcgccgg tagccagcgc ggatcatcgg tcagacgatt   4260
cattggcacc atgccgtggg tttcaatatt ggcttcatcc accacataca ggccgtagcg   4320
gtcgcacagc gtgtaccaca gcggatggtt cggataatgc gaacagcgca cggcgttaaa   4380
gttgttctgc ttcatcagca ggatatcctg caccatcgtc tgctcatcca tgacctgacc   4440
atgcagagga tgatgctcgt gacggttaac gcctcgaatc agcaacggct tgccgttcag   4500
cagcagcaga ccattttcaa tccgcacctc gcggaaaccg acatcgcagg cttctgcttc   4560
aatcagcgtg ccgtcggcgg tgtgcagttc aaccaccgca cgatagagat tcgggatttc   4620
ggcgctccac agtttcgggt tttcgacgtt cagacgtagt gtgacgcgat cggcataacc   4680
accacgctca tcgataattt caccgccgaa aggcgcggtg ccgctggcga cctgcgtttc   4740
accctgccat aaagaaactg ttacccgtag gtagtcacgc aactcgccgc acatctgaac   4800
ttcagcctcc agtacagcgc ggctgaaatc atcattaaag cgagtggcaa catggaaatc   4860
gctgatttgt gtagtcggtt tatgcagcaa cgagacgtca cggaaaatgc cgctcatccg   4920
ccacatatcc tgatcttcca gataactgcc gtcactccaa cgcagcacca tcaccgcgag   4980
gcggttttct ccggcgcgta aaaatgcgct caggtcaaat tcagacggca aacgactgtc   5040
ctggccgtaa ccgacccagc gcccgttgca ccacagatga aacgccgagt taacgccatc   5100
aaaaataatt cgcgtctggc cttcctgtag ccagctttca tcaacattaa atgtgagcga   5160
gtaacaaccc gtcggattct ccgtgggaac aaacggcgga ttgaccgtaa tgggataggt   5220
tacgttggtg tagatgggcg catcgtaacc gtgcatctgc cagtttgagg ggacgacgac   5280
agtatcggcc tcaggaagat cgcactccag ccagctttcc ggcaccgctt ctggtgccgg   5340
aaaccaggca aagcgccatt cgccattcag gctgcgcaac tgttgggaag ggcgatcggt   5400
gcgggcctct tcgctattac gccagctggc gaaaggggga tgtgctgcaa ggcgattaag   5460
ttgggtaacg ccagggtttt cccagtcacg acgttgtaaa acgacggcca gtgccaagct   5520
```

-continued

```
tggactcaaa aaacttagca attctgaagg aaagtccttg gggtcttcta cctttctctt   5580
cttttttgcg gaattccgga aaactttatc catctttgca aagcttttttg caaaagccta   5640
ggcctccaaa aaagcctcct cactacttct ggaatagctc agaggccgtc gaccccggga   5700
attcggatcc gataacttcg tataatgtat gctatacgaa gttatccaag catcaccatc   5760
gaccctctag tccagatctc accatcgacc cataacttcg tataatgtat actatacgaa   5820
gttattctag actcttccgc ttcctcgctc actgactcgc tgcgctcggt cgttcggctg   5880
cggcgagcgg tatcagctca ctcaaaggcg gtaatacggt tatccacaga atcaggggat   5940
aacgcaggaa agaacatgtg agcaaaaggc cagcaaaagg ccaggaaccg taaaaaggcc   6000
gcgttgctgg cgtttttcca taggctccgc ccccctgacg agcatcacaa aaatcgacgc   6060
tcaagtcaga ggtggcgaaa cccgacagga ctataaagat accaggcgtt tccccctgga   6120
agctccctcg tgcgctctcc tgttccgacc ctgccgctta ccggatacct gtccgccttt   6180
ctcccttcgg gaagcgtggc gctttctcaa tgctcacgct gtaggtatct cagttcggtg   6240
taggtcgttc gctccaagct gggctgtgtg cacgaacccc ccgttcagcc cgaccgctgc   6300
gccttatccg gtaactatcg tcttgagtcc aacccggtaa gacacgactt atcgccactg   6360
gcagcagcca ctggtaacag gattagcaga gcgaggtatg taggcggtgc tacagagttc   6420
ttgaagtggt ggcctaacta cggctacact agaaggacag tatttggtat ctgcgctctg   6480
ctgaagccag ttaccttcgg aaaaagagtt ggtagctctt gatccggcaa acaaaccacc   6540
gctggtagcg gtggtttttt tgtttgcaag cagcagatta cgcgcagaaa aaaaggatct   6600
caagaagatc ctttgatctt ttctacgggg tctgacgctc agtggaacga aaactcacgt   6660
taagggattt tggtcatgag attatcaaaa aggatcttca cctagatcct tttaaattaa   6720
aaatgaagtt ttaaatcaat ctaaagtata tatgagtaaa cttggtctga cagttaccaa   6780
tgcttaatca gtgaggcacc tatctcagcg atctgtctat ttcgttcatc catagttgcc   6840
tgactccccg tcgtgtagat aactacgata cgggagggct taccatctgg ccccagtgct   6900
gcaatgatac cgcgagaccc acgctcaccg gctccagatt tatcagcaat aaaccagcca   6960
gccggaaggg ccgagcgcag aagtggtcct gcaactttat ccgcctccat ccagtctatt   7020
aattgttgcc gggaagctag agtaagtagt tcgccagtta atagtttgcg caacgttgtt   7080
gccattgcta caggcatcgt ggtgtcacgc tcgtcgtttg gtatggcttc attcagctcc   7140
ggttcccaac gatcaaggcg agttacatga tcccccatgt tgtgcaaaaa agcggttagc   7200
tccttcggtc ctccgatcgt tgtcagaagt aagttggccg cagtgttatc actcatggtt   7260
atggcagcac tgcataattc tcttactgtc atgccatccg taagatgctt ttctgtgact   7320
ggtgagtact caaccaagtc attctgagaa tagtgtatgc ggcgaccgag ttgctcttgc   7380
ccggcgtcaa tacgggataa taccgcgcca catagcagaa ctttaaaagt gctcatcatt   7440
ggaaaacgtt cttcggggcg aaaactctca aggatcttac cgctgttgag atccagttcg   7500
atgtaaccca ctcgtgcacc caactgatct tcagcatctt ttactttcac cagcgtttct   7560
gggtgagcaa aaacaggaag gcaaaatgcc gcaaaaaagg gaataagggc gacacggaaa   7620
tgttgaatac tcatactctt cctttttcaa tattattgaa gcatttatca gggttattgt   7680
ctcatgagcg gatacatatt tgaatgtatt tagaaaaata aacaaatagg ggttccgcgc   7740
acatttcccc gaaaagtgcc acctgacgtc taagaaacca ttattatcat gacattaacc   7800
tataaaaata ggcgtatcac gaggcccctt tcgtctcgcg cgtttcggtg atgacggtga   7860
aaacctctga cacatgcagc tcccggagac ggtcacagct tgtctgtaag cggatgccgg   7920
```

-continued

```
gagcagacaa gcccgtcagg gcgcgtcagc gggtgttggc gggtgtcggg gctggcttaa   7980

ctatgcggca tcagagcaga ttgtactgag agtgcaccat atgcggtgtg aaataccgca   8040

cagatgcgta aggagaaaat accgcatcag gaaattgtaa acgttaatat tttgttaaaa   8100

ttcgcgttaa atttttgtta aatcagctca ttttttaacc aataggccga aatcggcaaa   8160

atcccttata aatcaaaaga atagaccgag atagggttga gtgttgttcc agtttggaac   8220

aagagtccac tattaaagaa cgtggactcc aacgtcaaag ggcgaaaaac cgtctatcag   8280

ggcgatggcc cactacgtga accatcaccc taatcaagtt ttttggggtc gaggtgccgt   8340

aaagcactaa atcggaaccc taaagggagc ccccgattta gagcttgacg gggaaagccg   8400

gcgaacgtgg cgagaaagga agggaagaaa gcgaaaggag cgggcgctag ggcgctggca   8460

agtgtagcgg tcacgctgcg cgtaaccacc acacccgccg cgcttaatgc gccgctacag   8520

ggcgcgtcgc gccattcgcc attcaggcta cgcaactgtt gggaagggcg atcggtgcgg   8580

gcctcttcgc tattacgcca gctggcgaag ggggatgtg ctgcaaggcg attaagttgg   8640

gtaacgccag ggttttccca gtcacgacgt tgtaaaacga cggccagtga att          8693
```

```
<210> SEQ ID NO 55
<211> LENGTH: 17135
<212> TYPE: DNA
<213> ORGANISM: Artificial sequence
<220> FEATURE:
<223> OTHER INFORMATION: Description of Artificial sequence: DNA
      sequence of plasmid py6.0FlExBeta-Gal
<220> FEATURE:
<223> OTHER INFORMATION: Position 1 to 2360 genomic DNA RARgamma locus,
      sense
<220> FEATURE:
<223> OTHER INFORMATION: Position 2365 loxP1 site, sense
<220> FEATURE:
<223> OTHER INFORMATION: Position 2445 lox511 site, sense
<220> FEATURE:
<223> OTHER INFORMATION: Position 2480 to 2750 genomic DNA RARgamma
      locus, sense
<220> FEATURE:
<223> OTHER INFORMATION: Position 2753 to 2901 exon 8 RARgamma locus,
      sense
<220> FEATURE:
<223> OTHER INFORMATION: Position 2902 to 3395 genomic DNA RARgamma
      locus, sense
<220> FEATURE:
<223> OTHER INFORMATION: Position 3400 to 6983 LacZ polyA gene,
      antisense
<220> FEATURE:
<223> OTHER INFORMATION: Position 6984 to 6992 part exon 8 RARgamma
      locus, antisense
<220> FEATURE:
<223> OTHER INFORMATION: Position 6993 to 7257 genomic DNA RARgamma
      locus, antisense
<220> FEATURE:
<223> OTHER INFORMATION: Position 7265 loxP1 site, antisense
<220> FEATURE:
<223> OTHER INFORMATION: Position 7305 FRT site, sense
<220> FEATURE:
<223> OTHER INFORMATION: Position 7345 to 9150 PGK Neo polyA gene,
      sense
<220> FEATURE:
<223> OTHER INFORMATION: Position 9155 FRT site, sense
<220> FEATURE:
<223> OTHER INFORMATION: Position 9265 lox511 site, antisense
<220> FEATURE:
<223> OTHER INFORMATION: Position 9300 to 12175 genomic DNA RARgamma
      locus, sense
<220> FEATURE:
<223> OTHER INFORMATION: Position 12175 to 17135 vector sequence

<400> SEQUENCE: 55
```

-continued

```
gaattcttaa ccttgccatg cccagtataa tggggaacta ctgggcacat tggctggcat     60
ctgagtcaga aatatctggg tatatgtgta tgtgtgcgtg ggggtgttgg ctgtaaggct    120
cctagacagg gactatatat tcttatttag gcctctggag acattttggg cttggtagct    180
caatattttt gcatttctgt ttgagccagt aagtttggcc agtagtgcac ccctgtcaca    240
ctcagaggga aggtggttta aagtagggga ggattgtgtg ttactggctt ttggatggaa    300
actttagtgt cctggtgttg tgctgactga gtgcggtgtt tggtagtaga gctgtttagc    360
ccgtagctct gtgacttgtc atctaccaac atggagcact catgccttga tgtttgtgct    420
ttcctctgtt taaaggtcca gcccaaacta aggcagtgcc cactgtaggt ctgtctgctt    480
tggcgtctgt gtcatgttgg cctgcaaaag tgtgtgtctt caaggagatt gtgtgctaga    540
ttgtgagtcc aggcagctca agctctgggc cttgcagctg ggagcgttta cagcgggtta    600
taaagagttt gtttgaagct ccgctcagcc tggccaggaa tttcctcaat ttcagcaatt    660
tgggctttaa aaggagaaaa ccccgagccc accccctcct cctcagcagg ggcccctgct    720
gagcccagga gcggtgtccc tgtgctgagg tctcagctca gtgttgaaga ggggacccag    780
aagaccctgc cagctttgca gaacctccac ccacagcgac ctcagagcca tcgcatggca    840
ctttcagata ccgggggcgg ggatgatgtg ccagaggggt gccgagagag ggtgccggtg    900
ccattaggat gggaaaggct gcccgagggc aggctctctg ggccttcgt cttataattg     960
gctggtgctg cctgccccat gccagcctga ccgcacccag gccttgcgca agagaggaaa   1020
tgaggaaatg aggcagcgct ctgtgggtag ggagggcgtc agtgcaggag agagtaccac   1080
cccacgctca ggcctgtggg gaccccagga tgggctgaaa gtgagggccg gaaaggcctt   1140
ccaggcttcc ccaaacctcc cagcacctac cattcaggca accccacccc cagtcttgaa   1200
taaactccct gcacccttcc gcccccttc ttttgagggg gaatctaact ccagcaggat    1260
tcttatgcta attgggtgcg tggggggtgg ggtgggtgga gaaggcttcc ctctttgtaa   1320
ggtggtggag ctggtctgga acccccaacc tataggctct tctgtcctct cactaccttg   1380
ggtctcagta tggacttgtg accaggtggg ttacatggca tgggaggaaa gacgctggag   1440
gtcttcaaga tccaccccc accaccacca ctttttcca aattcgggca gcaggtcctg     1500
caggctggat agttttcaga tatcctgagc ttctgagggt gaaccctata ctctcccagc   1560
ctgtggcagg cttgtactct cagcagcctc ctgtataaag tgtgggctcc cccaactctg   1620
ggccttggct aggactccat ataaactaca atgactgttt tctgaagcag ttcaggaatg   1680
aagacaggct tggaaagggt ctggggcagc tcccttcccc ctcagctctg tttacccagt   1740
gtcacctgac cctctgctac accccaaact gctcctggac ctaagggcct gagtgaatcc   1800
ctgttttcct ccacagcttc tttcactaaa cgccacgtag ctatggtcag cgcccctgag   1860
agccttggct ccccagtcag ccgacactga gccggtcact cagctgctaa tgctcctttt   1920
ctgacctgag agcactttca ggaatgactt acattaagtc attcagccag gtgccagctg   1980
taggtagcct gtttgctcca tttgccttta catttgcggc cctcctcccc accccccacc   2040
gccaccaaat gctttcaggg gaactctggg attactagag tcaggagtga gccctaacct   2100
ttcagtttta tgcccctccc cgccccccttt aaaaatgtgt atggtgttct gtctatatgt  2160
attttcgcgt gccatttttg tgcctggtgc ccatggaaga tggaagaggg aaccggttct   2220
gttagaactg gcgattacaa atggttgtaa actaccatgt agatgctggg aatggaaccc   2280
tggtccttgg gagagcagcc agtgctctta cctgctgagt cccaaccaat cttcaacttt   2340
atggagcaga agcagagaag ttaagataac ttcgtataat gtatgctata cgaagttatc   2400
```

-continued

```
caagcatcac catcgacccg ttaagccaag catcaccatc gacccataac ttcgtataat   2460
gtatactata cgaagttatg ttaactcctt ggcctggaat ttgcagaatt gaacgttaat   2520
gtagaagagt tggctttatg ggggtgggga tggggtaggg ggcagtggtg gggcctgaaa   2580
tcccaacaag ctacaaagag tggtggtctg ggctttccag ggagtacctg ttaagggctt   2640
atgcacaagg gtgacaacag cggtcaccag caggtcccaa gaaagagagg ccatgggatg   2700
agggtgcttc tgctcagctt ctgcttatct tctcatgctg cttttcattc agcggtggag   2760
acacagagca ccagctcgga ggagatggta cccagctctc cctcaccccc accacctcct   2820
cgggtctata agccatgctt tgtatgcaat gacaagtctt ctggctacca ctatggggtc   2880
agctcctgtg aaggctgcaa ggtgtgtatg tggtgggggc gggtgagttt agcactcagt   2940
tgactgggct tataccatca gagatggaaa cataaggctg gctggcaatg tagcttagta   3000
ggtagaatgc ttgcttagca tacttgagaa ctcagcaaca catcagagac tctcttatgc   3060
caatgctcta agggcagaag caggcagatc tctgtgagtt caaggccagc ctagtctaca   3120
gagctagttc caggacagcc agggctacac aaagaaacct gtcttgaaga accaaaaatt   3180
aatgaataag tgattagata aataaaaatc gttttaaagg taggggggccc aggtactgtg   3240
ttcacatgag tgtttttgtc tgtgtggggt gagggactgc tttgggcata aatgagtgac   3300
tggttgggcg aggtgctgag gacctagctc agtggtggaa tgcttacagc atagtgtaca   3360
gaaggtttga tagtgtgttg tgtatatagg catggtacga tccactagtt ctagtagaca   3420
tgataagata acattgatga gtctagtgag tttggacaaa ccacaactag aatgcagtga   3480
aaaaaatgct ttatttgtga aatttgtgat gctattgctt tatttgtaac cattataagc   3540
tgcaataaac aagttccgag tttgtcagaa agcagaccaa acagcggttg gaataatagc   3600
gagaacagag aaatagcggc aaaaaataata cccgtatcac ttttgctgat atggttgatg   3660
tcatgtagcc aaatcgggaa aaacgggaag taggctccca tgataaaaaa gtaaaagaaa   3720
aagaataaac cgaacatcca aaagtttgtg ttttttaaat agtacataat ggatttcctt   3780
acgcgaaata cgggcagaca tggcctgccc ggttattatt atttttgaca ccagaccaac   3840
tggtaatggt agcgaccggc gctcagctgg aattccgccg atactgacgg gctccaggag   3900
tcgtcgccac caatccccat atggaaaccg tcgatattca gccatgtgcc ttcttccgcg   3960
tgcagcagat ggcgatggct ggtttccatc agttgctgtt gactgtagcg gctgatgttg   4020
aactggaagt cgccgcgcca ctggtgtggg ccataattca attcgcgcgt cccgcagcgc   4080
agaccgtttt cgctcgggaa gacgtacggg gtatacatgt ctgacaatgg cagatcccag   4140
cggtcaaaac aggcggcagt aaggcggtcg ggatagtttt cttgcggccc taatccgagc   4200
cagtttaccc gctctgctac ctgcgccagc tggcagttca ggccaatccg cgccggatgc   4260
ggtgtatcgc tcgccacttc aacatcaacg gtaatcgcca tttgaccact accatcaatc   4320
cggtaggttt tccggctgat aaataaggtt ttcccctgat gctgccacgc gtgagcggtc   4380
gtaatcagca ccgcatcagc aagtgtatct gccgtgcact gcaacaacgc tgcttcggcc   4440
tggtaatggc ccgccgcctt ccagcgttcg acccaggcgt tagggtcaat gcgggtcgct   4500
tcacttacgc caatgtcgtt atccagcggt gcacgggtga actgatcgcg cagcggcgtc   4560
agcagttgtt ttttatcgcc aatccacatc tgtgaaagaa agcctgactg gcggttaaat   4620
tgccaacgct tattacccag ctcgatgcaa aaatccattt cgctggtggt cagatgcggg   4680
atggcgtggg acgcggcggg gagcgtcaca ctgaggtttt ccgccagacg ccactgctgc   4740
```

-continued

```
caggcgctga tgtgcccggc ttctgaccat gcggtcgcgt tcggttgcac tacgcgtact   4800
gtgagccaga gttgcccggc gctctccggc tgcggtagtt caggcagttc aatcaactgt   4860
ttaccttgtg gagcgacatc cagaggcact tcaccgcttg ccagcggctt accatccagc   4920
gccaccatcc agtgcaggag ctcgttatcg ctatgacgga acaggtattc gctggtcact   4980
tcgatggttt gcccggataa acggaactgg aaaaactgct gctggtgttt tgcttccgtc   5040
agcgctggat gcggcgtgcg gtcggcaaag accagaccgt tcatacagaa ctggcgatcg   5100
ttcggcgtat cgccaaaatc accgccgtaa gccgaccacg ggttgccgtt ttcatcatat   5160
ttaatcagcg actgatccac ccagtcccag acgaagccgc cctgtaaacg gggatactga   5220
cgaaacgcct gccagtattt agcgaaaccg ccaagactgt tacccatcgc gtgggcgtat   5280
tcgcaaagga tcagcgggcg cgtctctcca ggtagcgaaa gccatttttt gatggaccat   5340
ttcggcacag ccgggaaggg ctggtcttca tccacgcgcg cgtacatcgg gcaaataata   5400
tcggtggccg tggtgtcggc tccgccgcct tcatactgca ccgggcggga aggatcgaca   5460
gatttgatcc agcgatacag cgcgtcgtga ttagcgccgt ggcctgattc attccccagc   5520
gaccagatga tcacactcgg gtgattacga tcgcgctgca ccattcgcgt tacgcgttcg   5580
ctcatcgccg gtagccagcg cggatcatcg gtcagacgat tcattggcac catgccgtgg   5640
gtttcaatat tggcttcatc caccacatac aggccgtagc ggtcgcacag cgtgtaccac   5700
agcggatggt tcggataatg cgaacagcgc acggcgttaa agttgttctg cttcatcagc   5760
aggatatcct gcaccatcgt ctgctcatcc atgacctgac catgcagagg atgatgctcg   5820
tgacggttaa cgcctcgaat cagcaacggc ttgccgttca gcagcagcag accattttca   5880
atccgcacct cgcggaaacc gacatcgcag gcttctgctt caatcagcgt gccgtcggcg   5940
gtgtgcagtt caaccaccgc acgatagaga ttcgggattt cggcgctcca cagtttcggg   6000
ttttcgacgt tcagacgtag tgtgacgcga tcggcataac caccacgctc atcgataatt   6060
tcaccgccga aaggcgcggt gccgctggcg acctgcgttt caccctgcca taaagaaact   6120
gttacccgta ggtagtcacg caactcgccg cacatctgaa cttcagcctc cagtacagcg   6180
cggctgaaat catcattaaa gcgagtggca acatggaaat cgctgatttg tgtagtcggt   6240
ttatgcagca acgagacgtc acggaaaatg ccgctcatcc gccacatatc ctgatcttcc   6300
agataactgc cgtcactcca acgcagcacc atcaccgcga ggcggttttc tccggcgcgt   6360
aaaaatgcgc tcaggtcaaa ttcagacggc aaacgactgt cctggccgta accgacccag   6420
cgcccgttgc accacagatg aaacgccgag ttaacgccat caaaaataat tcgcgtctgg   6480
ccttcctgta gccagctttc atcaacatta aatgtgagcg agtaacaacc cgtcggattc   6540
tccgtgggaa caaacggcgg attgaccgta atgggatagg ttacgttggt gtagatgggc   6600
gcatcgtaac cgtgcatctg ccagtttgag gggacgacga cagtatcggc ctcaggaaga   6660
tcgcactcca gccagctttc cggcaccgct tctggtgccg gaaaccaggc aaagcgccat   6720
tcgccattca ggctgcgcaa ctgttgggaa gggcgatcgg tgcgggcctc ttcgctatta   6780
cgccagctgg cgaaaggggg atgtgctgca aggcgattaa gttgggtaac gccagggttt   6840
tcccagtcac gacgttgtaa aacgacggcc agtgccaagc ttggactcaa aaaacttagc   6900
aattctgaag gaaagtcctt ggggtcttct acctttctct tcttttttag cggaattccg   6960
gaaaacttta tccatactag atgtctccac cgctgaatga aaagcagcat gagaagataa   7020
gcagaagctg agcagaagca ccctcatccc atggcctctc tttcttggga cctgctggtg   7080
accgctgttg tcacccttgt gcataagccc ttaacaggta ctccctggaa agcccagacc   7140
```

-continued

```
accactcttt gtagcttgtt gggatttcag gccccaccac tgcccccctac cccatcccca   7200
cccccataaa gccaactctt ctacattaac gttcaattct gcaaattcca ggccaaggac   7260
cggataactt cgtatagcat acattatacg aagttatgcg gccgggaagt tcctattctc   7320
tagaaagtat aggaacttcg cggccaattc taccgggtag gggaggcgct tttcccaagg   7380
cagtctggag catgcgcttt agcagccccg ctgggcactt ggcgctacac aagtggcctc   7440
tggcctcgca cacattccac atccaccggt aggcgccaac cggctccgtt ctttggtggc   7500
cccttcgcgc caccttctac tcctccccta gtcaggaagt tcccccccgc cccgcagctc   7560
gcgtcgtgca ggacgtgaca aatggaagta gcacgtctca ctagtctcgt gcagatggac   7620
agcaccgctg agcaatggaa gcgggtaggc ctttggggca gcggccaata gcagctttgc   7680
tccttcgctt tctgggctca gaggctggga aggggtgggt ccgggggcgg gctcaggggc   7740
gggctcaggg gcgggcgggc gcccgaaggt cctccggagg cccggcattc tgcacgcttc   7800
aaaagcgcac gtctgcgcgc tgttctcctc ttcctcatct ccgggccttt cgacctgcag   7860
ccaatatggg atcggccatt gaacaagatg gattgcacgc aggttctccg gccgcttggg   7920
tggagaggct attcggctat gactgggcac aacagacaat cggctgctct gatgccgccg   7980
tgttccggct gtcagcgcag gggcgcccgg ttctttttgt caagaccgac ctgtccggtg   8040
ccctgaatga actgcaggac gaggcagcgc ggctatcgtg gctggccacg acgggcgttc   8100
cttgcgcagc tgtgctcgac gttgtcactg aagcgggaag ggactggctg ctattgggcg   8160
aagtgccggg gcaggatctc ctgtcatctc accttgctcc tgccgagaaa gtatccatca   8220
tggctgatgc aatgcggcgg ctgcatacgc ttgatccggc tacctgccca ttcgaccacc   8280
aagcgaaaca tcgcatcgag cgagcacgta ctcggatgga agccggtctt gtcgatcagg   8340
atgatctgga cgaagagcat caggggctcg cgccagccga actgttcgcc aggctcaagg   8400
cgcgcatgcc cgacggcgag gatctcgtcg tgacccatgg cgatgcctgc ttgccgaata   8460
tcatggtgga aaatggccgc ttttctggat tcatcgactg tggccggctg ggtgtggcgg   8520
accgctatca ggacatagcg ttggctaccc gtgatattgc tgaagagctt ggcggcgaat   8580
gggctgaccg cttcctcgtg ctttacggta tcgccgctcc cgattcgcag cgcatcgcct   8640
tctatcgcct tcttgacgag ttcttctgag gggatccgct gtaagtctgc agaaattgat   8700
gatctattaa acaataaaga tgtccactaa aatggaagtt tttcctgtca tactttgtta   8760
agaagggtga gaacagagta cctacatttt gaatggaagg attggagcta cgggggtggg   8820
ggtggggtgg gattagaata aatgcctgct ctttactgaa ggctctttac tattgcttta   8880
tgataatgtt tcatagttgg atatcataat ttaaacaagc aaaaccaatt aagggccagc   8940
tcattcctcc cactcatgat ctatagatct atagatctct cgtgggatca ttgtttttct   9000
cttgattccc actttgtggt tctaagtact gtggtttcca aatgtgtcag tttcatagcc   9060
tgaagaacga gatcagcagc ctctgttcca catacacttc attctcagta ttgttttgcc   9120
aagttctaat tccatcagaa gctcgatacc gtcgaggaag ttcctattct ctagaaagta   9180
taggaacttc ccggccggga agttcctata ctttctagag aataggaact tcccggccgc   9240
caccgcggag atctcaccat cgacccataa cttcgtatag tatacattat acgaagttat   9300
taccatgcgt attcacacac acacacaaac acacaacaca cacgcacgac acgactggtc   9360
aggtctagct agggccaatt gttttgcttg agaaatactg gtattcccag caccctgttt   9420
agtgacactc ctgcttccaa attcagggct tcttcagacg cagcattcag aaaaacatgg   9480
```

-continued

```
tgtatacatg tcaccgtgac aaaaactgta tcatcaacaa ggtcaccaga aatcgatgcc   9540
agtactgcag gctacaaaag tgtttcgaag tgggcatgtc caaggaaggt aggctctctc   9600
ctatcctgtc ctatcgtgtc gtgcggttgt ccactttgcc gtccagcttc cctgaccctg   9660
agatctcgcc tgccctgtaa ctgctttctt ctccaagacc attcccatta gattagctct   9720
cttcaccctg tagcttctgt ttggtggagc aggagggttg ggctcatccc ttccctctcc   9780
tgttctttca caggacagat cctgagatgg ctctgactgg cccctccttt ccactccccc   9840
cccccaccat tgtgctgcca aggctataag tggatatcct gcctgcatat cctgcccccc   9900
tccaaccccc agctcctgca gggcaaccgg aagggcagga tggagccgaa ttggcctggg   9960
gagggagcat ggctgtaggc tctgggtggg gctggggcaa accagcctgg aaataggaga  10020
ttatgtagca gagagggaaa ctaaggcact aatacgtatt tttaaagaga actgagccca  10080
ttaagctagg atgagagaag acgcccatca ggagaatttg agccgggcgt ggtggcacac  10140
gcctttaatc ccagcactcg ggaggcagag gcaggcggat ttctgagttc aaggccagcc  10200
tggtctacaa agtgagttcc aggacagcca gggctataca gagaaaccct gattcaaaaa  10260
accaaaaaaa aaaaaaaaaa aaaaagaaag aaaagaaaaa acaggagggt cctgaggatc  10320
ctgatccttc tttttgcctc caaccccaag ctgtaaggaa cgatcgaaac aagaagaaaa  10380
aggaggtaaa agaggagggc tcgcccgaca gctatgaact gagtccacag ttagaggaac  10440
tcatcaccaa ggtcagcaaa gcccaccagg agacttttcc ctcactctgc cagctgggca  10500
agtacaccac ggtgaggagt gggcagagtc tgggtgaggg cctcaggaac gggcagtggg  10560
gagagtgccc agggaagcct tcacggctca cttcacccct gcagaactcc agtgcagatc  10620
accgggtgca gctggacctg gggctgtggg acaagttcag cgagctggcc accaaatgca  10680
tcatcaagat tgtggagttt gcgaagcggc tgcctggttt tacagggctc agcattgccg  10740
accagatcac gctgctcaag gctgcttgtc tggacatcct agtgagttag gcagatgagt  10800
tctggaccac tctgaccctt ttccaccacc acccccacca caccctttag ccctctcctc  10860
cacctaagct ctttttgtct tagcagttcc ctcctggttt gcctaccctc ccctttccaa  10920
tctcaagagt cccacctctc cgccttactc ctccagttca ggctttcctt actgggaacc  10980
aaactcactt aggaatcctt cctcaggagc agtactaacc gttttcctta cccccaccct  11040
ccagatgctg cggatctgta caaggtatac cccagagcag gacactatga cattctcgga  11100
tgggctgacc ctgaaccgaa cccagatgca caatgctggc tttgggcccc ttacagacct  11160
cgtctttgcc tttgccgggc agctgctgcc cctggagatg gatgacaccg agactgggct  11220
acttagtgct atctgcctca tctgtggagg tgcgggggcg ccccctggtg tctacatggg  11280
ctccctctcc caccagactc tatccagacc ctatccccac tctgaccagg tggcaggtcg  11340
tctttttccc tgggaattgt tcctacagac ttctcagctt atgtatagtc tttctggcta  11400
accaggctaa gggaaaaaga aggaggcaga gtccggagaa cgcagaagcc ctggatacag  11460
tgctgagata ggaatttaat gggagtgata ttctagagca gcatcattgc tgaggagtaa  11520
acacaggcc  ttatgtcagg ggagctaacc tggagggcta agtgacagga gtaaagagtg  11580
gatgagatag ctttgaggcc ctccaagtaa ggtctgtcag gcgtcagccg cctgtcactg  11640
tgtcctaccg tgcctcatcc aatctccttg tgtagaccga atggacctgg aagagcccga  11700
gaaggtggac aagctgcagg agcccctgct ggaagccctg aggctctatg cccggcgacg  11760
gagacccagc caaccctaca tgttcccaag gatgctgatg aaaatcaccg acctccgggg  11820
catcagcact aagggttagt tctgagtcaa ctctctctcc ctccccagat ctgcaggtct  11880
```

-continued

```
cctgagtcac acaggtggac aggcacaggc agggggagag aggaaccgag aatccagcaa  11940
cctccatgga gtcctggtgt gtgtgtgttt gtgtgtgttg ctcggagagg aaccttgtac  12000
catccataaa ctaggcaaat gctatctgac aacctagctt cctttacttt ttatcattta  12060
tttatttatt atatgtaagt accctgtagc tgtcttcaga cacaccagaa gaaggcatca  12120
gatctcatta cggatggttg tgagccacca tgtggttgct gggaattgaa ttcccgggtc  12180
gactcgagcg gccgcatcgt gactgactga cgatctgcct cgcgcgtttc ggtgatgacg  12240
gtgaaaacct ctgacacatg cagctcccgg agacggtcac agcttgtctg taagcggatg  12300
ccgggagcag acaagcccgt cagggcgcgt cagcgggtgt tggcgggtgt cggggcgcag  12360
ccatgaccca gtcacgtagc gatagcggag tgtataattc ttgaagacga aagggcctcg  12420
tgatacgcct atttttatag gttaatgtca tgataataat ggtttcttag acgtcaggtg  12480
gcacttttcg gggaaatgtg cgcggaaccc ctatttgttt atttttctaa atacattcaa  12540
atatgtatcc gctcatgaga caataaccct gataaatgct tcaataatat tgaaaaagga  12600
agagtatgag tattcaacat ttccgtgtcg cccttattcc cttttttgcg gcattttgcc  12660
ttcctgtttt tgctcaccca gaaacgctgg tgaaagtaaa agatgctgaa gatcagttgg  12720
gtgcacgagt gggttacatc gaactggatc tcaacagcgg taagatcctt gagagttttc  12780
gccccgaaga acgttttcca atgatgagca cttttaaagt tctgctatgt ggcgcggtat  12840
tatcccgtgt tgacgccggg caagagcaac tcggtcgccg catacactat tctcagaatg  12900
acttggttga gtactcacca gtcacagaaa agcatcttac ggatggcatg acagtaagag  12960
aattatgcag tgctgccata accatgagtg ataacactgc ggccaactta cttctgacaa  13020
cgatcggagg accgaaggag ctaaccgctt ttttgcacaa catgggggat catgtaactc  13080
gccttgatcg ttgggaaccg gagctgaatg aagccatacc aaacgacgag cgtgacacca  13140
cgatgcctgc agcaatggca acaacgttgc gcaaactatt aactggcgaa ctacttactc  13200
tagcttcccg gcaacaatta atagactgga tggaggcgga taaagttgca ggaccacttc  13260
tgcgctcggc ccttccggct ggctggttta ttgctgataa atctggagcc ggtgagcgtg  13320
ggtctcgcgg tatcattgca gcactggggc cagatggtaa gccctcccgt atcgtagtta  13380
tctacacgac ggggagtcag gcaactatgg atgaacgaaa tagacagatc gctgagatag  13440
gtgcctcact gattaagcat tggtaactgt cagaccaagt ttactcatat atactttaga  13500
ttgatttaaa acttcatttt taatttaaaa ggatctaggt gaagatcctt tttgataatc  13560
tcatgaccaa aatcccttaa cgtgagtttt cgttccactg agcgtcagac cccgtagaaa  13620
agatcaaagg atcttcttga gatccttttt ttctgcgcgt aatctgctgc ttgcaaacaa  13680
aaaaaccacc gctaccagcg gtggtttgtt tgccggatca agagctacca actctttttc  13740
cgaaggtaac tggcttcagc agagcgcaga taccaaatac tgtccttcta gtgtagccgt  13800
agttaggcca ccacttcaag aactctgtag caccgcctac atacctcgct ctgctaatcc  13860
tgttaccagt ggctgctgcc agtggcgata agtcgtgtct taccgggttg gactcaagac  13920
gatagttacc ggataaggcg cagcggtcgg gctgaacggg gggttcgtgc acacagccca  13980
gcttggagcg aacgacctac accgaactga gatacctaca gcgtgagcta tgagaaagcg  14040
ccacgcttcc cgaagggaga aaggcggaca ggtatccggt aagcggcagg gtcggaacag  14100
gagagcgcac gagggagctt ccagggggaa acgcctggta tctttatagt cctgtcgggt  14160
ttcgccacct ctgacttgag cgtcgatttt tgtgatgctc gtcagggggg cggagcctat  14220
```

-continued

```
ggaaaaacgc cagcaacgcg gcctttttac ggttcctggc cttttgctgg ccttttgctc  14280
acatgttctt tcctgcgtta tcccctgatt ctgtggataa ccgtattacc gcctttgagt  14340
gagctgatac cgctcgccgc agccgaacga ccgagcgcag cgagtcagtg agcgaggaag  14400
cggaagagcg cctgatgcgg tattttctcc ttacgcatct gtgcggtatt tcacaccgca  14460
taaattccga caccatcgaa tggtgcaaaa cctttcgcgg tatggcatga tagcgcccgg  14520
aagagagtca attcagggtg gtgaatgtga aaccagtaac gttatacgat gtcgcagagt  14580
atgccggtgt ctcttatcag accgtttccc gcgtggtgaa ccaggccagc cacgtttctg  14640
cgaaaacgcg ggaaaaagtg gaagcggcga tggcggagct gaattacatt cccaaccgcg  14700
tggcacaaca actggcgggc aaacagtcgt tgctgattgg cgttgccacc tccagtctgg  14760
ccctgcacgc gccgtcgcaa attgtcgcgg cgattaaatc tcgcgccgat caactgggtg  14820
ccagcgtggt ggtgtcgatg gtagaacgaa gcggcgtcga agcctgtaaa gcggcggtgc  14880
acaatcttct cgcgcaacgc gtcagtgggc tgatcattaa ctatccgctg gatgaccagg  14940
atgccattgc tgtggaagct gcctgcacta atgttccggc gttatttctt gatgtctctg  15000
accagacacc catcaacagt attattttct cccatgaaga cggtacgcga ctgggcgtgg  15060
agcatctggt cgcattgggt caccagcaaa tcgcgctgtt agcgggccca ttaagttctg  15120
tctcggcgcg tctgcgtctg gctggctggc ataaatatct cactcgcaat caaattcagc  15180
cgatagcgga acgggaaggc gactggagtg ccatgtccgg ttttcaacaa accatgcaaa  15240
tgctgaatga gggcatcgtt cccactgcga tgctggttgc caacgatcag atggcgctgg  15300
gcgcaatgcg cgccattacc gagtccgggc tgcgcgttgg tgcggatatc tcggtagtgg  15360
gatacgacga taccgaagac agctcatgtt atatcccgcc gttaaccacc atcaaacagg  15420
attttcgcct gctggggcaa accagcgtgg accgcttgct gcaactctct cagggccagg  15480
cggtgaaggg caatcagctg ttgcccgtct cactggtgaa aagaaaaacc accctggcgc  15540
ccaatacgca aaccgcctct ccccgcgcgt tggccgattc attaatgcag ctggcacgac  15600
aggtttcccg actggaaagc gggcagtgag cgcaacgcaa ttaatgtgag ttagctcact  15660
cattaggcac cccaggcttt acactttatg cttccggctc gtatgttgtg tggaattgtg  15720
agcggataac aatttcacac aggaaacagc tatgaccatg attacggatt cactggccgt  15780
cgttttacaa cgtcgtgact gggaaaaccc tggcgttacc caacttaatc gccttgcagc  15840
acatccccct ttcgccagct ggcgtaatag cgaagaggcc cgcaccgatc gcccttccca  15900
acagttgcgc agcctgaatg gcgaatggcg ctttgcctgg tttccggcac cagaagcggt  15960
gccggaaagc tggctggagt gcgatcttcc tgaggccgat actgtcgtcg tcccctcaaa  16020
ctggcagatg cacggttacg atgcgcccat ctacaccaac gtaacctatc ccattacggt  16080
caatccgccg tttgttccca cggagaatcc gacgggttgt tactcgctca catttaatgt  16140
tgatgaaagc tggctacagg aaggccagac gcgaattatt tttgatggcg ttggaattac  16200
gttatcgact gcacggtgca ccaatgcttc tggcgtcagg cagccatcgg aagctgtggt  16260
atggctgtgc aggtcgtaaa tcactgcata attcgtgtcg ctcaaggcgc actcccgttc  16320
tggataatgt tttttgcgcc gacatcataa cggttctggc aaatattctg aaatgagctg  16380
ttgacaatta atcatcggct cgtataatgt gtggaattgt gagcggataa caatttcaca  16440
caggaaacag tattcatgtc ccctatacta ggttattgga aaattaaggg ccttgtgcaa  16500
cccactcgac ttcttttgga atatcttgaa gaaaaatatg aagagcattt gtatgagcgc  16560
gatgaaggtg ataaatggcg aaacaaaaag tttgaattgg gtttggagtt tcccaatctt  16620
```

-continued

```
ccttattata ttgatggtga tgttaaatta acacagtcta tggccatcat acgttatata  16680

gctgacaagc acaacatgtt gggtggttgt ccaaaagagc gtgcagagat ttcaatgctt  16740

gaaggagcgg ttttggatat tagatacggt gtttcgagaa ttgcatatag taaagacttt  16800

gaaactctca aagttgattt tcttagcaag ctacctgaaa tgctgaaaat gttcgaagat  16860

cgtttatgtc ataaaacata tttaaatggt gatcatgtaa cccatcctga cttcatgttg  16920

tatgacgctc ttgatgttgt tttatacatg gacccaatgt gcctggatgc gttcccaaaa  16980

ttagtttgtt ttaaaaaacg tattgaagct atcccacaaa ttgataagta cttgaaatcc  17040

agcaagtata tagcatggcc tttgcagggc tggcaagcca cgtttggtgg tggcgaccat  17100

cctccaaaat cggatctggt tccgcgtgga tcccc                             17135
```

<210> SEQ ID NO 56
<211> LENGTH: 8934
<212> TYPE: DNA
<213> ORGANISM: Artificial sequence
<220> FEATURE:
<223> OTHER INFORMATION: Description of Artificial sequence: DNA sequence of plasmid pJMG
<220> FEATURE:
<223> OTHER INFORMATION: Position 1 to 2240 vector sequence
<220> FEATURE:
<223> OTHER INFORMATION: Position 2245 Frt site, sense
<220> FEATURE:
<223> OTHER INFORMATION: Position 2285 loxP1 site, sense
<220> FEATURE:
<223> OTHER INFORMATION: Position 2355 lox511 site, sense
<220> FEATURE:
<223> OTHER INFORMATION: Position 2400 to 5952 NLS-LacZ polyA gene, antisense
<220> FEATURE:
<223> OTHER INFORMATION: Position 5960 to 6549 IRES, antisense
<220> FEATURE:
<223> OTHER INFORMATION: Position 6550 to 7050 rabbit beta globin intron, antisense
<220> FEATURE:
<223> OTHER INFORMATION: Position 7060 loxP1 site, antisense
<220> FEATURE:
<223> OTHER INFORMATION: Position 7115 to 7630 PGK promotor, sense
<220> FEATURE:
<223> OTHER INFORMATION: Position 7638 to 8840 Neomycine resistance gene, sense
<220> FEATURE:
<223> OTHER INFORMATION: Position 8441 to 8480 synthetic splice donor site, sense
<220> FEATURE:
<223> OTHER INFORMATION: Position 8505 lox511 site, antisense
<220> FEATURE:
<223> OTHER INFORMATION: Position 8540 Frtm site, antisense
<220> FEATURE:
<223> OTHER INFORMATION: Position 8600 to 8934 vector sequence

<400> SEQUENCE: 56

```
gtggcacttt tcggggaaat gtgcgcggaa cccctatttg tttatttttc taaatacatt     60

caaatatgta tccgctcatg agacaataac cctgataaat gcttcaataa tattgaaaaa    120

ggaagagtat gagtattcaa catttccgtg tcgcccttat tccctttttt gcggcatttt    180

gccttcctgt ttttgctcac ccagaaacgc tggtgaaagt aaaagatgct gaagatcagt    240

tgggtgcacg agtgggttac atcgaactgg atctcaacag cggtaagatc cttgagagtt    300

ttcgccccga agaacgtttt ccaatgatga gcacttttaa agttctgcta tgtggcgcgg    360

tattatcccg tattgacgcc gggcaagagc aactcggtcg ccgcatacac tattctcaga    420

atgacttggt tgagtactca ccagtcacag aaaagcatct tacggatggc atgacagtaa    480

gagaattatg cagtgctgcc ataaccatga gtgataacac tgcggccaac ttacttctga    540
```

-continued

```
caacgatcgg aggaccgaag gagctaaccg ctttttgca caacatgggg gatcatgtaa    600
ctcgccttga tcgttgggaa ccggagctga atgaagccat accaaacgac gagcgtgaca    660
ccacgatgcc tgtagcaatg gcaacaacgt tgcgcaaact attaactggc gaactactta    720
ctctagcttc ccggcaacaa ttaatagact ggatggaggc ggataaagtt gcaggaccac    780
ttctgcgctc ggcccttccg gctggctggt ttattgctga taaatctgga gccggtgagc    840
gtgggtctcg cggtatcatt gcagcactgg ggccagatgg taagccctcc cgtatcgtag    900
ttatctacac gacggggagt caggcaacta tggatgaacg aaatagacag atcgctgaga    960
taggtgcctc actgattaag cattggtaac tgtcagacca agtttactca tatatacttt   1020
agattgattt aaaacttcat ttttaattta aaaggatcta ggtgaagatc ctttttgata   1080
atctcatgac caaaatccct taacgtgagt tttcgttcca ctgagcgtca gaccccgtag   1140
aaaagatcaa aggatcttct tgagatcctt tttttctgcg cgtaatctgc tgcttgcaaa   1200
caaaaaaacc accgctacca gcggtggttt gtttgccgga tcaagagcta ccaactcttt   1260
ttccgaaggt aactggcttc agcagagcgc agataccaaa tactgtcctt ctagtgtagc   1320
cgtagttagg ccaccacttc aagaactctg tagcaccgcc tacatacctc gctctgctaa   1380
tcctgttacc agtggctgct gccagtggcg ataagtcgtg tcttaccggg ttggactcaa   1440
gacgatagtt accggataag gcgcagcggt cgggctgaac ggggggttcg tgcacacagc   1500
ccagcttgga gcgaacgacc tacaccgaac tgagatacct acagcgtgag ctatgagaaa   1560
gcgccacgct tcccgaaggg agaaaggcgg acaggtatcc ggtaagcggc agggtcggaa   1620
caggagagcg cacgagggag cttccagggg gaaacgcctg gtatctttat agtcctgtcg   1680
ggtttcgcca cctctgactt gagcgtcgat ttttgtgatg ctcgtcaggg gggcggagcc   1740
tatggaaaaa cgccagcaac gcggcctttt tacggttcct ggccttttgc tggccttttg   1800
ctcacatgtt ctttcctgcg ttatcccctg attctgtgga taaccgtatt accgcctttg   1860
agtgagctga taccgctcgc cgcagccgaa cgaccgagcg cagcgagtca gtgagcgagg   1920
aagcggaaga gcgcccaata cgcaaaccgc ctctccccgc gcgttggccg attcattaat   1980
gcagctggca cgacaggttt cccgactgga aagcgggcag tgagcgcaac gcaattaatg   2040
tgagttagct cactcattag gcaccccagg ctttacactt tatgcttccg gctcgtatgt   2100
tgtgtggaat tgtgagcgga taacaatttc acacaggaaa cagctatgac catgattacg   2160
ccaagcgcgc aattaaccct cactaaaggg aacaaaagct ggagctccac cgcggtggcg   2220
gccgctctac gaggaattca accagaagtt cctattctct agaaagtata ggaacttcca   2280
gctcataact tcgtataatg tatgctatac gaagttatcc aagcatcacc atatgcaaat   2340
gcctaccgga ccatcataac ttcgtataat gtatactata cgaagttata agctctagtt   2400
ctagtagaca tgataagata cattgatgag tttggacaaa ccacaactag aatgcagtga   2460
aaaaaatgct ttatttgtga aatttgtgat gctattgctt tatttgtaac cattataagc   2520
tgcaataaac aagttccgag tttgtcagaa agcagaccaa acagcggttg gaataatagc   2580
gagaacagag aaatagcggc aaaaaataata cccgtatcac ttttgctgat atggttgatg   2640
tcatgtagcc aaatcgggaa aaacgggaag taggctccca tgataaaaaa gtaaaagaaa   2700
aagaataaac cgaacatcca aaagtttgtg ttttttaaat agtacataat ggatttcctt   2760
acgcgaaata cgggcagaca tggcctgccc ggttattatt atttttgaca ccagaccaac   2820
tggtaatggt agcgaccggc gctcagctgg aattccgccg atactgacgg gctccaggag   2880
```

-continued tcgtcgccac caatccccat atggaaaccg tcgatattca gccatgtgcc ttcttccgcg 2940
tgcagcagat ggcgatggct ggtttccatc agttgctgtt gactgtagcg gctgatgttg 3000
aactggaagt cgccgcgcca ctggtgtggg ccataattca attcgcgcgt cccgcagcgc 3060
agaccgtttt cgctcgggaa gacgtacggg gtatacatgt ctgacaatgg cagatcccag 3120
cggtcaaaac aggcggcagt aaggcggtcg ggatagtttt cttgcggccc taatccgagc 3180
cagtttaccc gctctgctac ctgcgccagc tggcagttca ggccaatccg cgccggatgc 3240
ggtgtatcgc tcgccacttc aacatcaacg gtaatcgcca tttgaccact accatcaatc 3300
cggtaggttt tccggctgat aaataaggtt ttcccctgat gctgccacgc gtgagcggtc 3360
gtaatcagca ccgcatcagc aagtgtatct gccgtgcact gcaacaacgc tgcttcggcc 3420
tggtaatggc ccgccgcctt ccagcgttcg acccaggcgt tagggtcaat gcgggtcgct 3480
tcacttacgc caatgtcgtt atccagcggt gcacgggtga actgatcgcg cagcggcgtc 3540
agcagttgtt ttttatcgcc aatccacatc tgtgaaagaa agcctgactg gcggttaaat 3600
tgccaacgct tattacccag ctcgatgcaa aaatccattt cgctggtggt cagatgcggg 3660
atggcgtggg acgcggcggg gagcgtcaca ctgaggtttt ccgccagacg ccactgctgc 3720
caggcgctga tgtgcccggc ttctgaccat gcggtcgcgt tcggttgcac tacgcgtact 3780
gtgagccaga gttgcccggc gctctccggc tgcggtagtt caggcagttc aatcaactgt 3840
ttaccttgtg gagcgacatc cagaggcact tcaccgcttg ccagcggctt accatccagc 3900
gccaccatcc agtgcaggag ctcgttatcg ctatgacgga acaggtattc gctggtcact 3960
tcgatggttt gcccggataa acggaactgg aaaaactgct gctggtgttt tgcttccgtc 4020
agcgctggat gcggcgtgcg gtcggcaaag accagaccgt tcatacagaa ctggcgatcg 4080
ttcggcgtat cgccaaaatc accgccgtaa gccgaccacg ggttgccgtt ttcatcatat 4140
ttaatcagcg actgatccac ccagtcccag acgaagccgc cctgtaaacg gggatactga 4200
cgaaacgcct gccagtattt agcgaaaccg ccaagactgt tacccatcgc gtgggcgtat 4260
tcgcaaagga tcagcgggcg cgtctctcca ggtagcgaaa gccatttttt gatggaccat 4320
ttcggcacag ccgggaaggg ctggtcttca tccacgcgcg cgtacatcgg gcaaataata 4380
tcggtggccg tggtgtcggc tccgccgcct tcatactgca ccgggcggga aggatcgaca 4440
gatttgatcc agcgatacag cgcgtcgtga ttagcgccgt ggcctgattc attccccagc 4500
gaccagatga tcacactcgg gtgattacga tcgcgctgca ccattcgcgt tacgcgttcg 4560
ctcatcgccg gtagccagcg cggatcatcg gtcagacgat tcattggcac catgccgtgg 4620
gtttcaatat tggcttcatc caccacatac aggccgtagc ggtcgcacag cgtgtaccac 4680
agcggatggt tcggataatg cgaacagcgc acggcgttaa agttgttctg cttcatcagc 4740
aggatatcct gcaccatcgt ctgctcatcc atgacctgac catgcagagg atgatgctcg 4800
tgacggttaa cgcctcgaat cagcaacggc ttgccgttca gcagcagcag accattttca 4860
atccgcacct cgcggaaacc gacatcgcag gcttctgctt caatcagcgt gccgtcggcg 4920
gtgtgcagtt caaccaccgc acgatagaga ttcgggattt cggcgctcca cagtttcggg 4980
ttttcgacgt tcagacgtag tgtgacgcga tcggcataac caccacgctc atcgataatt 5040
tcaccgccga aaggcgcggt gccgctggcg acctgcgttt caccctgcca taaagaaact 5100
gttacccgta ggtagtcacg caactcgccg cacatctgaa cttcagcctc cagtacagcg 5160
cggctgaaat catcattaaa gcgagtggca acatggaaat cgctgatttg tgtagtcggt 5220
ttatgcagca acgagacgtc acggaaaatg ccgctcatcc gccacatatc ctgatcttcc 5280

-continued

```
agataactgc cgtcactcca acgcagcacc atcaccgcga ggcggttttc tccggcgcgt   5340
aaaaatgcgc tcaggtcaaa ttcagacggc aaacgactgt cctggccgta accgacccag   5400
cgcccgttgc accacagatg aaacgccgag ttaacgccat caaaaataat tcgcgtctgg   5460
ccttcctgta gccagctttc atcaacatta aatgtgagcg agtaacaacc cgtcggattc   5520
tccgtgggaa caaacggcgg attgaccgta atgggatagg ttacgttggt gtagatgggc   5580
gcatcgtaac cgtgcatctg ccagtttgag gggacgacga cagtatcggc ctcaggaaga   5640
tcgcactcca gccagctttc cggcaccgct tctggtgccg gaaaccaggc aaagcgccat   5700
tcgccattca ggctgcgcaa ctgttgggaa gggcgatcgg tgcgggcctc ttcgctatta   5760
cgccagctgg cgaaaggggg atgtgctgca aggcgattaa gttgggtaac gccagggttt   5820
tcccagtcac gacgttgtaa aacgacggcc agtgccaagc ttggactcaa aaaacttagc   5880
aattctgaag gaaagtcctt ggggtcttct acctttctct tctttttgc ggaattccgg   5940
aaaactttat ccatggttgt ggctagctta tcattgtgtt tttcaaagga aaaccacgtc   6000
cccgtggttc ggggggccta gacgtttttt taacctcgac taaacacatg taaagcatgt   6060
gcaccgaggc cccagatcag atcccataca atggggtacc ttctgggcat ccttcagccc   6120
cttgttgaat acgcttgagg agagccattt gactctttcc acaactatcc aactcacaac   6180
gtggcactgg ggttgtgccg cctttgcagg tgtatcttat acacgtggct tttggccgca   6240
gaggcacctg tcgccaggtg gggggttccg ctgcctgcaa agggtcgcta cagacgttgt   6300
ttgtcttcaa gaagcttcca gaggaactgc ttccttcacg acattcaaca gaccttgcat   6360
tcctttggcg agaggggaaa gacccctagg aatgctcgtc aagaagacag ggccaggttt   6420
ccgggccctc acattgccaa aagacggcaa tatggtggaa aataacatat agacaaacgc   6480
acaccggcct tattccaagc ggcttcggcc agtaacgtta gggggggggg agggagaggg   6540
gcggaattcc ctatagtgag tcgtattaca attctttgcc aaaatgatga gacagcacaa   6600
taaccagcac gttgcccagg agctgtagga aaaagaagaa ggcatgaaca tggttagcag   6660
aggggcccgg tttggactca gagtatttta tcctcatctc aaacagtgta tatcattgta   6720
accataaaga gaaaggcagg atgatgacca ggatgtagtt gtttctacca ataagaatat   6780
ttccacgcca gccagaattt atatgcagaa atattctacc ttatcattta attataacaa   6840
ttgttctcta aaactgtgct gaagtacaat ataatatacc ctgattgcct tgaaaaaaaa   6900
gtgattagag aaagtactta caatctgaca aataaacaaa agtgaattta aaaattcgtt   6960
acaaatgcaa gctaaagttt aacgaaaaag ttacagaaaa tgaaaagaaa ataagaggag   7020
acaatggttg tcaacagagt gcaaattcca ggccaaggaa taacttcgta tagcatacat   7080
tatacgaagt tatgcggccg atccccgggc tgcaggaatt ctaccgggta ggggaggcgc   7140
ttttcccaag gcagtctgga gcatgcgctt tagcagcccc gctgggcact tggcgctaca   7200
caagtggcct ctggcctcgc acacattcca catccaccgg taggcgccaa ccggctccgt   7260
tctttggtgg ccccttcgcg ccaccttcta ctcctcccct agtcaggaag ttcccccccg   7320
ccccgcagct cgcgtcgtgc aggacgtgac aaatggaagt agcacgtctc actagtctcg   7380
tgcagatgga cagcaccgct gagcaatgga agcgggtagg cctttggggc agcggccaat   7440
agcagctttg ctccttcgct ttctgggctc agaggctggg aaggggtggg tccgggggcg   7500
ggctcagggg cgggctcagg ggcggggcgg gcgcccgaag gtcctccgga gcccggcatt   7560
ctgcacgctt caaaagcgca cgtctgccgc gctgttctcc tcttcctcat ctccgggcct   7620
```

-continued

```
ttcgacctgc agccaatatg ggatcggcca ttgaacaaga tggattgcac gcaggttctc   7680
cggccgcttg ggtggagagg ctattcggct atgactgggc acaacagaca atcggctgct   7740
ctgatgccgc cgtgttccgg ctgtcagcgc aggggcgccc ggttcttttt gtcaagaccg   7800
acctgtccgg tgccctgaat gaactgcagg acgaggcagc gcggctatcg tggctggcca   7860
cgacgggcgt tccttgcgca gctgtgctcg acgttgtcac tgaagcggga agggactggc   7920
tgctattggg cgaagtgccg gggcaggatc tcctgtcatc tcaccttgct cctgccgaga   7980
aagtatccat catggctgat gcaatgcggc ggctgcatac gcttgatccg gctacctgcc   8040
cattcgacca ccaagcgaaa catcgcatcg agcgagcacg tactcggatg gaagccggtc   8100
ttgtcgatca ggatgatctg gacgaagagc atcaggggct cgcgccagcc gaactgttcg   8160
ccaggctcaa ggcgcgcatg cccgacggcg aggatctcgt cgtgacccat ggcgatgcct   8220
gcttgccgaa tatcatggtg gaaaatggcc gcttttctgg attcatcgac tgtggccggc   8280
tgggtgtggc ggaccgctat caggacatag cgttggctac ccgtgatatt gctgaagagc   8340
ttggcggcga atgggctgac cgcttcctcg tgctttacgg tatcgccgct cccgattcgc   8400
agcgcatcgc cttctatcgc cttcttgacg agttcttctg actgtaaaac gacggccagt   8460
caggtaagtc tcgagcgggc gatatcaagc ttatcgatac cggtataact tcgtatagta   8520
tacattatac gaagttatga gaagttccta atctatttga agtataggaa cttcgcggcc   8580
gcatcgacct cgaggggggg cccgggcttt ccccgtcaag ctctaaatcg gggctccct   8640
ttagggttcc gatttagtgc tttacggcac ctcgacccca aaaaacttga ttagggtgat   8700
ggttcacgta gtgggccatc gccctgatag acggtttttc gccctttgac gttggagtcc   8760
acgttcttta atagtggact cttgttccaa actggaacaa cactcaaccc tatctcggtc   8820
tattcttttg atttataagg gattttgccg atttcggcct attggttaaa aaatgagctg   8880
atttaacaaa aatttaacgc gaattttaac aaaatattaa cgcttacaat ttag         8934
```